United States Patent
Freeman et al.

(10) Patent No.: US 10,202,454 B2
(45) Date of Patent: Feb. 12, 2019

(54) ANTI-PD-L1 MONOCLONAL ANTIBODIES AND FRAGMENTS THEREOF

(71) Applicant: DANA-FARBER CANCER INSTITUTE, INC., Boston, MA (US)

(72) Inventors: Gordon J. Freeman, Brookline, MA (US); Arlene H. Sharpe, Brookline, MA (US)

(73) Assignees: Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 102 days.

(21) Appl. No.: 15/029,369

(22) PCT Filed: Oct. 24, 2014

(86) PCT No.: PCT/US2014/062149
§ 371 (c)(1),
(2) Date: Apr. 14, 2016

(87) PCT Pub. No.: WO2015/061668
PCT Pub. Date: Apr. 30, 2015

(65) Prior Publication Data
US 2016/0272712 A1 Sep. 22, 2016

Related U.S. Application Data

(60) Provisional application No. 61/895,543, filed on Oct. 25, 2013.

(51) Int. Cl.
| | |
|---|---|
| *C07K 16/28* | (2006.01) |
| *G01N 33/574* | (2006.01) |
| *C07K 16/30* | (2006.01) |
| *G01N 33/577* | (2006.01) |
| *A61K 39/00* | (2006.01) |

(52) U.S. Cl.
CPC ......... *C07K 16/2827* (2013.01); *C07K 16/30* (2013.01); *C07K 16/3023* (2013.01); *C07K 16/3038* (2013.01); *C07K 16/3061* (2013.01); *C07K 16/3069* (2013.01); *G01N 33/577* (2013.01); *G01N 33/57484* (2013.01); *A61K 2039/505* (2013.01); *C07K 2317/14* (2013.01); *C07K 2317/565* (2013.01); *G01N 2333/70596* (2013.01)

(58) Field of Classification Search
CPC .............. C07K 16/2827; C07K 16/00–16/468
See application file for complete search history.

(56) References Cited

U.S. PATENT DOCUMENTS

| | | | |
|---|---|---|---|
| 7,754,208 B2 | 7/2010 | Ledbetter et al. | |
| 7,943,743 B2* | 5/2011 | Korman | C07K 16/2803 530/388.15 |
| 8,217,149 B2 | 7/2012 | Irving et al. | |
| 8,552,154 B2 | 10/2013 | Freeman et al. | |
| 8,779,108 B2* | 7/2014 | Queva | C07K 16/2827 530/388.73 |
| 9,175,082 B2* | 11/2015 | Zhou | C07K 16/2818 |
| 9,212,224 B2* | 12/2015 | Cogswell | C07K 16/2827 |
| 9,624,298 B2* | 4/2017 | Nastri | A61K 39/3955 |
| 9,845,356 B2* | 12/2017 | Freeman | G01N 33/57492 |
| 2009/0162358 A1* | 6/2009 | Alard | C07K 16/18 424/136.1 |
| 2010/0034820 A1 | 2/2010 | Ledbetter et al. | |
| 2011/0301332 A1* | 12/2011 | Wilson | C07K 16/26 530/387.3 |

FOREIGN PATENT DOCUMENTS

| | | |
|---|---|---|
| WO | WO-2013/079174 A1 | 6/2013 |
| WO | WO-2014/165082 A2 | 10/2014 |

OTHER PUBLICATIONS

Bellmunt et al., "Association of PD-L1 expression on tumor-infiltrating mononuclear cells and overall survival in patients with urothelial carcinoma," Ann. Oncol. 26:812-817 (2015).
Brown et al., "Blockade of Programmed Death-1 Ligands on Dendritic Cells Enhances T Cell Activation and Cytokine Production," J. Immunol. 170:1257-1266 (2003).
Callea et al., "PD-L1 expression in primary clear cell renal cell carcinomas (ccRCCs) and their metastases," J. Clin. Oncol. 32(suppl.):4585 Abstract #4585 presented at the 50th Annual ASCO Meeting (May 20, 2014).
Callea et al., "Differential Expression of PD-L1 between Primary and Metastatic Sites in Clear-Cell Renal Cell Carcinoma," Cancer Immunol. Res. 3:1158-1164 (2015).
Calles et al., "Differential expression of LKB1, PD-L1, and PD-L2 in KRAS-mutant non-small cell lung cancer in never-smokers," J. Clin. Oncol. 32(suppl.):8032 Abstract #8032 presented at the 50th Annual ASCO Meeting (May 20, 2014).
Calles et al., "Differential expression of LKB1, PD-L1, and PD-L2 in KRAS-mutant non-small cell lung cancer in never-smokers," Poster #8032 presented at the 50th Annual ASCO Meeting (Jun. 3, 2014).
Chen et al., "PD-L1 Expression is Characteristic of a Subset of Aggressive B-cell Lymphomas and Virus-Associated Malignancies," Clin. Cancer Res. 19:3462-3473 (2013).
Choueiri et al., "PD-L1 expression in nonclear-cell renal cell carcinoma," Ann. Oncol. 25:2178-2184 (2014).
Dorfman et al., "Programmed Death-1 (PD-1) is a Marker of Germinal Center-assocaited T Cells and Angioimmunoblastic T-Cell Lymphoma," Am. J. Surg. Pathol. 30:802-810 (2006).

(Continued)

*Primary Examiner* — Jessica H Roark
(74) *Attorney, Agent, or Firm* — Foley Hoag LLP

(57) ABSTRACT

The present invention is based, in part, on the discovery of monoclonal antibodies that specifically bind to the cytoplasmic domain of PD-L1 antibodies useful for diagnostic, prognostic, and therapeutic applications, as well as immunoglobulins polypeptides, and nucleic acids thereof.

19 Claims, 13 Drawing Sheets
Specification includes a Sequence Listing.

(56) References Cited

OTHER PUBLICATIONS

Mahoney et al., "PD-L1 Antibodies to its Cytoplasmic Domain Most Clearly Delineate Cell Membranes in Immunohistochemical Staining of Tumor Cells," Cancer Immunol. Res. 3:1308-1315 (2015).

Mullane et al., "PD-L1 expression in mononuclear cells and not in tumor cells, correlated with prognosis in metastatic urothelial carcinoma," J. Clin. Oncol. 32(suppl.):4552 Abstract #4552 presented at the 50th Annual ASCO Meeting (May 20, 2014).

International Search Report dated Feb. 23, 2015 from PCT/US2014/062149.

AbD Serotec: Catalogue d'anticorps 2011 (retrieved from the Internet at https://www.abdserotec.com/catalogue-de-r-1123.html) [accessed on Jul. 22, 2015], XP055204113A (2012).

Datasheet: AHP2128 Product Details (retrieved from the Internet at https://static.abdserotec.com/datasheets/ahp21/human-cd274-antibody-ahp2128.pdf) [accessed on Jul. 22, 2015], XP55204120A (2015).

Duchnowska et al., "Immune response in breast cancer brain metastases and their microenvironment: the role of the PD-1/PdD-L axis," Breast Cancer Res, 18(1):43 (2016).

Extended European Search Report issued by the European Patent Office in corresponding International Application No. PCT/US2014/062149, dated May 10, 2017.

\* cited by examiner

Figure 2
A
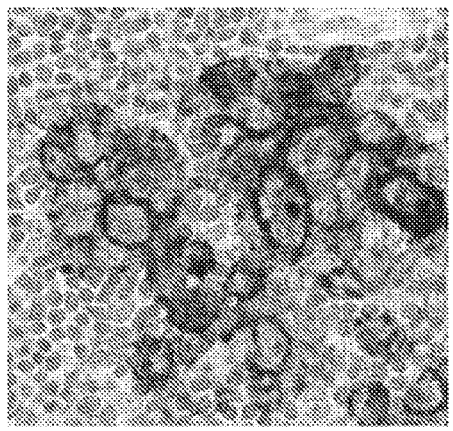
C
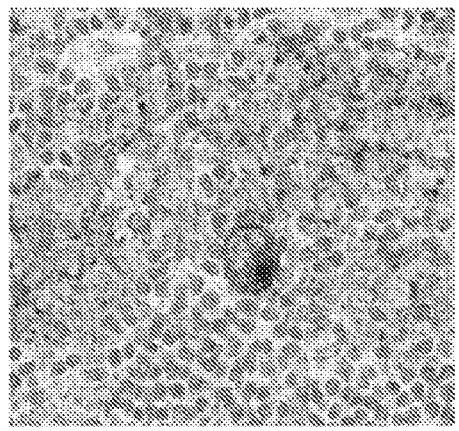
B
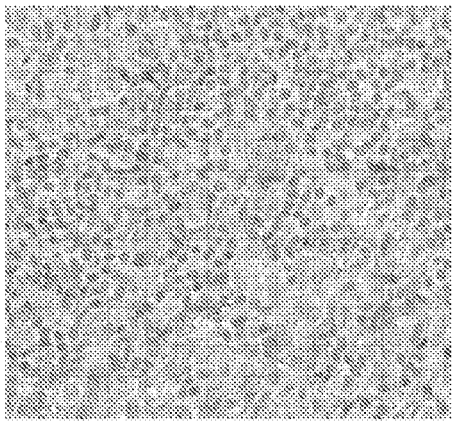
D
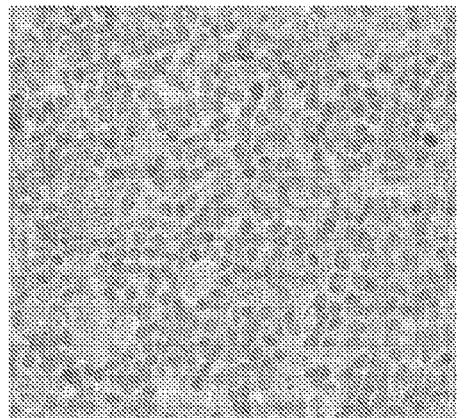

Figure 7
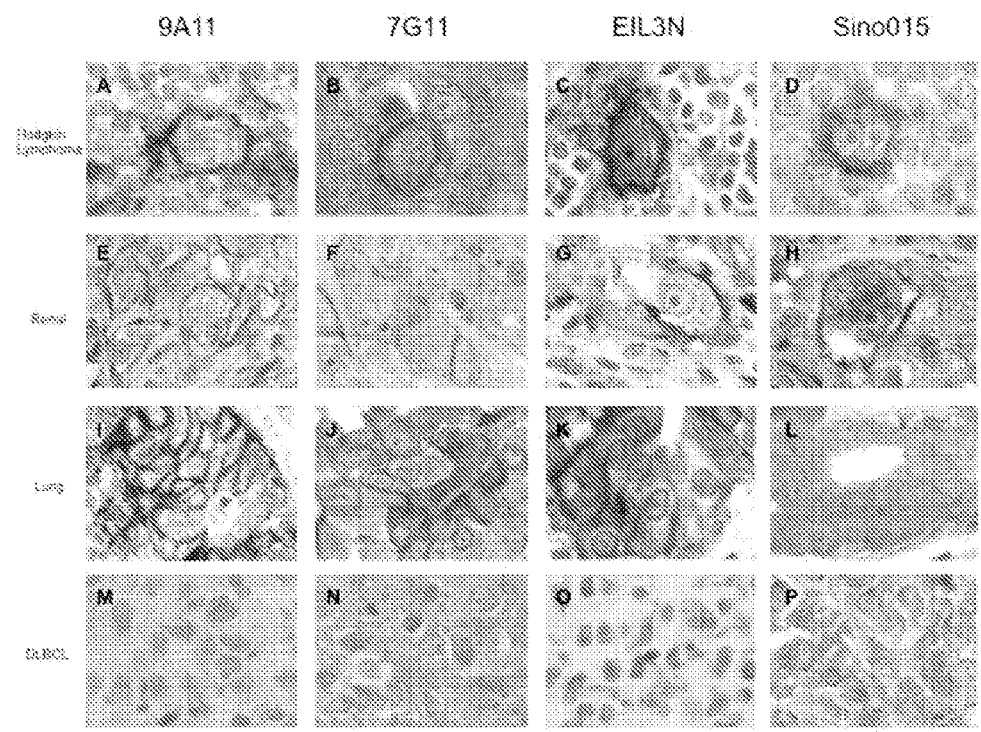
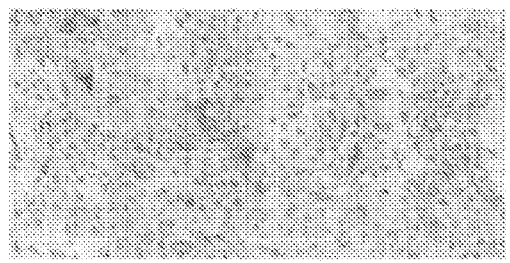
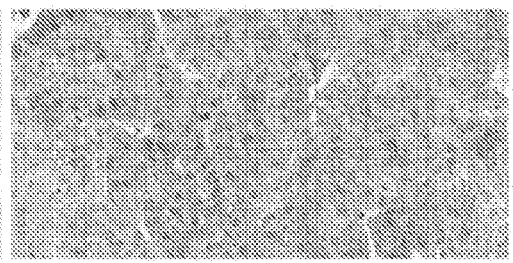

Absent or focal — — —
Mild Moderate and Severe ·······

Figure 13
A
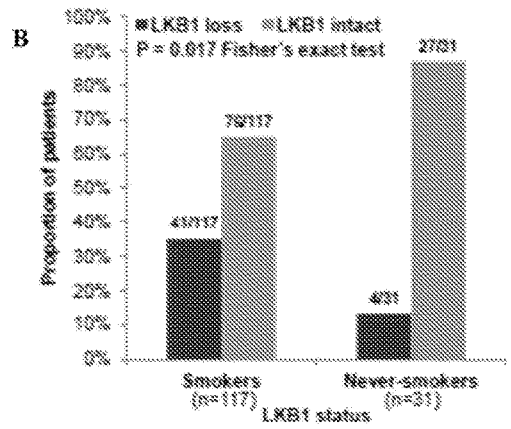
B
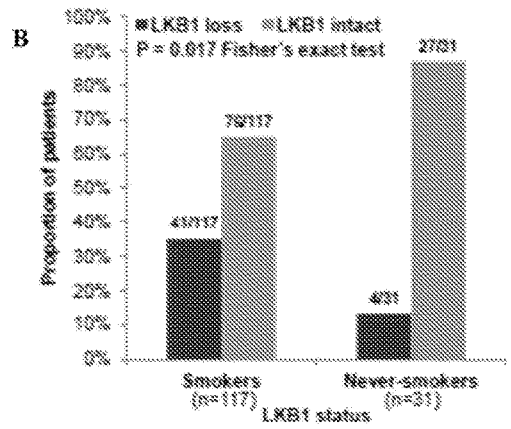
C
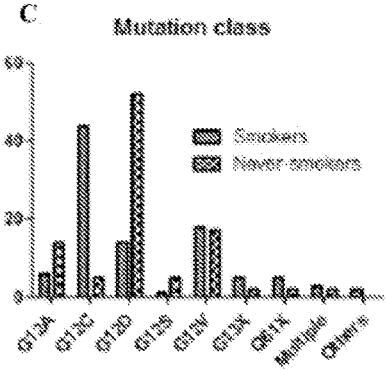
D
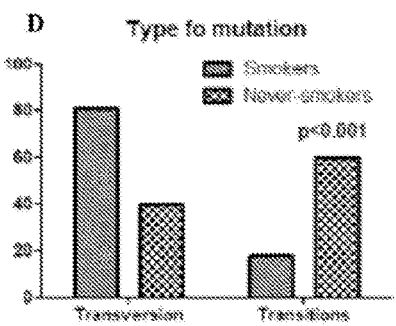
E

Figure 13 (cont.)
F
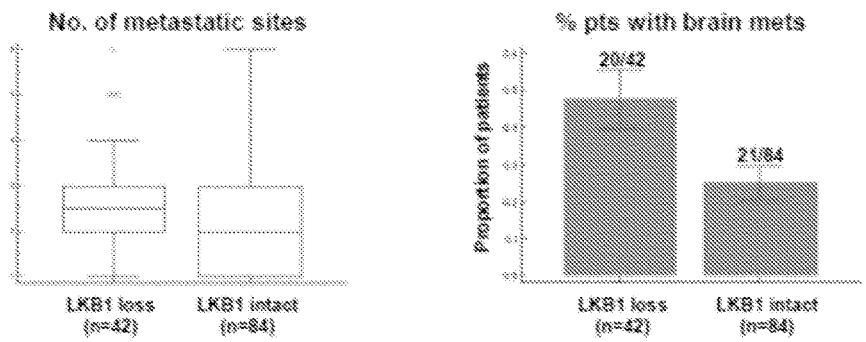
G
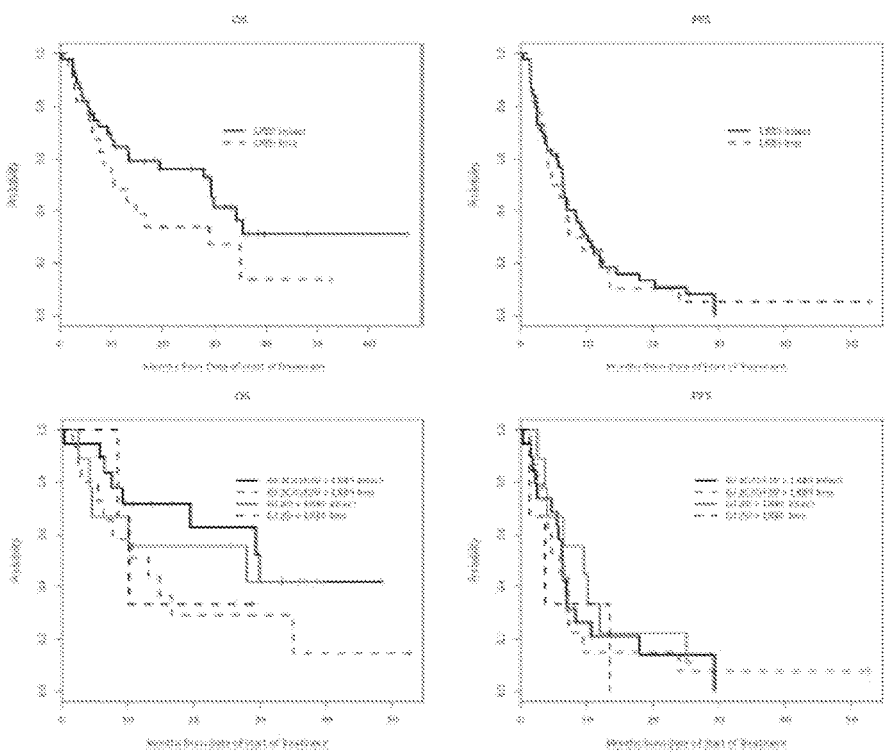

J

ANTI-PD-L1 MONOCLONAL ANTIBODIES AND FRAGMENTS THEREOF

STATEMENT OF RIGHTS

This invention was made with government support under grant numbers P01AI056299, P01AI054456, and HHSN272201100018C awarded by The National Institutes of Health. The government has certain rights in the invention.

CROSS-REFERENCE TO RELATED APPLICATIONS

This application is the U.S. National Stage Application of International Application No. PCT/US2014/062149, filed on 24 Oct. 2014, and which claims the benefit of U.S. Provisional Application No. 61/895,543, filed on 25 Oct. 2013; the entire contents of each of said applications is incorporated herein in its entirety by this reference.

BACKGROUND OF THE INVENTION

Programmed cell death 1 ligand 1 (PD-L1) is a member of the B7 family of immunological modulating molecules that has been demonstrated to have an immunoinhibitory function mediated through interactions with the PD-1 receptor, as well as to have costimulatory function in some contexts through interactions with an as yet unidentified receptor (U.S. Pat. No. 6,936,704; U.S. Pat. Publ. 2009/0317368; Keir et al. (2008) *Annu. Rev. Immunol.* 26:677-704; and Xu et. al. (2013) *PLoS One* 8:e56539). PD-1 is a member of the immunoglobulin family of molecules (Ishida et al. (1992) *EMBO. J.* 11:3887; Shinohara et al. (1994) (Genomics 23:704) and is believed to play a role in lymphocyte survival, e.g., during clonal selection (Honjo (1992) *Science* 258:591; Agata et al. (1996) *Int. Immunology.* 8:765; Nishimura et al. (1996) *Int. Immunology* 8:773) based on its function as an inhibitory receptor similar to that of CTLA4 (Wu et al. (2012) *Int. J. Biol. Sci.* 8:1420-1430). While engagement of a costimulatory receptor results in a costimulatory signal in an immune cell, engagement of an inhibitory receptor, e.g., CTLA-4 or PD-1 (for example by crosslinking or by aggregation), leads to the transmission of an inhibitory signal in an immune cell, resulting in downmodulation of immune cell responses and/or in immune cell anergy. While transmission of an inhibitory signal leads to downmodulation in immune cell responses (and a resulting downmodulation in the overall immune response), the prevention of an inhibitory signal in cells, such as immune cells, leads to upmodulation of immune cell responses (and a resulting upmodulation of an immune response).

Numerous blocking antibodies targeting PD-L1 are currently under review in clinical trials for treating a number of immune-related disorders (reviewed in Keir et al. (2008) *Annu. Rev. Immunol.* 26:677-704; Wu et al. (2012) *Int. J. Biol. Sci.* 8:1420-1430; Sakthivel et al. (2012) *Rev. Recent Clin. Trials* 7:10-23; Flies et al. (2011) *Yale J. Biol. Med.* 84:409-421; Topalian et al. (2012) *Curr. Opin. Immunol.* 24:207-212; Sarasella et al. (2012) *Curr. Mol. Med.* 12:259-267; Riella et al. (2012) *Am. J. Transplant.* 12:2575-2587; and Inozume (2013) *Nihon Rinsho Meneki Gakkai Kasishi* (2013) 36:134-138). However, the anti-PD-L1 antibodies used in such trials have several disadvantages. First, they recognize and bind to the extracellular domain of PD-L1. While recognizing such epitopes disrupt interactions with PD-L1 receptors, such epitopes do not allow the antibody to distinguish between membrane-bound forms of PD-L1 versus soluble forms of PD-L1. Soluble forms of PD-L1 have been determined to have distinct structural characteristics and biologically relevant functions relative to membrane-bound forms of PD-L1 (U.S. Pat. No. 6,936,704; Chen et al. (2011) *Cytokine* 56:231-238; Frigola et al. (2011) *Clin. Cancer Res.* 17:1915-1923; and Frigola et al. (2012) *Immunol. Lett.* 142-78-82). For example, concomitant recognition of soluble PD-L1 presents high and undesired background staining upon immunohistochemical analyses of membrane-bound PD-L1 protein. Second, anti-PD-L1 antibodies targeting the extracellular domain of PD-L1, which represents the vast majority of surface availability for antibody recognition, will bind to and sequester the protein when administered for therapeutic or other uses, such that additional areas of protein recognition useful for continued monitoring, diagnosis, and prognosis of PD-L1 expression and activity will be hindered.

Accordingly, there is a need in the art to identify new anti-PD-L1 antibodies having a specificity and sensitivity for cytoplasmic portions of membrane-bound PD-L1.

SUMMARY OF THE INVENTION

The present invention relates in general to anti-PD-L1 monoclonal antibodies, and immunoglobulins, polypeptides, and nucleic acids thereof, useful for the diagnosis, prognosis, monitoring, and treatment of disorders associated with aberrant PD-L1 expression (e.g., cancer).

In one aspect, a monoclonal antibody, or antigen-binding fragment thereof, is provided, wherein the monoclonal antibody comprises: a) a heavy chain sequence with at least about 95% identity to a heavy chain sequence selected from the group consisting of the sequences listed in Table 1 or b) a light chain sequence with at least about 95% identity to a light chain sequence selected from the group consisting of the sequences listed in Table 1. In one embodiment, the monoclonal antibody, or antigen-binding fragment thereof, comprises: a) a heavy chain CDR sequence with at least about 95% identity to a heavy chain CDR sequence selected from the group consisting of the sequences listed in Table 1 or b) a light chain CDR sequence with at least about 95% identity to a light chain CDR sequence selected from the group consisting of the sequences listed in Table 1. In another embodiment, the monoclonal antibody, or antigen-binding fragment thereof, comprises: a) a heavy chain sequence selected from the group consisting of the sequences listed in Table 1; or b) a light chain sequence selected from the group consisting of the sequences listed in Table 1. In still another embodiment, the monoclonal antibody, or antigen-binding fragment thereof, comprises: a) a heavy chain CDR sequence selected from the group consisting of the sequences listed in Table 1; or b) a light chain CDR sequence selected from the group consisting the sequences listed in Table 1. In yet another embodiment, the monoclonal antibody, or antigen-binding fragment thereof, is chimeric, humanized, composite, murine, or human. In another embodiment, the monoclonal antibody, or antigen-binding fragment thereof, is detectably labeled, comprises an effector domain, comprises an Fc domain, and/or is selected from the group consisting of Fv, Fav, F(ab')2). Fab', dsFv, scFv, sc(Fv)2, and diabodies fragments. In still another embodiment, the monoclonal antibody, or antigen-binding fragment thereof, inhibits the binding of commercial antibody to PD-L1. In yet another embodiment, the monoclonal antibody, or antigen-binding fragment thereof, is obtainable from hybridoma 405.1.9A11.2D6.3.5 deposited under deposit accession number PTA-124921.

In another aspect, an immunoglobulin heavy and/or light chain of any monoclonal antibody, or antigen-binding fragment thereof, described herein, is provided.

In still another aspect, an isolated nucleic acid molecule that hybridizes, under stringent conditions, with the complement of a nucleic acid encoding a polypeptide selected from the group consisting of the sequences listed in Table 1, or a sequence with at least about 95% homology to a nucleic acid encoding a polypeptide selected from the group consisting of the sequences listed in Table 1, is provided.

In yet another aspect, a vector comprising such an isolated nucleic acid is provided.

In another aspect, a host cell which comprises an isolated nucleic acid, a vector, expresses a monoclonal antibody, or antigen-binding fragment thereof or is accessible under deposit access number PTA-124921, described herein, is provided.

In still another aspect, a device or kit comprising at least one monoclonal antibody or antigen-binding fragment thereof, described herein is provided, wherein said device or kit optionally comprising a label to detect the at least one monoclonal antibody or antigen-binding fragment thereof, or a complex comprising the monoclonal antibody or antigen-binding fragment thereof.

In yet another aspect, a method of producing an antibody, or antigen-binding fragment thereof, described herein, which method comprises the steps of: (i) culturing a transformed host cell which has been transformed by a nucleic acid comprising a sequence encoding a monoclonal antibody according to claim 1 under conditions suitable to allow expression of said antibody, or antigen-binding fragment thereof; and (ii) recovering the expressed antibody, or antigen-binding fragment thereof.

In another aspect, a method of detecting the presence or level of a PD-L1 polypeptide is provided, wherein said method comprises obtaining a sample and detecting said polypeptide in a sample by use of at least one monoclonal antibody, or antigen-binding fragment thereof, described herein. In one embodiment, the at least one monoclonal antibody, or antigen-binding fragment thereof, forms a complex with a PD-L1 polypeptide and the complex is detected in the form of an enzyme linked immunosorbent assay (ELISA), radioimmune assay (RIA), immunochemically, or using an intracellular flow assay.

In still another aspect a method for monitoring the progression of a disorder associated with aberrant PD-L1 expression in a subject is provided, wherein the method comprises: a) detecting in a subject sample at a first point in time the level of expression of PD-L1 using at least one monoclonal antibody, or antigen-binding fragment thereof, described herein; b) repeating step a) at a subsequent point in time; and c) comparing the level of expression of said PD-L1 detected in steps a) and b) to monitor the progression of the disorder in the subject. In one method, the subject has undergone treatment to ameliorate the disorder between the first point in time and the subsequent point in time.

In yet another aspect, a method for predicting the clinical outcome of a subject afflicted with a disorder associated with aberrant PD-L1 is provided, wherein the method comprises: a) determining the level of expression of PD-L1 in a patient sample using at least one monoclonal antibody, or antigen-binding fragment thereof, described herein; b) determining the level of expression of PD-L1 in a sample from a control subject having a good clinical outcome using at least one monoclonal antibody, or antigen-binding fragment thereof, described herein; and c) comparing the level of expression of PD-L1 in the patient sample and in the sample from the control subject; wherein a significantly higher level of expression in the patient sample as compared to the expression level in the sample from the control subject is an indication that the patient has a poor clinical outcome.

In another aspect, a method of assessing the efficacy of a therapy for a disorder associated with aberrant PD-L1 in a subject is provided, wherein the method comprises comparing: a) the level of expression of PD-L1 using at least one monoclonal antibody, or antigen-binding fragment thereof, described herein, in a first sample obtained from the subject prior to providing at least a portion of the therapy to the subject, and b) the level of expression of PD-L1 in a second sample obtained from the subject following provision of the portion of the therapy, wherein a significantly lower level of expression of PD-L1 in the second sample, relative to the first sample, is an indication that the therapy is efficacious for inhibiting the disorder in the subject.

In still another aspect, a method of assessing the efficacy of a test compound for inhibiting a disorder associated with aberrant PD-L1 in a subject is provided, wherein the method comprises comparing: a) the level of expression of PD-L1 using at least one monoclonal antibody, or antigen-binding fragment thereof, described herein, in a first sample obtained from the subject and exposed to the test compound; and b) the level of expression of PD-L1 in a second sample obtained from the subject, wherein the second sample is not exposed to the test compound, and a significantly lower level of expression of PD-L1, relative to the second sample, is an indication that the test compound is efficacious for inhibiting the disorder in the subject. In one embodiment, the first and second samples are portions of a single sample obtained from the subject or portions of pooled samples obtained from the subject.

For any aspect of the present invention described herein, certain specific embodiments are contemplated. For example, in one embodiment, the disorder is a cancer. In another embodiment, the sample comprises cells, serum, peritumoral tissue, and/or intratumoral tissue obtained from the subject. In still another embodiment, a significant increase comprises an at least twenty percent increase between the level of expression of PD-L1 in the subject sample relative to the normal level of expression of PD-L1 in the sample from the control subject. In yet another embodiment, the subject is a human.

BRIEF DESCRIPTION OF FIGURES

FIGS. 2A-2D show the results of immunohistochemistry analyses of paraffin-embedded classical Hodgkin lymphoma using the 405.9A11 mAb (FIGS. 2A-2B) or the 339.7G11 mAb (FIGS. 2C-2D).

FIGS. 7A-R show representative photomicrographs of select tumors stained with anti-PD-L1 antibodies. Reed-Sternberg cells of classical Hodgkin lymphoma (A-D), renal cell carcinoma (E-H), lung adenocarcinoma (1-L), and diffuse large B-cell lymphoma (M-P) stained with monoclonal antibodies 9A11 (A, E, I, M), 7G11 (B, F, J, N), E1L3N (C, G, K, O), and 015 (D, H, L, P) are shown. The Reed-Sternberg cells of Hodgkin lymphoma and the tumor cells of renal cell carcinoma (RCC) and lung adenocarcinoma show distinctly membrane staining (coloration) that is not observed in the tumor cells of diffuse large B-cell lymphoma. Weak cytoplasmic staining and weak extracellular staining is present with the 7G11 and 015 antibodies and largely absent with the 9A11 and E1L3N antibodies. FIGS. 7Q-7R show staining of sections from the same RCC tumor with 9A11 or 7G11 as indicated.

FIG. 8B: negative control—PD-L1 negative; FIG. 8C: PD-L1 positive in tumor cell membrane; and FIG. 8D: PD-L1 positive in TIMC) as immunostained with anti-PD-L1 antibody (clone 9A11).

FIG. 11B: negative cell line control; FIG. 11C: chromophore RCC; FIG. 11D: papillary RCC; and FIGS. 11E-11F: Xp11.2 translocation RCC) as immunstained with anti-PD-L1 antibody (clone 405.9A11). Positive staining in tumor cell membranes are shown in FIGS. 11C-11E. In FIG. 11F, tumor cell membranes are negative for PD-L1 and tumor infiltrating immune cells are positive for PD-L1.

DETAILED DESCRIPTION OF THE INVENTION

Figure 1:
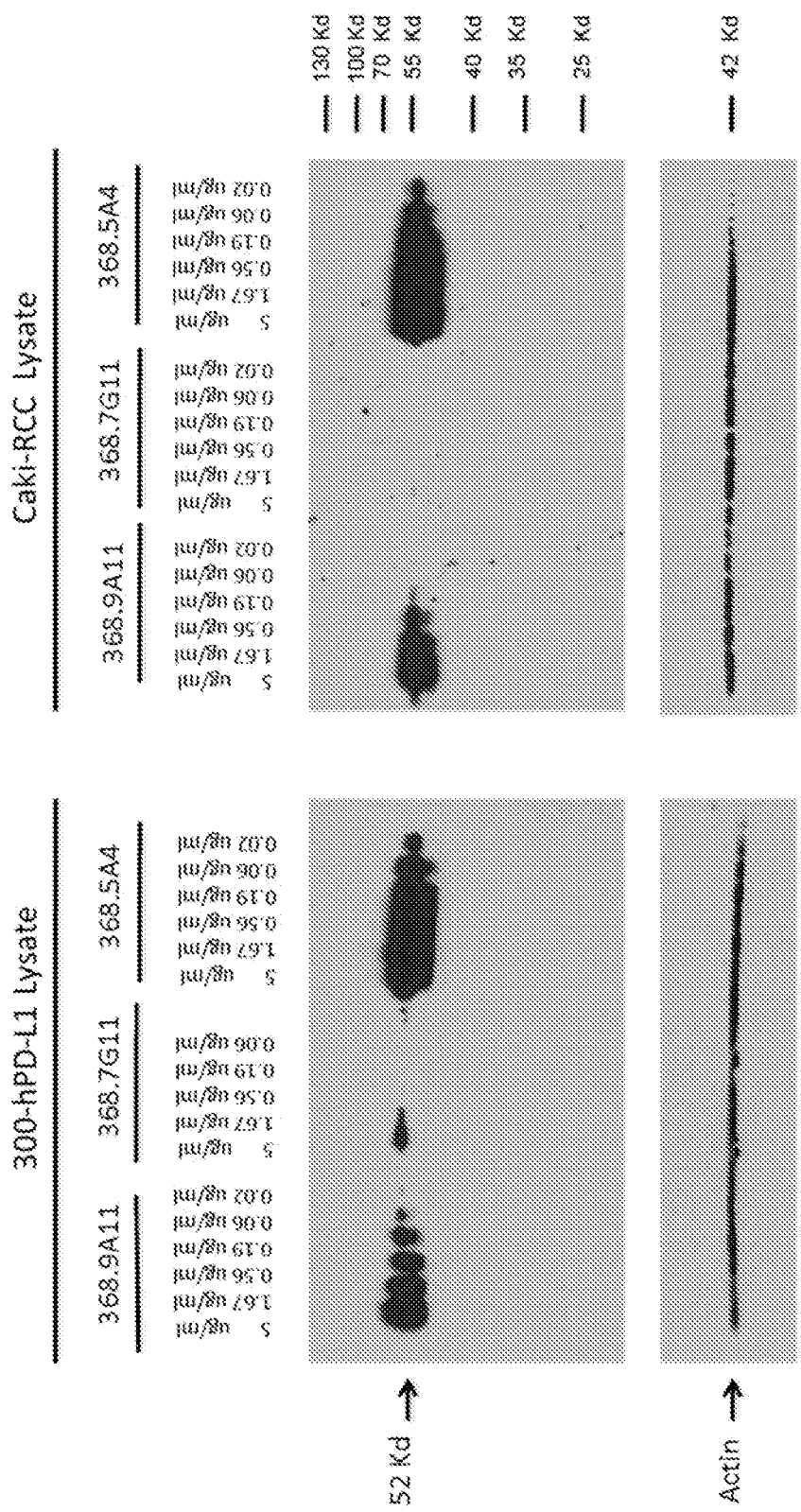
FIG. 1 shows Western blot results of anti-PD-L1 monoclonal antibody, 9A11, and other anti-human PD-L1 monoclonal antibodies used to detect protein lysates derived from 300.19 cells stably transfected with human PD-L1 or Caki-2 cells, a human renal clear cell carcinoma cell line which naturally expresses a low level of PD-L1 protein typical of solid tumor cell lines.

The present invention is based in part on the discovery of new anti-PD-L1 monoclonal antibodies that can bind to and detect the cytoplasmic domain of membrane-bound PD-L1. Moreover, such antibodies provide an unexpectedly superior ability to detect membrane-bound PD-L1 polypeptides in detection assays (e.g., Western blot, immunohistochemistry, flow cytometry, and the like) and may alter PD-L1 function by modulating its intracellular signaling. Such antibodies exhibit much lower background signal due to traditional detection of both cytoplasmic and membrane-bound PD-L1 by existing anti-PD-L1 antibodies and robustly detect PD-L1 cytoplasmic domains in non-fresh tissue samples (e.g., paraffinized tissues, fixed tissues, etc.). Such antibodies are further useful for the multiplex (e.g., combinatorial) detection of other immunomodulatory molecules, such as PD-1, PD-L2, CTLA4, B7-L, B7-2, and the like, and for functionally modulating PD-L1 signaling, thereby functioning to modulate in vitro, ex vivo, and/or in vivo immune responses.

I. Definitions

The articles "a" and "an" are used herein to refer to one or to more than one (i.e. to at least one) of the grammatical object of the article. By way of example, "an element" means one element or more than one element.

The term "altered amount" of a marker refers to increased or decreased copy number of a marker and/or increased or decreased nucleic acid level of a particular marker gene or genes in a sample, as compared to that of the marker in a control sample. The term "altered amount" of a marker also includes an increased or decreased protein level of a marker in a sample, as compared to the protein level of the marker in a normal, control sample.

The term "altered activity" of a marker refers to an activity of a marker which is increased or decreased in a disease state, e.g., in a biological sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The term "altered structure" of a marker refers to the presence of mutations or allelic variants within the marker gene or maker protein, e.g., mutations which affect expression or activity of the marker, as compared to the normal or wild-type gene or protein. For example, mutations include, but are not limited to substitutions, deletions, or addition mutations. Mutations may be present in the coding or non-coding region of the marker.

The term "altered subcellular localization" of a marker refers to the mislocalization of the marker within a cell relative to the normal localization within the cell e.g., within a healthy and/or wild-type cell. An indication of normal localization of the marker can be determined through an analysis of subcellular localization motifs known in the field that are harbored by marker polypeptides or, for example, through cellular analyses such as internalization of normally extracellular mature functional PD-L1.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. "Inactivating antibodies" refers to antibodies that do not induce the complement system.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., PD-L1 polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242: 423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger. P., et al. (1993) *Proc. Natl. Acad Sci. USA* 90:6444-6448; Poljak, R. J., et al. (1994) *Structure* 2:1121-1123).

Still further, an antibody or antigen-binding portion thereof may be part of larger immunoadhesin polypeptides, formed by covalent or noncovalent association of the antibody or antibody portion with one or more other proteins or peptides. Examples of such immunoadhesin polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesin polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. In one embodiment, antibodies of the present invention bind specifically or substantially specifically to PD-L1 polypeptides or fragments thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

The terms "CDR", and its plural "CDRs", refer to a complementarity determining region (CDR) of which three make up the binding character of a light chain variable region (CDR-L1, CDR-L2 and CDR-L3) and three make up the binding character of a heavy chain variable region (CDR-H1, CDR-H2 and CDR-H3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., in "Sequences of Proteins of Immunological Interest," 5 Edition, U.S. Department of Health and Human Services, 1992; Chothia er al. (1987) J. Mol. Biol. 196, 901; and MacCallum et al., J. Mol. Biol. (1996) 262, 732, each of which is incorporated by reference in its entirety).

As used herein, the term "classifying" includes "to associate" or "to categorize" a sample with a disease state. In certain instances, "classifying" is based on statistical evidence, empirical evidence, or both. In certain embodiments, the methods and systems of classifying use of a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

As used herein, the term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which as antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In one embodiment, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. In another embodiment, all nucleotide residues of the first portion are capable of base pairing with nucleotide residues in the second portion.

As used herein, the term "composite antibody" refers to an antibody which has variable regions comprising germline or non-germline immunoglobulin sequences from two or more unrelated variable regions. Additionally, the term "composite, human antibody" refers to an antibody which has constant regions derived from human germline or non-germline immunoglobulin sequences and variable regions comprising human germline or non-germline sequences from two or more unrelated human variable regions. A composite, human antibody is useful as an effective component in a therapeutic agent according to the present invention since the antigenicity of the composite, human antibody in the human body is lowered.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

As used herein, the term "Fc region" is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. Suitable native-sequence Fc regions for use in the antibodies of the present invention include human IgG1, IgG2 (IgG2A, IgG2B), IgG3 and IgG4.

As used herein. "Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see M. Daëron, *Annu. Rev. Immunol.* 15:203-234 (1997). FcRs are reviewed in Ravetch and Kinet, *Ann. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

As used herein, "Framework" or "FR" residues are those variable-domain residues other than the HVR residues as herein defined.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

As used herein, the term "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATT-GCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

As used herein, the term "host cell" is intended to refer to a cell into which a nucleic acid of the present invention, such as a recombinant expression vector of the present invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. Humanized antibodies may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

As used herein, the term "hypervariable region," "HVR," or "HV," refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. (2000) Immunity 13, 37-45; Johnson and Wu in Methods in Molecular Biology 248, 1-25 (Lo, ed., Human Press, Totowa, N.J., 2003)). Indeed, naturally occurring camelid antibodies consisting of a heavy chain only are functional and stable in the absence of light chain (see, e.g., Hamers-Casterman et al. (1993) Nature 363:446-448 (1993) and Sheriff et al. (1996) Nature Struct. Biol. 3, 733-736).

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "immune checkpoints" means a group of molecules on the cell surface of CD4+ and CD8+ T cells. These molecules fine-tune immune responses by down-modulating or inhibiting an anti-tumor immune response. Immune checkpoint proteins are well known in the art and include, without limitation, PD-L1, as well as CTLA-4, PD-1, VISTA, B7-H2, B7-H3, B7-H4, B7-H6, 2B4, ICOS, HVEM, PD-L2, CD160, gp49B, PIR-B, KIR, TIM-3, LAG-3, HHLA2, butyrophilins, and BTLA (see, for example, WO 2012/177624).

As used herein, the term "immune disorder" includes immune diseases, conditions, and predispositions to, including, but not limited to, cancer, chronic inflammatory disease and disorders (including. e.g., Crohn's disease, inflammatory bowel disease, reactive arthritis, and Lyme disease), insulin-dependent diabetes, organ specific autoimmunity (including, e.g., multiple sclerosis, Hashimoto's thyroiditis, autoimmune uveitis, and Grave's disease), contact dermatitis, psoriasis, graft rejection, graft versus host disease, sarcoidosis, atopic conditions (including, e.g., asthma and allergy including, but not limited to, allergic rhinitis and gastrointestinal allergies such as food allergies), eosinophilia, conjunctivitis, glomerular nephritis, systemic lupus erythematosus, scleroderma, certain pathogen susceptibilities such as helminthic (including, e.g., leishmaniasis) and certain viral infections (including, e.g., HIV and bacterial infections such as tuberculosis and lepromatous leprosy) and malaria.

As used herein, the term "immune response" includes T cell mediated and/or B cell mediated immune responses. Exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages.

As used herein, the term "inhibiting" and grammatical equivalents thereof refer decrease, limiting, and/or blocking a particular action, function, or interaction. In one embodiment, the term refers to reducing the level of a given output or parameter to a quantity (e.g., background staining, PD-L1 signaling, PD-L1 immunoinhibitory function, and the like) which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control. A reduced level of a given output or parameter need not, although it may, mean an absolute absence of the output or parameter. The invention does not require, and is not limited to, methods that wholly eliminate the output or parameter. The given output or parameter can be determined using methods well known in the art, including, without limitation, immunohistochemical, molecular biological, cell biological, clinical, and biochemical assays, as discussed herein and in the examples. The opposite terms "promoting," "increasing," and grammatical equivalents thereof refer to the increase in the level of a given output or parameter that is the reverse of that described for inhibition or decrease.

As used herein, the term "interaction", when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting an immune response). To inhibit such an interaction results in the disruption of the activity of one or more molecules involved in the interaction. To enhance such an interaction is to prolong or increase the likelihood of said physical contact, and prolong or increase the likelihood of said activity.

As used herein, the term an "isolated antibody" is intended to refer to an antibody which is substantially free of other antibodies having different antigenic specificities (e.g., an isolated antibody that specifically binds to the cytoplasmic domain of human PD-L1 and is substantially free of antibodies that do not bind to the cytoplasmic domain of PD-L1). An isolated antibody that specifically binds to a cytoplasmic epitope of human PD-L1 may, however, have cross-reactivity to other PD-L1 proteins, respectively, from different species. However, in some embodiments, the antibody maintains higher or indeed specific affinity and selectivity for human PD-L1. In addition, an isolated antibody is typically substantially free of other cellular material and/or chemicals. In one embodiment of the present invention, a combination of "isolated" monoclonal antibodies having different specificities to human PD-L1 are combined in a well defined composition.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a target polypeptide (e.g., immunoglobulin) or fragment thereof, in which the protein is separated from cellular components of the cells from which it is isolated or recombinantly produced. In one embodiment, the language "substantially free of cellular material" includes preparations of target protein or fragment thereof, having less than about 30% (by dry weight) of non-target protein (also referred to herein as a "contaminating protein"), more preferably less than about 20% of non-target protein, still more preferably less than about 10% of non-target protein, and most preferably less than about 5% non-target protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10% t, and most preferably less than about 5% of the volume of the protein preparation.

As used herein, the term "isotype" refers to the antibody class (e.g., IgM or IgG1) that is encoded by heavy chain constant region genes.

As used herein, the term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

As used herein, a "kit" is any manufacture (e.g. a package or container) comprising at least one reagent, e.g. a probe, for specifically detecting or modulating the expression of a marker of the present invention. The kit may be promoted, distributed, or sold as a unit for performing the methods of the present invention.

As used herein, the term "monoclonal antibody", refers to an antibody which displays a single binding specificity and affinity for a particular epitope. Accordingly, the term "human monoclonal antibody" refers to an antibody which displays a single binding specificity and which has variable and constant regions derived from human germline or non-germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

A "marker" is a gene whose altered level of expression in a tissue or cell from its expression level in normal or healthy tissue or cell is associated with a disease state, such as cancer. A "marker nucleic acid" is a nucleic acid (e.g., mRNA, cDNA) encoded by or corresponding to a marker of the present invention. Such marker nucleic acids include DNA (e.g., cDNA) comprising the entire or a partial sequence of any of the nucleic acid sequences set forth in the Sequence Listing or the complement of such a sequence. The marker nucleic acids also include RNA comprising the entire or a partial sequence of any of the nucleic acid sequences set forth in the Sequence Listing or the complement of such a sequence, wherein all thymidine residues are replaced with uridine residues. A "marker protein" is a protein encoded by or corresponding to a marker of the present invention. A marker protein comprises the entire or a partial sequence of any of the sequences set forth in the Sequence Listing. The terms "protein" and "polypeptide" are used interchangeably.

As used herein, the term "modulate" includes up-regulation and down-regulation, e.g., enhancing or inhibiting a response.

The "normal" level of expression of a marker is the level of expression of the marker in cells of a subject, e.g., a human patient, not afflicted with a viral-associated PTLD. An "over-expression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subjects not having the marker associated disease) and preferably, the average expression level of the marker in several control samples. A "significantly lower level of expression" of a marker refers to an expression level in a test sample that is at least twice, and more preferably three, four, five or ten times lower than the expression level of the marker in a control sample (e.g., sample from a healthy subject not having the marker associated disease) and preferably, the average expression level of the marker in several control samples.

As used herein, the term "nucleic acid molecule" is intended to include DNA molecules and RNA molecules. A nucleic acid molecule may be single-stranded or double-stranded, but preferably is double-stranded DNA. As used herein, the term "isolated nucleic acid molecule" in reference to nucleic acids encoding antibodies or antibody portions (e.g., $V_H$, $V_L$, CDR3) that bind to the cytoplasmic domain of PD-L1, is intended to refer to a nucleic acid molecule in which the nucleotide sequences encoding the antibody or antibody portion are free of other nucleotide sequences encoding antibodies or antibody portions that bind antigens other than PD-L1, which other sequences may naturally flank the nucleic acid in human genomic DNA.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

An "over-expression" or "significantly higher level of expression" of a marker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and preferably, the average expression level of the marker in several control samples. A "significantly lower level of expression" of a marker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus, internally, or at the carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. They can be, for example, at least and/or including 10, 15, 20, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, 980, 1000, 1020, 1040, 1060, 1080, 1100, 1120, 1140, 1160, 1180, 1200, 1220, 1240, 1260, 1280, 1300, 1320, 1340 or more long so long as they are less than the length of the full-length polypeptide. Alternatively, they can be no longer than and/or excluding such a range so long as they are less than the length of the full-length polypeptide.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

As used herein, the term "rearranged" refers to a configuration of a heavy chain or light chain immunoglobulin locus wherein a V segment is positioned immediately adjacent to a D-J or J segment in a conformation encoding essentially a complete $V_H$ and $V_L$ domain, respectively. A rearranged immunoglobulin gene locus can be identified by comparison to germline DNA; a rearranged locus will have at least one recombined heptamer/nonamer homology element.

As used herein, the term "recombinant host cell" (or simply "host cell"), is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The present invention "response" is generally related to for example, determining the effects on progression, efficacy, or outcome of a clinical intervention. In some embodiments, responses relate directly to a change in tumor mass and/or volume after initiation of clinical intervention (e.g., administration of an anti-PD-L1 monoclonal antibody). For example, hyperproliferative disorder responses may be assessed according to the size of a tumor after systemic intervention compared to the initial size and dimensions as measured by CT, PET, mammogram, ultrasound or palpation. Response may also be assessed by caliper measurement or pathological examination of the tumor after biopsy or surgical resection. Response may be recorded in a quantitative fashion like percentage change in tumor volume or in a qualitative fashion like "pathological complete response"

(pCR), "clinical complete remission" (cCR), "clinical partial remission" (cPR), "clinical stable disease" (cSD), "clinical progressive disease" (cPD) or other qualitative criteria. Assessment may be done early after the onset of the clinical intervention, e.g., after a few hours, days, weeks or preferably after a few months. A typical endpoint for response assessment is upon termination of the clinical intervention or upon surgical removal of residual tumor cells and/or the tumor bed.

As used herein, the term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using human PD-L1 as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

As used herein, "subject" refers to any healthy animal, mammal or human, or any animal, mammal or human afflicted with a viral-associated PTLD, e.g., EBV-associated PTLD. The term "subject" is interchangeable with "patient". The term "non-human animal" includes all vertebrates, e.g., mammals and non-mammals, such as non-human primates, sheep, dog, cow, chickens, amphibians, reptiles, etc.

The language "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

As used herein, the term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the present invention and normal post-transcriptional processing (e.g. splicing), if any, of the RNA transcript, and reverse transcription of the RNA transcript.

As used herein, the term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the term "unrearranged" or "germline configuration" in reference to a V segment refers to the configuration wherein the V segment is not recombined so as to be immediately adjacent to a D or J segment.

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 81%, 82%, 83%, 84%, 85%, 86%, 87%, 88%, 89%, 90%, 91%, 92%, 93%, 94%, 95%, 96%, or more of the nucleotides, and more preferably at least about 97%, 98%, 99% or more of the nucleotides. Alternatively, substantial homology exists when the segments will hybridize under selective hybridization conditions, to the complement of the strand.

The percent identity between two sequences is a function of the number of identical positions shared by the sequences (i.e., % identity=# of identical positions/total # of positions× 100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the world wide web at the GCG company website), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11 17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444 453 (1970)) algorithm which has been incorporated into the GAP program in the GCG software package (available on the world wide web at the GCG company website), using either a Blosum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403 10. BLAST nucleotide searches can be performed with the NBLAST program, score=100, wordlength=12 to obtain nucleotide sequences homologous to the nucleic acid molecules of the present invention. BLAST protein searches can be performed with the XBLAST program, score=50, wordlength=3 to obtain amino acid sequences homologous to the protein molecules of the present invention. To obtain gapped alignments for comparison purposes, Gapped BLAST can be utilized as described in Altschul et al., (1997) Nucleic Acids Res. 25(17):3389 3402. When utilizing BLAST and Gapped BLAST programs, the default parameters of the respective programs (e.g., XBLAST and NBLAST) can be used (available on the world wide web at the NCBI website).

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art (see, F. Ausubel, et al., ed. Current Protocols in Molecular Biology, Greene Publishing and Wiley Interscience, New York (1987)).

II. Monoclonal Antibodies, Immunoglobulins, and Polypeptides

The present invention relates, in part, to isolated monoclonal antibodies or fragments thereof that are directed against the cytoplasmic domain of PD-L1. Such molecules are characterized in that they exhibit a superior ability to recognize PD-L1 protein in diagnostic assays, such as immunohistochemical (IHC), Western blot, intercellular flow, ELISA, and the like, compared to known anti-PD-L1 antibodies that bind the extracellular domain of PD-L1.

Sequences, structures, domains, biophysical characteristics, and functions of PD-L1 gene and gene products have been described in the art. At least two forms of human PD-L1 molecules have been identified. One form is a naturally occurring PD-L1 soluble polypeptide, i.e., having a short hydrophilic domain and no transmembrane domain or cytoplasmic domain, and is referred to herein as PD-L1S (shown in Table 2). The second form is a cell-associated polypeptide, i.e., having a transmembrane and cytoplasmic domain, referred to herein as PD-L1M (shown in Table 2). The nucleic acid and amino acid sequences of representative human PD-L1 biomarkers regarding PD-L1M are also available to the public at the GenBank database under NM_014143.3 and NP_054862.1. PD-L1 proteins comprise a signal sequence, an IgV domain, and an IgC domain. Membrane-bound forms of PD-L1 further comprise a transmembrane domain and a cytoplasmic domain. While soluble forms of PD-L1 maintain sequences other than a signal sequence, an IgV domain, and an IgC domain, such sequences do not represent cytoplasmic domains as soluble forms of PD-L1 are generally secreted and are not maintained within the cytoplasm as is the case with membrane-bound forms of PD-L1. The signal sequence of PD-L1S in Table 2 is shown from about amino acid 1 to about amino acid 18. The signal sequence of PD-L1M in Table 2 is shown from about amino acid 1 to about amino acid 18. The IgV domain of PD-L1S is shown from about amino acid 19 to about amino acid 134 and the IgV domain of PD-L1M is shown from about amino acid 19 to about amino acid 134. The IgC domain of PD-L1S is shown from about amino acid 135 to about amino acid 227 and the IgC domain of PD-L1M is shown from about amino acid 135 to about amino acid 227. The hydrophilic tail of PD-L1S exemplified in Table 2 comprises a hydrophilic tail shown from about amino acid 228 to about amino acid 245. The PD-L1M exemplified in Table 2 comprises a transmembrane domain shown from about amino acids 239 to about amino acid 259 and a cytoplasmic domain shown from about amino acid 260 to about amino acid 290. In addition, nucleic acid and polypeptide sequences of PD-L1 orthologs in organisms other than humans are well known and include, for example, mouse PD-L1 (NM_021893.3 and NP_068693.1), rat PD-L1 (NM_001191954.1 and NP_001178883.1), dog PD-L1 (XM_541302.3 and XP_541302.3), cow PD-L1 (NM_001163412.1 and NP_001156884.1), and chicken PD-L1 (XM_424811.3 and XP_424811.3).

Isolated monoclonal antibodies or fragments thereof that are directed against PD-L1 are provided. In particular, the inventors have deposited the mAb 405.9A11 (i.e., the 9A11 antibody) producing hybridoma at the American Type Culture Collection (ATCC), in accordance with the terms of Budapest Treaty, as hybridoma 405.1.9A11.2D6.3.5 on Apr. 26, 2018, under deposit number PTA-124921.

The variable domain of the light and heavy chains of the 9A11 mAb have been sequenced and the complementarity determining regions (CDRs) domains thereof are provided herein and in Table 1. For example, the 9A11 light chain variable (vK) polypeptide sequence, including the signal sequence (shown in bold, highlighted text), is (SEQ ID NO: 2)
MRCLVQFLGLLVLWIPGSTADIVMTQAAFSNPVTLGTSASISCRSSKS

LLHSNGITYLYWYLQKPGQSPQLLIYQMSNLASGVPDRFSGSGSGTDF

TLRISRVEAEDVGVYYCAQNLEPPLTFGAGTKLELK, wherein CDR definitions and protein sequence numbering are listed according to Kabat nomenclature and CDR amino acid sequences are underlined in order of CDR1, CDR2, and CDR3, respectively. Thus, the light chain variable CDR 1 (CDR-L1) is RSSKSLLHSNGITYLY (SEQ ID NO: 7), CDR-L2 is QMSNLAS (SEQ ID NO: 10), and CDR-L3 is AQNLEPPLT (SEQ ID NO: 13). The 9A11 signal (shown in bold, highlighted text) and light chain variable (vK) polypeptide sequence is encoded by the following nucleic acid sequence:

(SEQ ID NO: 3)
```
  1 atgaggtgcc ttgttcagtt tctggggctg cttgtgctct ggatccctgg atccactgca 61 gatattgtga tgacgcaggc tgcattctcc aatccagtca ctcttggaac atcagcttcc 121 atctcctgca ggtccagtaa gagtctccta catagtaatg gcatcactta tttgtattgg 181 tatctgcaga agccaggcca gtctcctcag ctcctgattt atcagatgtc caaccttgcc 241 tcaggagtcc cagacaggtt cagtggcagt gggtcaggaa ctgatttcac actgagaatc 301 agcagagtgg aggctgagga tgtgggtgtt tattactgtg ctcaaaatct agaacctccg 361 ctcacgttcg gtgctgggac caagctggag ctgaaa
```

Similarly, the 9A11 heavy chain variable (vH) polypeptide sequence, including the signal sequence (shown in bold, highlighted text), is (SEQ ID NO: 15)
MKCSWVIVFLMAVVIGINSEVQLQQSGAELVRSGASVKLSCTAFGLNI

KDYYIHWVKQRPEQGLEWIGWIDPENGKTAYAPKFQGKATLTAYTSSD

TAYLHLSSLTSEDTAVYYCKTGGYDVYFLDYWGQGTSVTVSS, wherein, CDR definitions and protein sequence numbering are listed according to Kabat nomenclature and CDR amino acid sequences are underlined in order of CDR1, CDR2, and CDR3, respectively. Thus, (SEQ ID NO: 20)
CDR-H1 is DYYIH, (SEQ ID NO: 23)
CDR-H2 is WIDPENGKTAYAPKFQG,
and (SEQ ID NO: 26)
CDR-H3 is GGYDVYFLDY.

The 9A11 signal (shown in bold, highlighted text) and heavy chain variable (vH) polypeptide sequence is encoded by the following nucleic acid sequence:

(SEQ ID NO: 16)
```
  1 atgaaatgca gctgggtcat cgtcttcctg atggcagtgg ttataggaat caattcagag 61 gttcagctgc agcagtctgg ggcagagctt gtgaggtcag gggcctcagt caagttgtcc 121 tgcacagctt ttggcctcaa cattaaagac tactatatac actgggtaaa acagaggcct 181 gaacagggcc tggagtggat tggatggatt gatcctgaga tggtaaaac tgcatatgcc 241 ccgaagttcc agggcaaggc cactctgact gcatacacgt cctccgacac agcctacctg 301 cacctcagca gcctgacatc tgaggacact gccgtctatt actgtaagac tggtggttac 361 gacgtctatt ttctggacta ctggggtcaa ggaacctcag tcaccgtctc ctca
``` the present invention (e.g., including the sequences of Table 1, or portions thereof). The antibodies further can comprise the CDR2s of variable regions of the present invention (e.g., including the sequences of Table 1, or portions thereof). The antibodies further can comprise the CDR1s of variable regions of the present invention (e.g., including the sequences of Table 1, or portions thereof). In other embodiments, the antibodies can comprise any combinations of the CDRs.

The CDR1, 2, and/or 3 regions of the engineered antibodies described above can comprise the exact amino acid sequence(s) as those of variable regions of the present invention (e.g., including the sequences of Table 1, or portions thereof) disclosed herein. However, the ordinarily skilled artisan will appreciate that some deviation from the exact CDR sequences may be possible while still retaining the ability of the antibody to bind PD-L1 effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention (e.g., including the sequences of Table 1, or portions thereof).

The structural features of known, non-human or human antibodies (e.g., a mouse anti-human PD-L1 antibody) can be used to create structurally related human anti-human PD-L1 antibodies that retain at least one functional property of the antibodies of the present invention, such as binding the cytoplasmic domain of PD-L1. Another functional property includes inhibiting binding of the original known, non-human or human antibodies in a competition ELISA assay.

Since it is well known in the an that antibody heavy and light chain CDR3 domains play a particularly important role in the binding specificity/affinity of an antibody for an antigen, the recombinant monoclonal antibodies of the present invention prepared as set forth above preferably comprise the heavy and light chain CDR3s of variable regions of In some embodiments, monoclonal antibodies capable of binding the cytoplasmic domain of human PD-L1 are provided, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented in Table 1.

Similarly, monoclonal antibodies capable of binding the cytoplasmic domain of human PD-L1, comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented in Table 1, are also provided.

Monoclonal antibodies capable of binding the cytoplasmic domain of human PD-L1, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented in Table 1; and comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented in Table 1, are also provided.

A skilled artisan will note that such percentage homology is equivalent to and can be achieved by introducing 1, 2, 3, 4, 5, 6, 7, 8, 9, 10, or more conservative amino acid substitutions within a given CDR.

The monoclonal antibodies of the present invention can comprise a heavy chain, wherein the variable domain comprises at least a CDR having a sequence selected from the group consisting of the heavy chain variable domain CDRs presented in Table 1 and a light chain, wherein the variable domain comprises at least a CDR having a sequence selected from the group consisting of the light chain variable domain CDRs presented in Table 1.

Such monoclonal antibodies can comprise a light chain, wherein the variable domain comprises at least a CDR having a sequence selected from the group consisting of CDR-L1, CDR-L2, and CDR-L3, as described herein; and/or a heavy chain, wherein the variable domain comprises at least a CDR having a sequence selected from the group consisting of CDR-H1, CDR-H2, and CDR-H3, as described herein. In some embodiments, the monoclonal antibodies capable of binding the cytoplasmic domain of human PD-L1 comprises or consists of CDR-L1, CDR-L2, CDR-L3, CDR-H1, CDR-H2, and CDR-H3, as described herein.

The heavy chain variable domain of the monoclonal antibodies of the present invention can comprise or consist of the vH amino acid sequence set forth in Table 1 and/or the light chain variable domain of the monoclonal antibodies of the present invention can comprise or consist of the vκ amino acid sequence set forth in Table 1.

The monoclonal antibodies of the present invention can be produced and modified by any technique well known in the art. For example, such monoclonal antibodies can be murine antibodies, such as those obtainable from hybridoma 405.1.9A11.2D6.3.5 deposited on Apr. 26, 2018 with the ATCC as deposit number PTA-124921. Similarly, such monoclonal antibodies can be chimeric, preferably chimeric mouse/human antibodies. In some embodiments, the monoclonal antibodies are humanized antibodies such that the variable domain comprises human acceptor frameworks regions, and optionally human constant domain where present, and non-human donor CDRs, such as mouse CDRs as defined above.

The present invention further provides fragments of said monoclonal antibodies which include, but are not limited to, Fv, Fab, F(ab')2, Fab', dsFv, scFv, sc(Fv)2 and diabodies; and multispecific antibodies formed from antibody fragments. For example, a number of immunoinhibitory molecules, such as PD-L2, PD-1, CTLA-4, and the like, can be detected in a bispecific or multispecific manner in order to efficiently characterize the expression of such molecules.

Other fragments of the monoclonal antibodies of the present invention are also contemplated. For example, individual immunoglobulin heavy and/or light chains are provided, wherein the variable domains thereof comprise at least a CDR presented in Table 1. In one embodiment, the immunoglobulin heavy chain comprises at least a CDR having a sequence that is at least 80%, 85%, 90%, 91%, 92%, 93%, 94%, 95%, 96%, 97%, 98%, 99%, 99.5% or 100% identical from the group of heavy chain or light chain variable domain CDRs presented in Table 1. In another embodiment, an immunoglobulin light chain comprises at least a CDR having a sequence that is at least 80%, 85%, 90%, 91%, 92%, 93%, 94%, 95%, 96%, 97%, 98%, 99%, 99.5% or 100% identical from the group of light chain or heavy chain variable domain CDRs described herein (e.g., presented in Table 1), are also provided.

In some embodiments, the immunoglobulin heavy and/or light chain comprises a variable domain comprising at least one of CDR-L1, CDR-L2, CDR-L3, CDR-H1, CDR-H2, or CDR-H3 described herein. Such immunoglobulin heavy chains can comprise or consist of at least one of CDR-H1, CDR-H2, and CDR-H3. Such immunoglobulin light chains can comprise or consist of at least one of CDR-L1, CDR-L2, and CDR-L3.

In other embodiments, an immunoglobulin heavy and/or light chain according to the present invention comprises or consists of a vH or vκ variable domain sequence, respectively, provided in Table 1.

The present invention further provides polypeptides which have a sequence selected from the group consisting of vH variable domain, vie variable domain, CDR-L1, CDR-L2, CDR-L3, CDR-H1, CDR-H2, and CDR-H3 sequences described herein.

Antibodies, immunoglobulins, and polypeptides of the invention can be use in an isolated (e.g., purified) form or contained in a vector, such as a membrane or lipid vesicle (e.g. a liposome).

III. Nucleic Acids. Vectors, and Recombinant Host Cells

A further object of the invention relates to nucleic acid sequences encoding monoclonal antibodies and fragments thereof, immunoglobulins, and polypeptides of the present invention.

In a particular embodiment, the invention relates to a nucleic acid sequence encoding the vii domain of mAb 9A11 or the vL domain of mAb 9A11.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Thus, a further object of the invention relates to a vector comprising a nucleic acid of the present invention.

Such vectors may comprise regulatory elements, such as a promoter, enhancer, terminator and the like, to cause or direct expression of said polypeptide upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used. Examples of suitable vectors include pAGE107 (Miyaji H et al. 1990), pAGE103 (Mizukami T et al. 1987), pHSG274 (Brady G et al. 1984), pKCR(O'Hare K et al. 1981), pSG1 beta d2-4-(Miyaji H et al. 1990) and the like. Other representative examples of plasmids include replicating plasmids comprising an origin of replication, or integrative plasmids, such as for instance pUC, pcDNA, pBR, and the like. Representative examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv-positive cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516. U.S. Pat. No. 4,861,719, U.S. Pat. No. 5,278,056 and WO 94/19478.

A further object of the present invention relates to a cell which has been transfected, infected or transformed by a nucleic acid and/or a vector according to the invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed."

The nucleic acids of the present invention may be used to produce a recombinant polypeptide of the invention in a suitable expression system. The term "expression system" means a host cell and compatible vector under suitable conditions, e.g. for the expression of a protein coded for by foreign DNA carried by the vector and introduced to the host cell.

Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL 1662, hereinafter referred to as "YB2/0 cell"), and the like. The YB2/0 cell is preferred, since ADCC activity of chimeric or humanized antibodies is enhanced when expressed in this cell.

The present invention also relates to a method of producing a recombinant host cell expressing an antibody or a polypeptide of the invention according to the invention, said method comprising the steps consisting of (i) introducing in vivo or ex vivo a recombinant nucleic acid or a vector as described above into a competent host cell, (ii) culturing in vitro or ex vivo the recombinant host cell obtained and (iii), optionally, selecting the cells which express and/or secrete said antibody or polypeptide. Such recombinant host cells can be used for the production of antibodies and polypeptides of the invention.

In another aspect, the present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library. Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences. Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

IV. Methods of Producing Antibodies

Antibodies and fragments thereof, immunoglobulins, and polypeptides of the present invention may be produced by any technique known in the art, such as, without limitation, any chemical, biological, genetic or enzymatic technique, either alone or in combination.

Knowing the amino acid sequence of the desired sequence, one skilled in the art can readily produce said antibodies or polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies and other polypeptides of the present invention can be synthesized by recombinant DNA techniques as is well-known in the art. For example, these fragments can be obtained as DNA expression products after incorporation of DNA sequences encoding the desired (poly) peptide into expression vectors and introduction of such vectors into suitable eukaryotic or prokaryotic hosts that will express the desired polypeptide, from which they can be later isolated using well-known techniques.

In particular, the present invention further relates to a method of producing an antibody or a polypeptide of the invention, which method comprises the steps consisting of:

(i) culturing a transformed host cell according to the invention under conditions suitable to allow expression of said antibody or polypeptide; and (ii) recovering the expressed antibody or polypeptide.

Antibodies and other polypeptides of the present invention are suitably separated from the culture medium by conventional immunoglobulin purification procedures such as, for example, protein A-Sepharose, hydroxylapatite chromatography, gel electrophoresis, dialysis, affinity chromatography, ammonium sulfate or ethanol precipitation, acid extraction, anion or cation exchange chromatography, phosphocellulose chromatography, hydrophobic interaction chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Chimeric antibodies (e.g., mouse-human chimeras) of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. The CH domain of a human chimeric antibody can be any region which belongs to human immunoglobulin, such as the IgG class or a subclass thereof, such as IgG1, IgG2, IgG3 and IgG4. Similarly, the CL of a human chimeric antibody can be any region which belongs to Ig, such as the kappa class or lambda class, chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. Humanized antibodies of the present invention can be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell. The humanized antibody expression vector may be either of a type in which a gene encoding an antibody heavy chain and a gene encoding an antibody light chain exists on separate vectors or of a type in which both genes exist on the same vector (tandem type).

Methods for producing humanized antibodies based on conventional recombinant DNA and gene transfection techniques are well known in the art (See, e.g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

Similarly, bispecific or multispecific antibodies described herein can be made according to standard procedures. For example, triomas and hybrid hybridomas are two examples of cell lines that can secrete bispecific or multispecific antibodies. Examples of bispecific and multispecific antibodies produced by a hybrid hybridoma or a trioma are disclosed in U.S. Pat. No. 4,474,893. Such antibodies can also be constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Alternatively, such antibodiescan also be generated by making heterohybridoma by fusing hybridomas or other cells making different antibodies, followed by identification of clones producing and co-assembling the desired antibodies. They can also be generated by chemical or genetic conjugation of complete immunoglobulin chains or portions thereof such as Fab and Fv sequences. The antibody component can bind to a polypeptide or a fragment thereof of one or more biomarkers of the invention, including one or more immunoinhibitory biomarkers described herein.

In addition, methods for producing antibody fragments are well known. For example. Fab fragments of the present invention can be obtained by treating an antibody which specifically reacts with the cytoplasmic domain of human PD-L1 with a protease, papaine. Also, Fabs can be produced by inserting DNA encoding Fabs of the antibody into a vector for prokaryotic expression system, or for eukaryotic expression system, and introducing the vector into a procaryotes or eukaryote (as appropriate) to express the Fabs.

Similarly, F(ab')2 fragments of the present invention can be obtained treating an antibody which specifically reacts with the cytoplasmic domain of PD-L1 with a protease, pepsin. Also, the F(ab')2 fragment can be produced by binding Fab' described below via a thioether bond or a disulfide bond.

Fab' fragments of the present invention can be obtained treating F(ab')2 which specifically reacts with the cytoplasmic domain of human PD-L1 with a reducing agent, dithiothreitol. Also, the Fab' fragments can be produced by inserting DNA encoding a Fab' fragment of the antibody into an expression vector for prokaryote, or an expression vector for eukaryote, and introducing the vector into a prokaryote or eukaryote (as appropriate) to perform its expression.

In addition, scFvs of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. No. 5,859,205; U.S. Pat. No. 5,585,089; U.S. Pat. No. 4,816,567; EP0173494).

V. Modification of Antibodies, Immunoglobulins, and Polypeptides

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Modifications and changes may be made in the structure of the antibodies of the present invention, and in the DNA sequences encoding them, and still obtain a functional molecule that encodes an antibody and polypeptide with desirable characteristics. For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

In one embodiment, amino acid changes may be achieved by changing codons in the DNA sequence to encode conservative substitutions based on conservation of the genetic code. Specifically, there is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, CCC, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, TTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (<RTI 3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Other modifications can involve the formation of immunoconjugates. For example, in one type of covalent modification, antibodies or proteins are covalently linked to one of a variety of non proteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

Conjugation of antibodies or other proteins of the present invention with heterologous agents can be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6 diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features antibodies that specifically bind the cytoplasmic domain of PD-L1 conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a related disorder, such as a cancer.

Conjugated anti-PD-L1 antibodies can be used diagnostically or prognostically to monitor polypeptide levels in tissue as part of a clinical testing procedure, e.g., to determine the efficacy of a given treatment regimen or to select patients most likely to response to an immunotherapy. For example, cells can be permeabilized in a flow cytometry assay to allow antibodies that bind the cytoplasmic domain of PD-L1 to target its recognized intracellular epitope and allow detection of the binding by analyzing signals emanating from the conjugated molecules. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}$I, $^{131}$I, $^{35}$S, or $^{3}$H. [0134] As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or indocyanine (Cy5)) to the antibody, as well as indirect labeling of the antibody by reactivity with a detectable substance.

The antibody conjugates of the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-.gamma.; or, biological response modifiers such as, for example, lymphokines, interleukin-1 ("IL-L1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss. Inc. 1985); Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy. Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

In some embodiments, conjugations can be made using a "cleavable linker" facilitating release of the cytotoxic agent or growth inhibitory agent in a cell. For example, an acid-labile linker, peptidase-sensitive linker, photolabile linker, dimethyl linker or disulfide-containing linker (See e.g. U.S. Pat. No. 5,208,020) may be used. Alternatively, a fusion protein comprising the antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

VI. Uses and Methods of the Invention

The anti-PD-L1 antibodies, immunoglobulins, polypeptides, and nucleic acids of the present invention described herein can be used in numerous predictive medicine assays (e.g., diagnostic assays, prognostic assays, and monitoring clinical trials) based on detection of PD-L1 expression and, in some embodiments and can be useful for therapeutic purposes (e.g., therapeutic and prophylactic) either alone or when conjugated to toxic compounds or other therapeutics. The term "detection" as used herein includes qualitative and/or quantitative detection (measuring levels) with or without reference to a control. As described herein, a PD-L1 polypeptide or fragment thereof of the present invention has one or more of the following activities: 1) binds to and/or modulates the activity of its natural binding partner(s), such as PD-1 or B7-1; 2) modulates intra- or intercellular signaling, such as co-immunoinhibitory signaling; 3) modulates activation and/or proliferation of lymphocytes; 4) modulates the immune response of an organism, e.g., a mammalian organism, such as a mouse or human: and 5) modulates immune cell anergy.

Thus, one aspect of the present invention relates to diagnostic assays for determining PD-L1 polypeptide expression in the context of a biological sample (e.g., blood, serumn, cells, or tissue) to thereby determine the level of PD-L1 polypeptide in the sample, to determine whether an individual is afflicted with a disorder and/or to determine the state of such a disorder, indicated by such PD-L1 levels. For example, antibodies of the present invention are useful for staging cancer diseases associated with aberrant PD-L1 expression.

The present invention also provides for prognostic (or predictive) assays for determining whether an individual is at risk of developing such a disorder. Another aspect of the present invention pertains to monitoring the influence of agents (e.g., drugs, compounds) on the expression or activity of PD-L1 in clinical trials.

In any method described herein, PD-L1 expression can be detected either alone or in combination with the expression of other molecules, such as other immune checkpoint and/or costimulatory molecules. Combinatorial detection (e.g., sequentially or simultaneously) of several molecules can provide useful information regarding synergies of therapeutic intervention and/or personalized, higher-resolution diagnoses of disorder subtypes. In some embodiments, PD-L1 is combinatorially detected with one more markers selected from the group consisting of immune checkpoint including, without limitation. CTLA-4, PD-1, VISTA, B7-H2, B7-H3, PD-L1, B7-H4, B7-H6, 2B4, ICOS, HVEM, PD-L2, CD160, gp49B, PIR-B, KIR, TIM-3, LAG-3, HHLA2, butyrophilins, and BTLA (see, for example, WO 2012/177624). In some embodiments, PD-L1 is combinatorially detected with one or more markers selected from the group consisting of costimulatory molecules, such as B7-1, B7-2, CD28, and the like.

1. Diagnostic Assays

The Present Invention Provides, in Part, Methods, Systems, and Code for Accurately classifying whether a biological sample expresses cell-restricted PD-L1 and/or whether the levels of cell-restricted PD-L1 are modulated (e.g., upregulated or downregulated), thereby indicative of the state of a disorder of interest, such as cancer. In some embodiments, the present invention is useful for classifying a sample (e.g., from a subject) as associated with or at risk for cancer or a subtype thereof, mediated by PD-L1 (known as a PD-L1 sample and) using a statistical algorithm and/or empirical data (e.g., the presence, absence, or level of PD-L1).

An exemplary method for detecting the level of expression or activity of PD-L1 or fragments thereof, and thus useful for classifying whether a sample is associated with a disease or disorder mediated by PD-L1 or a clinical subtype thereof involves obtaining a biological sample from a test subject and contacting the biological sample with an antibody or antigen-binding fragment thereof of the present invention capable of detecting PD-L1 such that the level of expression or activity of PD-L1 is detected in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a PD-L1 sample based upon a prediction or probability value and the presence or level of PD-L1. The use of a single learning statistical classifier system typically classifies the sample as a PD-L1 sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetiet algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the PD-L1 sample classification results to a clinician, e.g., a histopathologist or an oncologist.

In another embodiment, the method of the present invention further provides a diagnosis in the form of a probability that the individual has a condition or disorder associated with aberrant expression or activity of PD-L1. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having the condition or disorder. In yet another embodiment, the method of the present invention further provides a prognosis of the condition or disorder in the individual. In some instances, the method of classifying a sample as a PD-L1 sample is further based on the symptoms (e.g., clinical factors) of the individual from which the sample is obtained. The symptoms or group of symptoms can be, for example, lymphocyte count, white cell count, erythrocyte sedimentation rate, diarrhea, abdominal pain, cramping, fever, anemia, weight loss, anxiety, depression, and combinations thereof. In some embodiments, the diagnosis of an individual as having a condition or disorder associated with aberrant expression or activity of PD-L1 is followed by administering to the individual a therapeutically effective amount of a drug useful for treating one or more symptoms associated with the condition or disorder (e.g., chemotherapeutic agents).

In one embodiment, the methods further involve obtaining a control biological sample (e.g., biological sample from a subject who does not have a condition or disorder mediated by PD-L1), a biological sample from the subject during remission or before developing a condition or disorder mediated by PD-L1, or a biological sample from the subject during treatment for developing a condition or disorder mediated by PD-L1.

An exemplary method for detecting the presence or absence of PD-L1 polypeptide or fragments thereof is an antibody of the present invention, or fragment thereof, capable of binding to a PD-L1 polypeptide, preferably an antibody with a detectable label. Antibodies can be polyclonal, or more preferably, monoclonal. Such agents can be labeled. The term "labeled", with regard to the antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody. The term "biological sample" is intended to include tissues, cells, and biological fluids isolated from a subject, such as serum, as well as tissues, cells, and fluids present within a subject. That is, the detection method of the present invention can be used to detect PD-L1, or fragments thereof, in a biological sample in vitro as well as in vivo. In vitro techniques for detection of PD-L1 polypeptide include enzyme linked immunosorbent assays (ELISAs), Western blots, immunoprecipitations, immunohistochemistry (IHC), intracellular flow cytometry and related techniques, and immunofluorescence. Furthermore, in vivo techniques for detection of a PD-L1 polypeptide or a fragment thereof include introducing into a subject a labeled anti-PD-L1 antibody. For example, the antibody can be labeled with a radioactive, luminescent, fluorescent, or other similar marker whose presence and location in a subject can be detected by standard imaging techniques, either alone or in combination with imaging for other molecules, such as markers of cell type (e.g., CD8+ T cell markers).

In one embodiment, the biological sample contains polypeptide molecules from the test subject. A preferred biological sample is a serum, tumor microenvironment, peritumoral, or intratumoral, isolated by conventional means from a subject.

In another embodiment, the methods further involve obtaining a control biological sample from a control subject, contacting the control sample with a compound or agent capable of detecting PD-L1 polypeptide, or fragments thereof, such that the presence of PD-L1 polypeptide, or fragments thereof, is detected in the biological sample, and comparing the presence of PD-L1 polypeptide, or fragments thereof, in the control sample with the presence of PD-L1 polypeptide, or fragments thereof in the test sample.

In still other embodiments, the antibodies can be associated with a component or device for the use of the antibodies in an ELISA or RIA. Non-limiting examples include antibodies immobilized on solid surfaces for use in these assays (e.g., linked and/or conjugated to a detectable label based on light or radiation emission as described above). In other embodiments, the antibodies are associated with a device or strip for detection of PD-L1 by use of an immunochromatographic or immunochemical assay, such as in a "sandwich" or competitive assay, immunohistochemistry, immunofluorescence microscopy, and the like. Additional examples of such devices or strips are those designed for home testing or rapid point of care testing. Further examples include those that are designed for the simultaneous analysis of multiple analytes in a single sample. For example, an unlabeled antibody of the invention may be applied to a "capture" PD-L1 polypeptides in a biological sample and the captured (or immobilized) PD-L1 polypeptides may be bound to a labeled form of an anti-PD-L1 antibody of the invention for detection.

Other standard embodiments of immunoassays are well known the skilled artisan, including assays based on, for example, immunodiffusion, immunoelectrophoresis, immunohistopathology, immunohistochemistry, and histopathology.

2. Prognostic Assays

The diagnostic methods described herein can furthermore be utilized to identify subjects having or at risk of developing a disorder associated with aberrant or undesired PD-L1 expression levels. As used herein, the term "aberrant" includes a PD-L1 expression or activity which deviates from the wild type or normal PD-L1 expression or activity. Aberrant expression or activity includes increased or decreased expression or activity, as well as expression or activity which does not follow the wild type developmental pattern of expression or the subcellular pattern of expression. For example, aberrant PD-L1 expression or activity is intended to include the cases in which a mutation in the PD-L1 gene or regulatory sequence, or amplification of the chromosomal PD-L1 gene, thereof causes the PD-L1 gene to be under-expressed or over-expressed and situations in which such mutations result in a non-functional PD-L1 polypeptide or a polypeptide which does not function in a wild-type fashion, e.g., a polypeptide missing an intracellular domain and thus not able to interact with a PD-L1 binding or signal partner. As used herein, the term "unwanted" includes an unwanted phenomenon involved in a biological response such as immune cell activation. For example, the term unwanted includes a PD-L1 expression or activity which is undesirable in a subject.

Many disorders associated with aberrant PD-L1 expression are known to the skilled artisan, as explained further in the Examples. PD-L1 is expressed by multiple tumor types, including select lymphoid malignancies, virally-induced cancers, and many solid tumors. Generally, PD-L1 expression is an adverse prognostic marker because it is an immune checkpoint regulator that inhibits strong immune responses against conditions in need thereof. However, immunoinhibition is desired for downregulating immune responses in treating a number of disorders, such as autoimmune diseases, inflammatory diseases, and the like.

The assays described herein, such as the preceding diagnostic assays or the following assays, can be utilized to identify a subject having or at risk of developing a disorder associated with a misregulation of PD-L1 polypeptide expression. Thus, the present invention provides a method for identifying a disorder associated with aberrant or unwanted PD-L1 expression in which a test sample is obtained from a subject and PD-L1 polypeptide is detected, wherein the presence of PD-L1 polypeptide is diagnostic for a subject having or at risk of developing the disorder associated with aberrant or unwanted PD-L1 expression or activity. As used herein, a "test sample" refers to a biological sample obtained from a subject of interest. For example, a test sample can be a biological fluid (e.g., cerebrospinal fluid or serum), cell sample, or tissue, such as a histopathological slide of the tumor microenvironment, peritumoral area, and/or intratumoral area. In a preferred embodiment, the sample comprises cells expressing mature membrane-bound PD-L1 and/or immature cytoplasmic PD-L1 containing an intracellular domain.

Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat such a disorder associated with aberrant or unwanted PD-L1 expression or activity. For example, such methods can be used to determine whether a subject can be effectively treated with one or a combination of agents. Thus, the present invention provides methods for determining whether a subject can be effectively treated with one or more agents for treating a disorder associated with aberrant or unwanted PD-L1 expression in which a test sample is obtained and PD-L1 polypeptide is detected (e.g., wherein the abundance of PD-L1 polypeptide expression is diagnostic for a subject that can be administered the agent to treat the disorder associated with aberrant or unwanted PD-L1 expression).

The methods described herein may be performed, for example, by utilizing pre-packaged diagnostic kits comprising at least one antibody reagent described herein, which may be conveniently used, e.g., in clinical settings to diagnose patients exhibiting symptoms or family history of a disease or illness involving PD-L1.

Furthermore, any cell type or tissue in which PD-L1 is expressed may be utilized in the prognostic assays described herein.

Another aspect of the present invention includes uses of the compositions and methods described herein for association and/or stratification analyses in which the expression of PD-L1 in biological samples from individuals with a disorder associated with aberrant PD-L1 expression, are analyzed and the information is compared to that of controls (e.g., individuals who do not have the disorder; controls may be also referred to as "healthy" or "normal" individuals or at early timepoints in a given time lapse study) who are preferably of similar age and race. The appropriate selection of patients and controls is important to the success of association and/or stratification studies. Therefore, a pool of individuals with well-characterized phenotypes is extremely desirable. Criteria for disease diagnosis, disease predisposition screening, disease prognosis, determining drug responsiveness (pharmacogenomics), drug toxicity screening, etc. are described herein.

Different study designs may be used for genetic association and/or stratification studies (Modern Epidemiology, Lippincott Williams & Wilkins (1998), 609-622). Observational studies are most frequently carried out in which the response of the patients is not interfered with. The first type of observational study identifies a sample of persons in whom the suspected cause of the disease is present and another sample of persons in whom the suspected cause is absent, and then the frequency of development of disease in the two samples is compared. These sampled populations are called cohorts, and the study is a prospective study. The other type of observational study is case-control or a retrospective study. In typical case-control studies, samples are collected from individuals with the phenotype of interest (cases) such as certain manifestations of a disease, and from individuals without the phenotype (controls) in a population (target population) that conclusions are to be drawn from. Then the possible causes of the disease are investigated retrospectively. As the time and costs of collecting samples in case-control studies are considerably less than those for prospective studies, case-control studies are the more commonly used study design in genetic association studies, at least during the exploration and discovery stage.

After all relevant phenotypic and/or genotypic information has been obtained, statistical analyses are carried out to determine if there is any significant correlation between the presence of an allele or a genotype with the phenotypic characteristics of an individual. Preferably, data inspection and cleaning are first performed before carrying out statistical tests for genetic association. Epidemiological and clinical data of the samples can be summarized by descriptive statistics with tables and graphs well known in the art. Data validation is preferably performed to check for data completion, inconsistent entries, and outliers. Chi-squared tests and t-tests (Wilcoxon rank-sum tests if distributions are not normal) may then be used to check for significant differences between cases and controls for discrete and continuous variables, respectively.

An important decision in the performance of genetic association tests is the determination of the significance level at which significant association can be declared when the p-value of the tests reaches that level. In an exploratory analysis where positive hits will be followed up in subsequent confirmatory testing, an unadjusted p-value <0.2 (a significance level on the lenient side), for example, may be used for generating hypotheses for significant association of a PD-L1 expression level with certain phenotypic characteristics of a disease. It is preferred that a p-value <0.05 (a significance level traditionally used in the art) is achieved in order for the level to be considered to have an association with a disease. When hits are followed up in confirmatory analyses in more samples of the same source or in different samples from different sources, adjustment for multiple testing will be performed as to avoid excess number of hits while maintaining the experiment-wise error rates at 0.05. While there are different methods to adjust for multiple testing to control for different kinds of error rates, a commonly used but rather conservative method is Bonferroni correction to control the experiment-wise or family-wise error rate (Multiple comparisons and multiple tests. Westfall et al, SAS Institute (1999)). Permutation tests to control for the false discovery rates. FDR, can be more powerful (Benjamini and Hochberg, Journal of the Royal Statistical Society, Series B 57, 1289-1300, 1995, Resampling-based Multiple Testing, Westfall and Young, Wiley (1993)). Such methods to control for multiplicity would be preferred when the tests are dependent and controlling for false discovery rates is sufficient as opposed to controlling for the experiment-wise error rates.

Once individual risk factors, genetic or non-genetic, have been found for the predisposition to disease, a classification/prediction scheme can be set up to predict the category (for instance, disease or no-disease) that an individual will be in depending on his phenotype and/or genotype and other non-genetic risk factors. Logistic regression for discrete trait and linear regression for continuous trait are standard techniques for such tasks (Applied Regression Analysis, Draper and Smith, Wiley (1998)). Moreover, other techniques can also be used for setting up classification. Such techniques include, but are not limited to, MART, CART, neural network, and discriminant analyses that are suitable for use in comparing the performance of different methods (The Elements of Statistical Learning. Hastie, Tibshirani & Friedman. Springer (2002)).

3. Monitoring of Effects During Clinical Trials

Monitoring the influence of agents (e.g., compounds, drugs or small molecules) on the expression or activity of a PD-L1 polypeptide or a fragment thereof (e.g., the modulation of cell proliferation and/or migration) can be applied not only in basic drug screening, but also in clinical trials. For example, the effectiveness of an agent determined by a screening assay as described herein to decrease PD-L1 gene expression, polypeptide levels, or downregulate PD-L1 activity, can be monitored in clinical trials of subjects exhibiting decreased PD-L1 gene expression, polypeptide levels, or downregulated PD-L1 activity. In such clinical trials, the expression or activity of a PD-L1 gene and/or symptoms or markers of the disorder of interest, can be used as a "read out" or marker of the phenotype of a particular cell, tissue, or system. Similarly, the effectiveness of an agent determined by a screening assay as described herein to increase PD-L1 gene expression, polypeptide levels, or increase PD-L1 activity, can be monitored in clinical trials of subjects exhibiting increased PD-L1 gene expression, polypeptide levels, or increased PD-L1 activity. In such clinical trials, the expression or activity of a PD-L1 gene and/or symptoms or markers of the disorder of interest, can be used as a "read out" or marker of the phenotype of a particular cell, tissue, or system, such as for an autoimmune disorder.

For example, and not by way of limitation, genes, including PD-L1, that are modulated in cells by treatment with an agent (e.g., compound, drug or small molecule) which modulates PD-L1 activity (e.g., identified in a screening assay as described herein) can be identified. Thus, to study the effect of agents on a disorder associated with aberrant PD-L1 expression, for example, in a clinical trial, cells can be isolated and nucleic acids and/or protein prepared and analyzed for the levels of expression of PD-L1 and/or other genes implicated in the disorder associated with aberrant PD-L1 expression. The levels of gene expression (e.g., a gene expression pattern) analyzed by measuring the amount of polypeptide produced, by one of the methods as described herein, or by measuring the levels of activity of PD-L1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting the level of expression of a PD-L1 polypeptide, or fragments thereof, in the preadministration sample; (iii) obtaining one or more post-administration samples from the subject; (iv) detecting the level of expression of the PD-L1 polypeptide, or fragments thereof, in the post-administration samples; (v) comparing the level of expression or activity of the PD-L1 polypeptide, or fragments thereof, in the pre-administration sample with the PD-L1 polypeptide, mRNA, or genomic DNA in the post administration sample or samples; and (vi) altering the administration of the agent to the subject accordingly. For example, increased administration of the agent may be desirable to decrease the expression or activity of PD-L1 to lower levels than detected, i.e., to increase the effectiveness of the agent. According to such an embodiment, PD-L1 expression or activity may be used as an indicator of the effectiveness of an agent, even in the absence of an observable phenotypic response. Similarly, PD-L1 expression analysis, such as by immunohistochemistry (IHC), can also be used to select patients who will receive PD-L1 and/or PD-L1 immunotherapy, or immunotherapy to inhibit one ore more immune checkpoints. Patients whose tumors express PD-L1 are more likely to respond to PD-1 or PD-L1 mAb immunotherapy, as described herein. The immunotherapy will initially result in immune activation and the activated T cells will express IFN-gamma which in turn will upregulate PD-L1 expression. Normally this would result in PD-1 engagement and down regulation of the immune response, but because PD-1 is blocked by the PD-1 mAb, the immune response continues until a desired condition, such as a tumor, is eliminated. By contrast, mAbs that actively signal through PD-1 directly downregulate an immune response.

4. Therapeutic Methods and Uses

In some embodiments, antibodies, fragments or immunoconjugates of the present invention (e.g., anti-PD-L1 antibodies alone or conjugated to therapeutic moieties) are useful for treating any disorder (e.g., a cancer) associated with aberrant or undesired expression of PD-L1. In certain embodiments, the treatment is of a mammal, such as a human. Such antibodies of the invention may be used alone or in combination with any suitable agent or appropriate therapy to treat the disorder of interest. For example, therapeutic synergies are believed to become manifested when treating a cell expressing PD-L1 and another immune checkpoint or costimulatory molecule.

It is well known that therapeutic monoclonal antibodies can lead to the depletion of cells extracellularly bearing the antigen specifically recognized by the antibody. This depletion can be mediated through at least three mechanisms: antibody mediated cellular cytotoxicity (ADCC), complement dependent lysis, and direct anti-tumour inhibition of tumour growth through signals given via the antigen targeted by the antibody.

"Complement dependent cytotoxicity" or "CDC" refers to the lysis of a target cell in the presence of complement. Activation of the classical complement pathway is initiated by the binding of the first component of the complement system to antibodies which are bound to their cognate antigen. To assess complement activation, a CDC assay, e.g. as described in Gazzano-Santoro et al. (1997) may be performed.

"Antibody-dependent cell-mediated cytotoxicity" or "ADCC" refers to a form of cytotoxicity in which secreted antibodies bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell. To assess ADCC activity of a molecule of interest, an in vitro ADCC assay, such as that described in U.S. Pat. No. 5,500,362 or 5,821,337 may be performed. As is well known in the art, the Fc portions can be engineered to effect a desired interaction or lack thereof with Fc receptors.

For antibody-mediated binding, neutralization, and/or modulation of intracellular targets, certain modifications should be made. As described herein, certain antibody formats, such as sFvs and Fabs, are amenable to intracellular expression of antibody-like molecules. Methods of making and using such adapted antibody-like molecules for targeting expression in different compartments of the cell, including the nucleus, ER, cytoplasm, golgi, plasma membrane, mitochondria, where they counteract antigens or molecules in a specific pathway, are well known (see, at least U.S. Pat. Publs. 2008-0233110 and 2003-0104402; Marasco et al. (1993) *Proc. Natl. Acad. Sci. U.S.A.* 90:7889-7893; Chen et al. (1994) *Human Gene Therapy* 5:595-601; Chen et al. (1994) *Proc. Natl. Acad. Sci. U.S.A.* 91:5932-5936; Mhashilkar et al. (1995) *EMBO J.* 14:1542-1551; Marasco et al. (1997) *Gene Therapy* 4:11-15; Richardson et al. (1995) *Proc. Natl. Acad. Si. U.S.A.* 92:3137-3141; and Duan et al. (1994) *Human Gene Therapy* 5:1315-1324).

As used herein, the term "intracellular immunoglobulin molecule" is a complete immunoglobulin which is the same as a naturally-occurring secreted immunoglobulin, but which remains inside of the cell following synthesis. An "intracellular immunoglobulin fragment" refers to any fragment, including single-chain fragments of an intracellular immunoglobulin molecule. Thus, an intracellular immunoglobulin molecule or fragment thereof is not secreted or expressed on the outer surface of the cell. Single-chain intracellular immunoglobulin fragments are referred to herein as "single-chain immunoglobulins." As used herein, the term "intracellular immunoglobulin molecule or fragment thereof" is understood to encompass an "intracellular immunoglobulin," a "single-chain intracellular immunoglobulin" (or fragment thereof), an "intracellular immunoglobulin fragment," an "intracellular antibody" (or fragment thereof), and an "intrabody" (or fragment thereof). As such, the terms "intracellular immunoglobulin," "intracellular Ig," "intracellular antibody," and "intrabody" may be used interchangeably herein, and are all encompassed by the generic definition of an "intracellular immunoglobulin molecule, or fragment thereof." An intracellular immunoglobulin molecule, or fragment thereof of the present invention may, in some embodiments, comprise two or more subunit polypeptides, e.g., a "first intracellular immunoglobulin subunit polypeptide" and a "second intracellular immunoglobulin subunit polypeptide." However, in other embodiments, an intracellular immunoglobulin may be a "single-chain intracellular immunoglobulin" including only a single polypeptide. As used herein, a "single-chain intracellular immunoglobulin" is defined as any unitary fragment that has a desired activity, for example, intracellular binding to an antigen. Thus, single-chain intracellular immunoglobulins encompass those which comprise both heavy and light chain variable regions which act together to bind antigen, as well as single-chain intracellular immunoglobulins which only have a single variable region which binds antigen, for example, a "camelized" heavy chain variable region as described herein. An intracellular immunoglobulin or Ig fragment may be expressed anywhere substantially within the cell, such as in the cytoplasm, on the inner surface of the cell membrane, or in a subcellular compartment (also referred to as cell subcompartment or cell compartment) such as the nucleus, golgi, endoplasmic reticulum, endosome, mitochondria, etc. Additional cell subcompartments include those that are described herein and well known in the art Such intracellular immunoglobulins are expressed in a recipient cell or host cell containing the antigen to be targeted. A host cell of the present invention is preferably a eukaryotic cell or cell line, preferably a plant, animal, vertebrate, mammalian, rodent, mouse, primate, or human cell or cell line.

Without being bound by theory, it is believed that intracellular expression of the immunoglobulin polypeptides described herein allow for the intracellular targeting and binding of the cytoplasmic portion of PD-L1 to thereby sterically modulate the molecule's ability to signal by, for example, modulating its ability to propagate signaling upon activation by binding to PD-1. B7-1, and the like and/or to modulate signaling upon increasing the local effective concentration of multiple PD-L1 molecules. The effects of modulating PD-L1 signaling are well known in the art (see, for example, PCT Publ. WO 2001/014557).

In some embodiments, antibodies of the present invention can be conjugated to a therapeutic moiety, such as a growth inhibitory agent, cytotoxic agent, or a prodrug-activating enzyme as previously described. Antibodies of the invention can be useful for targeting said growth inhibitory agent, cytotoxic agent, or a prodrug to a cell that under- or over-expresses the desired amount of PD-L1.

Thus, an object of the invention relates to a method for treating a disorder associated with aberrant PD-L1 expression comprising administering a subject in need thereof with a therapeutically effective amount of an antibody, fragment or immunoconjugate of the present invention.

Alternatively, in some embodiments, the antibodies or the antigen-binding fragments of the present invention are useful for therapeutic applications, in addition to diagnostic, prognostic, and prevention applications regarding upregulating an immune response. Upregulation of immune responses can be in the form of enhancing an existing immune response or eliciting an initial immune response. For instance, enhancing an immune response using the subject compositions and methods is useful in cases of improving an immunological defense against cancer and infections with microbes (e.g., bacteria, viruses, or parasites). For example, upregulation or enhancement of an immune response function, as described herein, is useful in the induction of tumor immunity. In another embodiment, the immune response can be stimulated by the methods described herein, such that preexisting tolerance, clonal deletion, and/or exhaustion (e.g., T cell exhaustion) is overcome. For example, immune responses against antigens to which a subject cannot mount a significant immune response, e.g., to an autologous antigen, such as a tumor specific antigens can be induced by administering appropriate agents described herein that upregulate the immune response. In one embodiment, an autologous antigen, such as a tumor-specific antigen, can be coadministered. In another embodiment, an immune response can be stimulated against an antigen (e.g., an autologous antigen) to treat a neurological disorder. In another embodiment, the subject agents can be used as adjuvants to boost responses to foreign antigens in the process of active immunization.

In certain instances, it may be desirable to further administer other agents that upregulate immune responses, for example, forms of other B7 family members that transduce signals via costimulatory receptors, in order to further augment the immune response. Also, agents that upregulate an immune response can be used prophylactically in vaccines against various polypeptides (e.g., polypeptides derived from pathogens). Immunity against a pathogen (e.g., a virus) can be induced by vaccinating with a viral protein along with an agent that upregulates an immune response, in an appropriate adjuvant.

Alternatively, in some embodiments, the antibodies and the antigen-binding fragments of the present invention are useful for therapeutic applications, in addition to diagnostic, prognostic, and prevention applications (such as treating, and delaying the onset or progression of the diseases), to inhibit diseases that upregulate the immune reaction, for example, asthma, autoimmune diseases (glomerular nephritis, arthritis, dilated cardiomyopathy-like disease, ulcerous colitis, Sjogren syndrome, Crohn disease, systemic erythematodes, chronic rheumatoid arthritis, multiple sclerosis, psoriasis, allergic contact dermatitis, polymyosiis, pachyderma, periarteritis nodosa, rheumatic fever, vitiligo vulgaris, insulin dependent diabetes mellitus, Behcet disease, Hashimoto disease, Addison disease, dermatomyositis, myasthenia gravis, Reiter syndrome, Graves' disease, anaemia perniciosa, Goodpasture syndrome, sterility disease, chronic active hepatitis, pemphigus, autoimmune thrombopenic purpura, and autoimmune hemolytic anemia, active chronic hepatitis, Addison's disease, anti-phospholipid syndrome, atopiet allergy, autoimmune atrophic gastritis, achlorhydra autoimmune, celiac disease, Cushing's syndrome, dermatomyositis, discoid lupus, erythematosis, Goodpasture's syndrome, Hashimoto's thyroiditis, idiopathic adrenal atrophy, idiopathic thrombocytopenia, insulin-dependent diabetes, Lambert-Eaton syndrome, lupoid hepatitis, some cases of lymphopenia, mixed connective tissue disease, pemphigoid, pemphigus vulgaris, pernicious anema, phacogenic uveitis, polyarteritis nodosa, polyglandular autosyndromes, primary biliary cirrhosis, primary sclerosing cholangitis, Raynaud's syndrome, relapsing polychondritis, Schmidt's syndrome, limited scleroderma (or crest syndrome), sympathetic ophthalmia, systemic lupus erythematosis. Takayasu's arteritis, temporal arteritis, thyrotoxicosis, type b insulin resistance, ulcerative colitis and Wegener's granulomatosis).

Similarly, the antibodies and the antigen-binding fragments of the present invention are useful for therapeutic applications, in addition to diagnostic, prognostic, and prevention applications (such as treating, and delaying the onset or progression of the diseases) for persistent infectious disease (e.g., viral infectious diseases including HPV, HBV, hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, and influenza virus. Other antigens associated with pathogens that can be used as described herein are antigens of various parasites, includes malaria, preferably malaria peptide based on repeats of NANP. In addition, bacterial, fungal and other pathogenic diseases are included, such as *Aspergillus, Brugia, Candida, Chlamydia, Coccidia, Cryptococcus, Dirofilaria, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma* and *Vibriocholerae*. Exemplary species include *Neisseria gonorrhea, Mycobacterium tuberculosis. Candida albicans. Candida tropicalis, Trichomonas vaginalis, Haemophilus vaginalis*. Group B *Streptococcus* sp., *Microplasma hominis. Hemophilus ducreyi, Granuloma inguinale, Lymphopathia venereum, Treponema pallidum, Brucella abortus. Brucella melitensis, Brucella suis, Brucella canis, Campylobacter fetus, Campylobacter fetus intestinalis, Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Coryne-*

*bacterium pyogenes, Actinobaccilus seminis, Mycoplasma bovigenitalium, Aspergillus fumigatus, Absidia ramosa, Trypanosoma equiperdum, Babesia caballi, Clostridium tetani, Clostridium botulinum*; or, a fungus, such as, e.g., *Paracoccidioides brasiliensis*; or other pathogen, e.g., *Plasmodium falciparum*. Also included are National Institute of Allergy and Infectious Diseases (NIAID) priority pathogens. These include Category A agents, such as variola major (smallpox), *Bacillus anthracis* (anthrax), *Yersinia pestis* (plague), *Clostridium botulinum* toxin (botulism), *Francisella tularensis* (tularacmia), filoviruses (Ebola hemorrhagic fever, Marburg hemorrhagic fever), arenaviruses (Lassa (Lassa fever), Junin (Argentine hemorrhagic fever) and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphylococcus* enterotoxin B, *Salmonella* species, *Shigella dysenteriae, Escherichia coli* strain O157:H7, *Vibrio cholerae, Cryptosporidium parvum*; Category C agents, such as nipah virus, hantaviruses, tickborne hemorrhagic fever viruses, tickborne encephalitis viruses, yellow fever, and multidrug-resistant tuberculosis; helminths, such as *Schistosoma* and *Taenia*; and protozoa, such as *Leishmania* (e.g., *L. mexicana*) and *Plasmodium.*

In still another embodiment, the antibodies or the antigen-binding fragments of the present invention are useful for therapeutic applications, in addition to diagnostic, prognostic, and prevention applications regarding induction of immunological tolerance, organ graft rejection, graft-versus-host disease (GVHD), allergic disease, and diseases caused by attenuation of immune reactions mediated by PD-L1.

In the context of the invention, the term "treating" or "treatment", as used herein, means reversing, alleviating, inhibiting the progress of, or preventing the disorder or condition to which such term applies, or one or more symptoms of such disorder or condition. By the term "treating cancer" as used herein is meant the inhibition of the growth and/or proliferation of cancer cells. Preferably such treatment also leads to the regression of tumor growth (i.e., the decrease in size of a measurable tumor). Most preferably, such treatment leads to the complete regression of the tumor.

In some embodiments, the term "patient" or "patient in need thereof" is intended for a human or non-human mammal affected or likely to be affected with a cancer associated with aberrant expression of PD-L1.

By a "therapeutically effective amount" of the polypeptide of the invention is meant a sufficient amount of the antibody to treat the disorder of interest, such as cancer, at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved.

Therapeutic formulations comprising one or more antibodies of the invention are prepared for storage by mixing the antibody having the desired degree of purity with optional physiologically acceptable carriers, excipients or stabilizers (Remington's Pharmaceutical Sciences 16th edition. Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The therapeutic dose can be at least about 0.01 μg/kg body weight, at least about 0.05 μg/kg body weight; at least about 0.1 g/kg body weight, at least about 0.5 μg/kg body weight, at least about 1 μg/kg body weight, at least about 2.5 μg/kg body weight, at least about 5 μg/kg body weight, and not more than about 100 μg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g. i.m., i.p., i.v., and the like.

The composition need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules)

or in macroemulsions. Such techniques are disclosed in Remington's Pharmaceutical Sciences 16th edition, Osol, A. Ed. (1980).

The compositions described herein can be administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the compositions can be suitably administered by pulse infusion, particularly with declining doses of the antibody.

For the prevention or treatment of disease, the appropriate dosage of antibody will depend on the type of disease to be treated, as defined above, the severity and course of the disease, whether the antibody is administered for preventive purposes, previous therapy, the patient's clinical history and response to the antibody, and the discretion of the attending physician. The antibody is suitably administered to the patient at one time or over a series of treatments.

VII. Kits

In addition, the present invention also encompasses kits for detecting the presence of a membrane-bound PD-L1 polypeptide, or fragments thereof, in a biological sample. For example, the kit can comprise a labeled compound or agent capable of detecting a membrane-bound PD-L1 polypeptide, or fragments thereof, in a biological sample; means for determining the amount of the membrane-bound PD-L1 polypeptide, or fragments thereof, in the sample; and means for comparing the amount of the membrane-bound PD-L1 polypeptide, or fragments thereof, in the sample with a standard. The compound or agent can be packaged in a suitable container. For example, the present invention provides kits comprising at least one antibody described herein. Kits containing antibodies of the invention find use in detecting expression of membrane-bound PD-L1, or in therapeutic or diagnostic assays. Kits of the invention can contain an antibody coupled to a solid support, e.g., a tissue culture plate or beads (e.g., sepharose beads).

A kit can include additional components to facilitate the particular application for which the kit is designed. For example, kits can be provided which contain antibodies for detection and quantification of membrane-bound PD-L1 in vitro, e.g. in an ELISA or a Western blot. Additional, exemplary agents that kits can contain include means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or PD-L1 protein standards). A kit may additionally include buffers and other reagents recognized for use in a method of the disclosed invention. Non-limiting examples include agents to reduce non-specific binding, such as a carrier protein or a detergent. A kit of the present invention can also include instructional materials disclosing or describing the use of the kit or an antibody of the disclosed invention in a method of the disclosed invention as provided herein.

This invention is further illustrated by the following examples which should not be construed as limiting. The contents of all references, patents and published patent applications cited throughout this application, as well as the Figures, are incorporated herein by reference.

EXAMPLES

Example 1: Anti-PD-L1 Monoclonal Antibodies that Target the PD-L1 Cytoplasmic Domain The Programmed death-1, PD-1, pathway is a critical immune checkpoint pathway involved in peripheral toler-ance. PD-1 is a B7/CD28 superfamily receptor expressed on activated and exhausted T cells, as well as some activated B cells, dendritic cells, and monocytes. PD-1 negatively regulates lymphocyte function through signaling triggered by the interaction with its ligands, PD-L1 and PD-L2 (Brown et al. (2003) *J. Immunol.* 170:1257-1266; Freeman et al. (2000) *J. Exp. Med.* 192:1027-1034; Latchman et al. (2001) *Nat. Immunol.* 2:261-268). The PD-1 pathway downregulates the intensity and duration of immune responses. PD-L1 is expressed on many hematologic cells including dendritic cells, macrophages, mesenchymal stem cells, and bone-marrow derived mast cells (Yamazaki et al. (2002) *J. Immunol.* 169:5538-5545) and is induced on activated T cells and macrophages. PD-L1 can be inducibly expressed on epithelial and endothelial cells by interferons and is constitutively expressed on some sites of immune privilege such as syncytiotrophoblast and retina. Expression of PD-L1 on non-hematologic cells plays a role in peripheral tolerance of T cells (Keir et al. (2006) *J. Exp. Med.* 203:883-895). There is also opportunity for cross talk between the PD-L1 receptor and its ligands in the hematologic compartment, such as PD-L1 on tolerogenic dendritic cells inducing T cell tolerance within the lymph node (Sharpe et al. (2007) *Nat. Immunol.* 8:239-245).

Therapeutic blockade of either PD-1 or PD-L1 produces impressive antitumor responses in Phase I, II, and III clinical trials in many different tumors. This has led to US FDA approval of pembrolizumab for melanoma and breakthrough designation of nivolumab for Hodgkin Lymphoma and MPDL3280A for bladder cancer (Topalian et al. (2012) *N. Engl. J. Med.* 366:2443-2454; Brahmer et al. (2012) *N. Engl. J. Med.* 366:2455-2465; Hamid et al. (2013) *N. Engl. J. Med.* 369:134-144; Hamid et al. (2013) *J. Clin. Oncol.* 31(supp): abstract 9010). Many tumors have increased expression of PD-L1, in addition to Hodgkin lymphoma, melanoma, and bladder cancer, including renal cell, nasopharyngeal, ovarian and breast carcinoma (Latchman et al. (2001) *Nat. Immunol.* 2:261-268; Iwai et al. (2002) *Proc. Natl. Acad. Sci. U.S.A.* 99:12293-12297; Green et al. (2010) *Blood* 116:3268-3277). PD-L1 can be constitutively expressed on epithelial and hematopoietic tumor cells as a consequence of oncogenic changes and can also be induced by interferons. Expression of PD-L1 on tumors facilitates immune evasion and also increases tumorigenesis and invasiveness in vivo. In some tumors such as renal cell and ovarian carcinoma, increased expression of PD-L1 on the tumor is associated with poor prognosis (Thompson et al. (2004) *Proc. Natl. Acad. Sci. U.S.A.* 101:17174-17179; Hamanishi et al. (2007) *Proc. Natl. Acad. Sci. U.S.A.* 104:3360-3365). Early clinical correlative studies describe distinct patterns of PD-L1 tumor expression by immunohistochemical staining (IHC), including cytoplasmic, membranous, or absent expression (Brahmer et al. (2010) *J. Clin. Oncol.* 28:3167-3175; Chen et al. (20130) *Clin. Cancer Res.* 19:3462-3473). Expression of membranous PD-L1 on tumors has been associated with higher response rates to PD-1 checkpoint blockade with the monoclonal antibodies (mAb) nivolumab and pembrolizumab (Kefford et al. (2014) *J. Clin. Oncol.* 32:5s (supp): abstract 3005; Gettinger et al. (2014) *J. Clin. Oncol.* 32:5s (supp.): abstract 8024).

One of the limitations of PD-L1 IHC is the difficulty in establishing clear criteria of expression when trying to distinguish membranous from cytoplasmic staining. PD-L1 is a transmembrane protein with 7 exons encoding 5' untranslated, secretory signal, IgV, IgC, 11 amino acid stalk plus transmembrane, cytoplasmic 1, and cytoplasmic 2 domains with a stop codon followed by a 3' untranslated and poly(A) tail. A number of PD-L1 mAbs against the IgV or IgC domains have been reported to give a similar pattern of PD-L1 IHC of tumor tissue characterized by a difficult to interpret mixture of cytoplasmic and membrane staining. These include the 5H1 mAb used in many important reports as well as 339.7G11 and commercial mAbs (clone 15, Sino Biological) (Chen et al. (2013) Clin. Cancer Res. 19:3462-3473). By contrast, IHC with new PD-L1 mAbs specific for the cytoplasmic domain are described herein that give clear membranous staining. These PD-L1 cytoplasmic domain-specific mAbs are more sensitive and specific for Western blot analysis of PD-L1.

Materials and Methods a. Cell Lines

HD-LM2, L428, and OC1-LY1 were cultured respectively in RPMI-20% FBS/pen-strep/glutamine/HEPES, RPMI-10% FBS/pen-strep/glutamine/HEPES/gentamycin, and IMDM-10% FBS/pen-strep/glutamine/HEPES/gentamycin as described. Caki-2, SKBR3, and SKOV3 were maintained in McCoy's 5A media-10% FBS, glutamine and antibiotics as recommended by ATCC. UMRC6 was maintained in DMEM-10% FBS/pen-strep/glutamine/HEPES/gentamycin, and SK12N, BT474 (ATCC) and MDA-MB-231 (ATCC) without HEPES. OVCAR5 was maintained in DMEM-10% FBS/pen-strep/non-essential amino acids. Cell lines 769-P (ATCC), 36M2 and A2780-C70 were maintained in RPMI-10% FBS/pen-strep. Hematologic cell lines were a gift of Dr. Margaret Shipp. Renal cell lines were a gift of Drs. Chuan Shen and William Kaelin. Ovarian lines were a gift of Dr. Panos Konstantinopoulos. Adherent epithelial cell lines (renal, breast, and ovarian lines) were passed by trypsinization; however, for immunophenotyping and protein lysate preparation, cells were detached from plastic with 1 mM EDTA-PBS to minimize cleavage of extracellular protein domains.

b. PD-L1 mAbs

Anti-PD-L1 monoclonal antibodies that recognize the cytoplasmic domain of human PD-L1 protein were generated by immunizing animals with a 19-mer peptide having the sequence, CGIQDTNSKKQSDTHLEET (SEQ ID NO: 1), which represents the last 19 amino acids at the carboxy-terminus of the human membrane-bound PD-L1 polypeptide (see Table 2). Specifically, mus musculus BALB/c PD-L1$^{-/-}$ mice (i.e., PD-L1 deficient mice) were immunized intraperitoneally (i.p.) with 100 micrograms of peptide coupled to Keyhole limpet hemocyanin (KLH) in complete Freunds adjuvant. At 2 week intervals for four more times, the mice were immunized i.p with 100 micrograms of peptide-KLH in incomplete Freund's adjuvant. Twenty-four days after the last immunization, the mouse was given 50 micrograms of peptide coupled to bovine serum albumen (BSA) by the intravenous (i.v.) route. Four days later the spleen and lymph nodes were harvested and used in a hybridoma fusion with SP2/0 myeloma cells. Cells were cultured in 96 well plates and assayed by ELISA on peptide-BSA and by Western blot on lysates of untransfected and human PD-L1 transfected 300.19 cells.

Clone 405.9A11 (i.e., the 9A11; mouse IgG1, kappa) antibody was chosen for further analysis based on its capacity to specifically react with the cytoplasmic domain of PD-L1 in a Western blot format of denatured protein (FIG. 1) and detect PD-L1 by flow cytometry of permeabilized cells. The 9A11 antibody can therefore be used to determine any form of PD-L1 having the cytoplasmic domain, such as a membrane-bound PD-L1 molecule expressed in human tumors and inflammatory situations.

Anti-PD-L1 cytoplasmic domain mAb E1L3 (rabbit IgG) was from Cell Signaling Technology. Clones 29E.2A3 (mouse IgG2b, kappa), 339.7G1 and 368A.5A4 (both mouse IgG1, Kappa) have been described in Chen et al. (2013) Clin. Cancer Res. 19:3462-3473) and recognize an epitope in the PD-L1 IgV domain. Clone 15 (rabbit IgG) was from Sino Biologicals.

c. Immunophenotyping

Cells from culture were suspended in flow cytometry wash buffer (PBS/2% FBS/0.02% sodium azide/0.5 mM EDTA) to minimize clumping of epithelial cells. Primary and secondary antibodies were used at 10 ug/ml working concentration, isotype controls included MOPC-21 (mIgG1), C1.18.4 (mIgG2a), and MPC.11 (mIgG2b). The anti-PD-L1 antibodies, clone 29E.2A3 (mIgG2b) have been previously described. The anti-PD-L2 antibodies, clone 24F.10C12 (mIgG2a) and 3.2 (mIgG1) have also been previously described. The anti-TIM-1 antibody, clone 1D12 (mIgG1), has been previously described. Anti-MHC class 1, W6/32 (mIgG2a) and MHC class II, 9.49 (mIgG2a) have been previously described. After 30 minutes incubation on ice, cells were washed twice and incubated with goat anti-mouse IgG antibody conjugated to PE (cat#1030-09, Southern Biotech) for 30 minutes on ice. Cells were washed twice and resuspended in 2% formalin in PBS and stored at 4° C. until analyzed on a Canto™ II cytometer. Flow cytometry data was analyzed with FlowJo software.

d. Western Analysis

Protein lysates were prepared with RIPA buffer or M-PER per manufacturer's instructions (cat#89901 and cat#78503, Thermo Scientific), and protease inhibitor cocktail was added to the buffer (complete Ultra tablets, mini, EDTA-free, cat#05892791001, Roche) prior to lysate preparation. Thirty five ug of lysates were loaded into a 4-15% gradient mini-Protean TGX gel (catalog 456-1086, Biorad) and transferred by semidry method. Membranes were blocked with TBST with 12% non-fat milk and 1% goat sera for 1 hour at room temperature. The membrane was washed with TBST and incubated with the primary antibody (final concentration of 20 ug/ml for 339.7G11, 10 ug/ml for 368.5A4, 5 ug/ml for 405.9A11, and 1 ug/ml for beta-actin, cat# ab8226, abcam) in TBST and 1% BSA at 4° C. overnight. Membranes were washed with TBST 3 times at room temperature and incubated with secondary antibody (1:40100, goat anti-mouse IgG cat#1031-05, Southern Biotech) in TBST, 6% non-fat milk and 0.5% goat sera for 30 min. After 3 additional washes with TBST, a 1:1 ratio of ECL substrate:enhancer was added to the membrane (SuperSignal West Pico Stable Peroxide Solution cat#1856135, SuperSignal West Pico Luminol/Enhancer Solution cat#1856136, ThermoScientific) and imaged on Hyblot CL autoradiography film (cat# E3018, Denville Scientific, Inc).

In specific embodiments, protein lysates were made from 300.19 cells stably transfected with human PD-L1, as well as from Caki-2 cells. Caki-2 is a human clear cell renal cell carcinoma (ccRCC) line that displays epithelial morphology and expresses wildtype von Hippel-Lindau (VHL) tumor-suppressor protein. By flow cytometry, the Caki-2 cell line expresses a low level of PD-L1 typical of a solid tumor cell line. Protein lysates were run on SDS-PAGE as a single wide lane the width of the gel and blotted onto nitrocellulose. The blot was mounted in a Western blotting apparatus with 24 channels. The concentrations of anti-hPD-L1 mAbs indicated in FIG. 1 were added to each channel, incubated, then washed and developed with anti-mouse IgG coupled to HRP. The results show that each of the three anti-hPD-L1 mAbs 9A11, 368.7G11 (recognizes a PD-L1 extracellular domain epitope), and 368.5A4 (recognizes a PD-L1 extracellular domain epitope) can detect human PD-L1 (hPD-L1) by Western blot in Caki-2 cells and 300-hPD-L1 with good specificity and no background bands. The 5A4 shows the highest affinity and gives a detectable band in Caki-2 cells at concentrations as low as 0.02 µg/ml. The 9A11 shows slightly less high affinity and gives a detectable band in Caki-2 cells at concentrations as low as 0.06 µg/ml. The 7G11 shows even lower affinity and gives a detectable band in Caki-2 cells only at high concentration, 5 µg/ml. The blot was stripped and re-probed with anti-actin mAb to verify equal loading. Thus, the 7G11 antibody recognizes PD-L1 with less sensitivity than both the 9A11 and 5A4 antibodies and the 9A11 antibody recognizes PD-L1 with high sensitivity.

As stated above, the 9A11 antibody recognizes a region of PD-L1 that is normally inside the cell. In a live cell this epitope would not be accessible, but standard immunohistochemistry protocols contain alcohol dehydration steps, fixing steps, and the like that permeabilize the cell. In fact, the 9A11 antibody was determined to work surprisingly well (e.g., significantly reduced unwanted background signal relative to standard PD-L1 antibodies, such as those that bind to the PD-L1 extracellular domain) in imnunohistochemistry (IHC) format using formalin-fixed paraffin-embedded human tissue.

e. Immunohistochemistry

IHC using a rabbit anti-PD-L1 monoclonal antibody (clone 15, #10084-R015, 6.2 ug/ml final concentration, Sino Biological, Beijing, China) was performed using 4-µm-thick, FFPE tissue sections on a Benchmark XT autostainer (Ventana Medical System, Tucson, Ariz.) with standard antigen retrieval (CC1 buffer, pH8.0, #950-124, Ventana). UltraView Universal DAB Detection kit (#760-500, Ventana) was used according to the manufacturer's instruction. Counterstaining was performed as part of the automated staining protocol using hematoxylin (#760-2021, Ventana). IHC using the mouse anti-PD-L1 monoclonal antibody (IgG1, generated in the laboratory of G. Freeman, clone 339.7G11, 69 ug/ml final concentration, Boston, Mass.) was performed using the same protocol as above. After staining, slides were washed in soap water and distilled water, dehydrated in graded alcohol and xylene, mounted and cover slipped.

IHC using a mouse anti-PD-L1 monoclonal antibody (IgG1, generated in the laboratory of G. Freeman, clone 405.9A11, 10.4 ug/ml final concentration, Boston, Mass.) was performed using an automated staining system (Bond III, Leica Biosystems, Buffalo Grove, Ill.) following the manufacturer's protocol. Four-um thick paraffin-embedded sections were pre-baked in 60° C. for one hour. Adhesive labels for each protocol were printed and applied to slides. Slides were then loaded onto Bond III with "Bond Universal Covertiles" (Leica Biosystems). PDL1 (405.9A11) immunostaining was performed with 1:125 dilution (final concentration: 10.4 µg/ml) using Discovery Ab diluent (Ventana Medial Systems). Slides were first dewaxed and rehydrated. Heat induced antigen retrieval was performed using ER2 solution (pH8) (Leica Biosystems) for 30 minutes. Primary antibody was incubated for total of 2 hours with two separate applications, follow by 8 minutes of postprimary blocking reagent, 12 minutes of horseradish peroxidase-labeled polymer, 5 minutes of peroxidase block, 15 minutes of DAB developing, and 10 minutes of hematoxylin. All reagents were components of the Bond Polymer Refine detection system (Leica Biosystems). IHC using the rabbit anti-PD-L1 monoclonal antibody (E1L3N, Cell Signaling, Beverly, Mass.) was performed using the same protocol as above, with 1:200 dilution (final concentration: 5.4 ug/ml) using Bond Primary Antibody Diluent. After staining, slides were taken off from the autostainer, dehydrated and coverslipped.

In some embodiments, additional IHC procedures were performed. For example, FIG. 2A shows that robust PD-L1 signal to background staining using the 9A11 antibody (1.3 mg/mL stock concentration) was obtained using the following manual immunohistochemistry protocol:

Materials:
Steamer (Black & Decker)
EDTA buffer pH8 20× (Invitrogen cat#00-5500)
Dual Endogenous Enzyme Block (peroxidase block) (Dako cat# S2003)
Protein Block Serum Free (Dako cat# X0909)
Avidin/Biotin Blocking Kit (Vector cat# SP-2001)
Discovery Ab Diluent (Ventana cat#760-108)
Poly-HRP anti-Mouse secondary (Dako cat# K4007)
TSA (Perkin Elmer cat# FP140 & FP1052)
LSAB Streptavidin-HRP (Dako cat# K1016)
DAB+ Substrate Buffer & Chromogen (Dako cat# K4011)

Stepwise Manual IHC Protocol:
1. Bake slides for 60 minutes at 60° C.
2. Rehydrate slides:
   Xylene: 5 min. 2×
   100% Ethanol: 2 min. 2×
   95% Ethanol: 2 min.
   80% Ethanol: 2 min.
   dH$_2$O
3. Prepare retrieval solution. Pre-heat retrieval solution in steamer for at least 10 minutes.
   Ensure solution reaches approx. 98° C.
4. Bathe slides in heated retrieval solution, 1 mM EDTA, and cover with foil. Insert into steamer and steam at approx. 98° C. for 30 minutes.
5. Cool slides. Rinse and bathe in dH$_2$O. Wipe slides with a Kimwipe and apply hydrophobic pen around tissue. Bathe in 1× Tris with Tween-20 buffer for 5 min. Proceed with staining in room temperature.
6. Wipe slides and load humidifying chamber. Apply peroxidase block for 5 min.
7. Rinse slides with DI water and bathe in buffer for 5 min.
8. Wipe slides and load humidifying chamber. Apply Avidin for 5 min.
9. Rinse slides with buffer and bathe in fresh buffer for 5 min.
10. Wipe slides and load humidifying chamber. Apply Biotin for 5 min.
11. Rinse slides with buffer and bathe in fresh buffer for 5 min.
12. Wipe slides and load chamber. Apply protein block for 10 minutes.
13. No buffer wash between protein block and primary antibody. Apply primary antibody, anti-PDL1, diluted in Discovery antibody diluents 1:75, incubate for 1 hr.
14. Rinse slides with buffer and bathe in fresh buffer for 5 min.
15. Wipe slides and load chamber. Apply secondary antibody for 30 min.
16. Rinse slides with buffer and bathe in fresh buffer for 5 min.
17. Wipe slides and load chamber. Apply TSA 1:200 for 10 minutes
18. Rinse slides with buffer and bathe in fresh buffer for 10 min.
19. Wipe slides and load chamber. Apply Streptavidin for 30 minutes 20. Rinse slides with buffer and bathe in fresh buffer for 5 min.
21. Wipe slides and load chamber. Apply chromogen substrate. (1 drop DAB per 1 mL buffer)
22. Rinse off DAB with dH$_2$O into separate waste container. Bathe slides in dH$_2$O. Proceed with counterstain.
23. Dehydrate
24. Coverslip Similarly, FIG. 2B shows that robust PD-L1 signal to background staining using the 9A11 antibody (1.3 mg/mL stock concentration) was obtained using a Ventana Benchmark XT automated staining platform using the following protocol:

Materials:
UltraView DAB Detection Kit (Ventana, Cat#760-500)
Bluing Reagent (Ventana, Cat#760-2037)
Hematoxylin (Ventana, Cat#760-2021)
EZ prep (Ventana, Cat#950-102).
LCS (Ventana, Cat#650-010),
Reaction Buffer (Ventana, Cat#950-300)
CC1 (Ventana, Cat#950-124)
Discovery Ab Diluent (Ventana, Cat#760-108)
Stepwise Protocol Programmed on Benchmark XT:
*Install Procedure: XT ultraView DAB v3" Software onto the Benchmark XT Prior to Running this Protocol
1. Paraffin (select)
2. Deparaffinization (select)
3. Cell Conditioning (select)
   Conditioner #1: short-8 min (select)
   Milder CC1: 30 min (select)
   Standard CC1: 60 min (select)
4. Ab Incubation (select)
5. Titration (select)
   Hand apply 100 ul of primary antibody diluted in Discovery Ab Diluent, 1:25, incubate for 1 hour (final conc. on slides becomes 13 µg/ml, due to already existing reagents on slides at time of primary antibody application)
6. Counterstain (select)
7. Apply one drop of Hematoxylin, incubate for 4 min (select)
8. Post counterstain (select)
9. Apply one drop of Bluing Reagent, incubate for 4 min (select)
10. Automated procedure ends, remove slides from Benchmark XT
11. Wash slides with soap water, dehydrate, and coverslip By contrast, FIG. 2C shows significantly weaker and diffuse PD-L1 signal to background staining using the mouse anti-human PD-L1 antibody, 339.7G011 (0.69 mg/mL stock concentration), which recognizes a PD-L1 extracellular domain epitope, using the following manual immunohistochemistry protocol:

Materials:
Steamer (Black & Decker)
EDTA buffer pH8 20× (Invitrogen cat#00-5500)
Dual Endogenous Enzyme Block (peroxidase block) (Dako cat# S2003)
Protein Block Serum Free (Dako cat# X0909)
Avidin/Biotin Blocking Kit (Vector cat# SP-2001)
Discovery Ab Diluent (Ventana cat#760-108)
Poly-HRP anti-Mouse secondary (Dako cat# K4007)
TSA (Perkin Elmer cat# FP140 & FP1052)
LSAB Streptavidin-H-RP (Dako cat# K1016)
DAB+Substrate Buffer & Chromogen (Dako cat# K4011)

Stepwise Manual IHC Protocol:
1. Bake slides for 60 minutes at 60° C.
2. Rehydrate slides:
   Xylene: 5 min. 2×
   100% Ethanol: 2 min. 2×
   95% Ethanol: 2 min.
   80% Ethanol: 2 min.
   dH$_2$O
3. Prepare retrieval solution. Pre-heat retrieval solution in steamer for at least 10 minutes. Ensure solution reaches approx. 98° C.
4. Bathe slides in heated retrieval solution, 1 mM EDTA, and cover with foil. Insert into steamer and steam at approx. 98° C. for 30 minutes.
5. Cool slides. Rinse and bathe in dH$_2$O. Wipe slides with a Kimwipe and apply hydrophobic pen around tissue. Bathe in 1× Tris with Tween-20 buffer for 5 min. Proceed with staining in room temperature.
6. Wipe slides and load humidifying chamber. Apply peroxidase block for 5 min.
7. Rinse slides with DI water and bathe in buffer for 5 min.
8. Wipe slides and load humidifying chamber. Apply Avidin for 5 min.
9. Rinse slides with buffer and bathe in fresh buffer for 5 min.
10. Wipe slides and load humidifying chamber. Apply Biotin for 5 min.
11. Rinse slides with buffer and bathe in fresh buffer for 5 min.
12. Wipe slides and load chamber. Apply protein block for 10 minutes.
13. No buffer wash between protein block and primary antibody. Apply primary antibody, anti-PDL1, diluted in Discovery antibody diluents 1:10, incubate for 1 hr.
14. Rinse slides with buffer and bathe in fresh buffer for 5 min.
15. Wipe slides and load chamber. Apply secondary antibody for 30 min.
16. Rinse slides with buffer and bathe in fresh buffer for 5 min.
17. Wipe slides and load chamber. Apply TSA 1:200 for 10 minutes
18. Rinse slides with buffer and bathe in fresh buffer for 10 min.
19. Wipe slides and load chamber. Apply Streptavidin for 30 minutes
20. Rinse slides with buffer and bathe in fresh buffer for 5 min.
21. Wipe slides and load chamber. Apply chromogen substrate. (1 drop DAB per 1 mL buffer)
22. Rinse off DAB with dH$_2$O into separate waste container. Bathe slides in dH$_2$O. Proceed with counterstain.
23. Dehydrate
24. Coverslip Likewise, FIG. 2D shows significantly weaker and diffuse PD-L1 signal to background staining using the mouse anti-human PD-L1 antibody, 339.7G11 (0.69 mg/mL stock concentration), which recognizes a PD-L1 extracellular domain epitope, using a Ventana Benchmark XT automated staining platform using the following protocol:

Materials:
UltraView DAB Detection Kit (Ventana, Cat#760-500)
Bluing Reagent (Ventana, Cat#760-2037)
Hematoxylin (Ventana, Cat#760-2021)
EZ prep (Ventana, Cat#950-102),
LCS (Ventana, Cat#650-010),
Reaction Buffer (Ventana, Cat#950-300)

Figure 3:
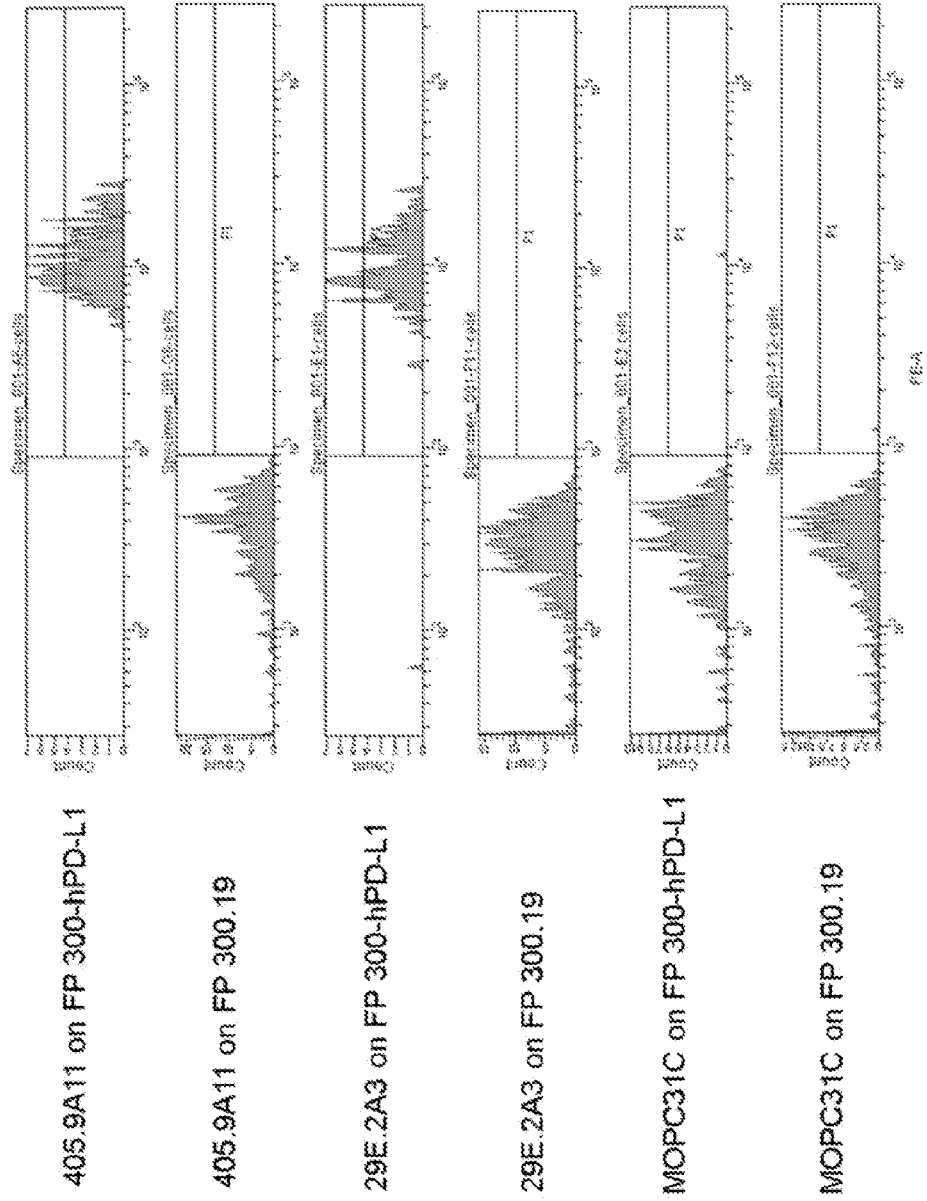
FIG. 3 shows the results of 300.19 and 300-hPD-L1 transfected cells that were fixed, permeabilized, and incubated for 30 minutes with the following mAbs: 405.9A11, a hPD-L1 cytoplasmic domain-specific mAb; 29E.2A3, a hPD-L1 extracellular domain-specific mAb, and MOPC31C, an isotype control mouse IgG1. Cells were then washed, incubated with goat anti-mouse IgG-PE for 30 min, washed, and analyzed by flow cytometry.

CC1 (Ventana, Cat#950-124)
Discovery Ab Diluent (Ventana, Cat#760-108)
Stepwise Protocol Programmed on Benchmark XT:
*Install Procedure: XT ultraView DAB v3" Software onto the Benchmark XT Prior to Running this Protocol
1. Paraffin (select)
2. Deparaffinization (select)
3. Cell Conditioning (select)
   Conditioner #1: short-8 min (select)
   Milder CC1: 30 min (select)
   Standard CC1: 60 min (select)
4. Ab Incubation (select)
5. Titration (select)
   Hand apply 100 ul of primary antibody diluted in Discovery Ab Diluent, 1:2.5, incubate for 1 hour (final conc. on slides becomes 69 ug/ml, due to already existing reagents on slides at time of primary antibody application)
6. Counterstain (select)
7. Apply one drop of Hematoxylin, incubate for 4 min (select)
8. Post counterstain (select)
9. Apply one drop of Bluing Reagent, incubate for 4 min (select)
10. Automated procedure ends, remove slides from Benchmark XT
11. Wash slides with soap water, dehydrate, and coverslip Moreover, the 9A11 antibody was demonstrated to detect PD-L1 in fixed, permeabilized cells using flow cytometry (FIG. 3).

In addition, intracellular delivery of the 9A11 antibody, such as in therapeutic applications, is expected to modulate PD-L1 function to modulate (e.g., inhibit or enhance) intracellular signaling mediated by membrane-bound PD-L1's interaction with its natural receptor, such as PD-1, B7-1, and the like.

The 9A11 antibody was sequenced and the sequences are presented in Table 1 below. In addition, hybridoma cell line 405.1.9A11.2D6.3.5 was deposited with the American Type Culture Collection (ATCC) and was received on Apr. 26, 2018 in accordance with the provisions of the Budapest Treaty on the International Recognition of the Deposit of Microorganisms for the Purposes of Patent Procedure under deposit number PTA-124921.

f. IHC Staining Evaluation and Scoring

Reactivity for PD-L1 was determined and scored by two pathologists. Discrepant results in staining interpretation (<5% of cases) were resolved in a consensus conference. For each stained slide, the percentage of tumor cells showing positive staining for PD-L1 was recorded in 10% increments (0-100%). In addition, the intensity of positive staining was recorded: (−)=no staining detected, (1+)=weak staining, (2+)=moderate staining, (3+)=strong staining. A case was scored as positive if at least 20% of the tumor cells stained positive for PD-L1 with an intensity of 1+, 2+, or 3+.

TABLE 1

Identification and sequencing of the leader and variable regions of anti-PD-L1 monoclonal antibody 405.9A11

9A11 Light Chain Variable (vK) DNA and Amino Acid Sequences*

```
LOCUS      9A11-VK 396 bp DNA linear
FEATURES        Location/Qualifiers
J_segment       367..396
                /label = JK V_segment       340..366
                /label = CDR3

V_region        244..339
                /label = FWR3

V_segment       223..243
                /label = CDR2

V_region        178..222
                /label = FWR2

V_segment       130...177
                /label = CDR1

V_region        61..129
                /label = FWR1 sig_peptide     1..601
                /label_LS

CDS             1..396
                /label = 9A11\VK
```

(SEQ ID NO: 2)
/translation="MRCLVQFLGLLVLWIPGSTADIVMTQAAFSNPVTLGTSAS
LSCRSSKSLLHSNGITYLYWYLQKPGQSPQLLIYQMSNLASGVPDRFSGSGSGT
DFTLRISRVEAEDVGVYYCAQNLEPPLTFGAGTKLELK"

BASE COUNT 88 a 97c 102g 109t
ORIGIN                                                                      (SEQ ID NO: 3)
   1    atgaggtgcc  ttgttcagtt  tctggggctg  cttgtgctct  ggatccctgg  atccactgca
  61    gatattgtga  tgacgcaggc  tgcattctcc  aatccagtca  ctcttggaac  atcagcttcc
```

TABLE 1-continued

Identification and sequencing of the leader and variable regions of anti-PD-L1 monoclonal antibody 405.9A11

```
121   atctcctgca ggtccagtaa gagtctccta catagtaatg gcatcactta tttgtattgg
181   tatctgcaga agccaggcca gtctcctcag ctcctgattt atcagatgtc caaccttgcc
241   tcaggagtcc cagacaggtt cagtggcagt gggtcaggaa ctgatttcac actgagaatc
301   agcagagtgg aggctgagga tgtgggtgtt tattactgtg ctcaaaatct agaacctccg
361   ctcacgttcg gtgctgggac caagctggag ctgaaa
```

Signal Peptide (base pairs 1-60): (SEQ ID NO: 4)
```
  1   atgaggtgcc ttgttcagtt tctggggctg cttgtgctct ggatccctgg atccactgca   60
```

Framework 1 (base pairs 61-129): (SEQ ID NO: 5)
```
 61   gatattgtga tgacgcaggc tgcattctcc aatccagtca ctcttggaac atcagcttcc  129
```

CDR-L1 (base pair 130-177): (SEQ ID NO: 6)
```
130   aggtccagta agagtctccta catagtaatg gcatcactta tttgtat              177
```
(SEQ ID NO: 7)
```
      R  S  S  K  S  L  L  H  S  N  G  I  T  Y  L  Y
```

Framework 2 (base pairs 178-222): (SEQ ID NO: 8)
```
178   tgg tatctgcaga agccaggcca gtctcctcag ctcctgattt at                222
```

CDR-L2 (base pairs 223-243): (SEQ ID NO: 9)
```
223   cagatgtc caaccttgcc tca                                           243
```
(SEQ ID NO: 10)
```
      Q  M  S  N  L  A  S
```

Framework 3 (base pairs 244-339): (SEQ ID NO: 11)
```
244   ggagtcc cagacaggtt cagtggcagt gggtcaggaa ctgatttcac actgagaatc
      agcagagtgg aggctgagga tgtgggtgtt tattactgt                       339
```

CDR-L3 (base pairs 340-366): (SEQ ID NO: 12)
```
340   g ctcaaaatct agaacctccg ctcacg                                    366
```
(SEQ ID NO: 13)
```
      A  Q  N  L  E  P  P  L  T
```

J Segment (base pairs 367-396): (SEQ ID NO: 14)
```
367   ttcg gtgctgggac caagctggag ctgaaa                                 396
```

9A11 Heavy Chair Variable (vH) DNA and Amino Acid Sequences*

```
LOCUS  91AA-VH 414 bp DNA linear
FEATURES      Location/Qualifiers
J_segment     382..414
              /label = JH V_segment     352..381
              /label = CDR3

V_region      256..351
              /label = FWR3

V_segment     205..255
              /label = CDR2

V_region      163..201
              /label = FWR2

V_segment     148..162
              /label = CDR1

V_region      58..147
              /label = FWR1 sig_peptide   1..57
              /label = LS
```

TABLE 1-continued

Identification and sequencing of the leader and variable regions of anti-PD-L1 monoclonal antibody 405.9A11

CDS          1..414
                /label = 9A11\VH (SEQ ID NO: 15)

/translation = "MKCSWVIVFLMAVVIGINSEVQLQQSGAELVRSGASVKLAS
CTAFGLNTK<u>DYYIH</u>WVKQRPEQGLEWIG<u>WIDPENGKTAYAPKFQG</u>KATLTAYTS
SDTAYLHLSSLTSEDTAVYYCKT<u>GGYDVYFLDY</u>WGQGTSVTVSS"

BASE COUNT 102 a 103 c 109 g 100 t
ORIGIN                                                                     (SEQ ID NO: 16)

1     atgaaatgca gctgggtcat cgtcttcctg atggcagtgg ttataggaat caattcagag 61     gttcagctgc agcagtctgg ggcagagctt gtgaggtcag gggcctcagt caagttgtcc 121     tgcacagctt ttggcctcaa cattaaagac tactatatac actgggtaaa acagaggcct 181     gaacagggcc tggagtggat tggatggatt gatcctgaga atggtaaaac tgcatatgcc 241     ccgaagttcc agggcaaggc cactctgact gcatacacgt cctccgacac agcctacctg 301     cacctcagca gcctgacatc tgaggacact gccgtctatt actgtaagac tggtggttac 361     gacgtctatt ttctggacta ctggggtcaa ggaacctcag tcaccgtctc ctca Signal Peptide (base pairs 1-57):                             (SEQ ID NO: 17)

1     atgaaatgta gttgggttat tgttttttg atggtagtgg ttataggaat caattca      57

Framework 1 (base pairs 58-147):                              (SEQ ID NO: 18)

58     gag gttcagctgc agcagtctgg ggcagagctt gtgaggtcag gggcctcagt
          caagttgtcc tgcacagctt ttggcctcaa cattaaa                         147

CDR-H1 (base pairs 148-162):                                        (SEQ ID NO: 19)

1438     gac tactatatac ac                                                  162
                                                                             (SEQ ID NO: 20)
        D    Y    Y    I    H Framework 2 (base pairs 163-204):                          (SEQ ID NO: 21)

163     tgggtaaa acagaggcct gaacagggcc tggagtggat tgga                 204

CDR-H2 (base pairs 205-255):                                     (SEQ ID NO: 22)

205     tggatt gatcctgaga atggtaaaac tgcatatgcc ccgaagttcc agggc        255
                                                                              (SEQ ID NO: 23)
        W    I    D    P    E    N    G    K    T    A    Y    A    P    K    F    Q    G Framework 3 (base pairs 256-351):                         (SEQ ID NO: 24)

256     aaggc cactctgact gcatacacgt cctccgacac agcctacctg
          cacctcagca gcctgacatc tgaggacact gccgtctatt actgtaagac t          351

CDR-H3 (base pairs 352-381):                                     (SEQ ID NO: 25)

352     ggtggttac gacgtctatt ttctggacta c                              381
                                                                              (SEQ ID NO: 26)
        G    G    Y    D    V    Y    F    L    D    Y J Segment (base pairs 382-414):                             (SEQ ID NO: 27)

382     tggggtcaa ggaacctcag tcaccgtctc ctca                         414

*CDR definitions and protein sequence numbering according to Kabat. CDR amino acid sequences are underlined in order of CDR1, CDR2, and CDR 3, respectively.

TABLE 2

Representative PD-L1 Sequences of PD-L1S (Secreted) and PD-L1M (Membrane)

| Human PD-L1S cDNA Acid Sequence | (SEQ ID NO: 28) |
|---|---|

```
gcttcccgag gctccgcacc agccgcgctt ctgtccgcct gcagggcatt ccagaaag      58 atg agg ata ttt gct gtc ttt ata ttc atg acc tac tgg cat ttg ctg     106
Met Arg Ile Phe Ala Val Phe Ile Phe Met Thr Tyr Trp His Leu Leu
 1               5                  10                  15 aac gca ttt act gtc acg gtt ccc aag gac cta tat gtg gta gag tat     154
Asn Ala Phe Thr Val Thr Val Pro Lys Asp Leu Tyr Val Val Glu Tyr
             20                  25                  30 ggt agc aat atg aca att gaa tgc aaa ttc cca gta gaa aaa caa tta     202
Gly Ser Asn Met Thr Ile Glu Cys Lys Phe Pro Val Glu Lys Gln Leu
         35                  40                  45 gac ctg gct gca cta att gtc tat tgg gaa atg gag gat aag aac att     250
Asp Leu Ala Ala Leu Ile Val Tyr Trp Glu Met Glu Asp Lys Asn Ile
     50                  55                  60 att caa ttt gtg cat gga gag gaa gac ctg aag gtt cag cat agt agc     298
Ile Gln Phe Val His Gly Glu Glu Asp Leu Lys Val Gln His Ser Ser
 65                  70                  75                  80 tac aga cag agg gcc cgg ctg ttg aag gac cag ctc tcc ctg gga aat     346
Tyr Arg Gln Arg Ala Arg Leu Leu Lys Asp Gln Leu Ser Leu Gly Asn
                 85                  90                  95 gct gca ctt cag atc aca gat gtg aaa ttg cag gat gca ggg gtg tac     394
Ala Ala Leu Gln Ile Thr Asp Val Lys Leu Gln Asp Ala Gly Val Tyr
             100                 105                 110 cgc tgc atg atc agc tat ggt ggt gcc gac tac aag cga att act gtg     442
Arg Cys Met Ile Ser Tyr Gly Gly Ala Asp Tyr Lys Arg Ile Thr Val
         115                 120                 125 aaa gtc aat gcc cca tac aac aaa atc aac caa aga att ttg gtt gtg     490
Lys Val Asn Ala Pro Tyr Asn Lys Ile Asn Gln Arg Ile Leu Val Val
 130                 135                 140 gat cca gtc acc tct gcc cat gaa ctg aca tgt cag gct gag ggc tac     538
Asp Pro Val Thr Ser Ala His Glu Leu Thr Cys Gln Ala Glu Gly Tyr
145                 150                 155                 160 ccc aag gcc gaa gtc atc tgg aca agc agt gac cat caa gtc ctg agt     536
Pro Lys Ala Glu Val Ile Trp Thr Ser Ser Asp His Gln Val Leu Ser
                 165                 170                 175 ggt aag acc acc acc acc aat tcc aag aga gag gag aag ctt ttc aat     634
Gly Lys Thr Thr Thr Thr Asn Ser Lys Arg Glu Glu Lys Leu Phe Asn
             180                 185                 190 gtg acc agc aca ctg aga atc aac aca aca act aat gag att ttc tac     682
Val Thr Ser Thr Leu Arg Ile Asn Thr Thr Thr Asn Glu Ile Phe Tyr
         195                 200                 205 tgc act ttt agg aga tta gat cct gag gaa aac cat aca gct gaa ttg     730
Cys Thr Phe Arg Arg Leu Asp Pro Glu Glu Asn His Thr Ala Glu Leu
     210                 215                 220 gtc atc cca ggt aat att ctg aat gtg tcc att aaa ata tgt cta aca     778
Val Ile Pro Gly Asn Ile Leu Asn Val Ser Ile Lys Ile Cys Leu Thr
225                 230                 235                 240 ctg tcc cct agc acc tagcatgatg tctgcctatc atagtcattc agtgattgtt     833
Leu Ser Pro Ser Thr
                245 gaataaatga atgaatgaat aacactatgt ttacaaaata tatcctaatt cctcacctcc     893 attcatccaa accatattgt tacttaataa acattcagca gatatttatg gaataaaaaa     953 aaaaaaaaaa aaaaa                                                      968
```

TABLE 2-continued

Representative PD-L1 Sequences of PD-L1S (Secreted) and PD-L1M (Membrane)

Human PD-L1S Amino Acid Sequence　　　　　　　　　(SEQ ID NO: 29)

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
            130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
            210                 215                 220

Val Ile Pro Gly Asn Ile Leu Asn Val Ser Ile Lys Ile Cys Leu Thr
225                 230                 235                 240

Leu Ser Pro Ser Thr
                245
```

Human PD-L1M cDNA Acid Sequence　　　　　　　　　(SEQ ID NO: 30)

```
cgaggctccg caccagccgc gcttctgtcc gcctgcaggg cattccagaa agatgagg     58
                                                        Met Arg
                                                        1 ata ttt gct gtc ttt ata ttc atg acc tac tgg cat ttg ctg aac gca    106
Ile Phe Ala Val Phe Ile Phe Met Thr Tyr Trp His Leu Leu Asn Ala
        5                   10                  15 ttt act gtc acg gtt ccc aag gac cta tat gtg gta gag tat ggt agc    154
Phe Thr Val Thr Val Pro Lys Asp Leu Tur Val Val Glu Tyr Gly Ser
            20                  25                  30 aat atg aca att gaa tgc aaa ttc cca gta gaa aaa caa tta gac ctg    202
Asn Met Thr Ile Glu Cys Lys Phe Pro Val Glu Lys Gln Leu Asp Leu
35                  40                  45                  50 gct gca cta att gtc tat tgg gaa atg gag gat aag aac att att caa    250
Ala Ala Leu Ile Val Tyr Trp Glu Met Glu Asp Lys Asn Ile Ile Gln
                55                  60                  65 ttt gtg cat gga gag gaa gac ctg aag gtt cag cat agt agc tac aga    298
Phe Val His Gly Glu Glu Asp Leu Lys Val Gln His Ser Ser Tyr Arg
            70                  75                  80
```

TABLE 2-continued

Representative PD-L1 Sequences of PD-L1S (Secreted) and PD-L1M (Membrane)

```
cag agg gcc cgg ctg ttg aag gac cag ctc tcc ctg gga aat gct gca    346
Gln Arg Ala Arg Leu Leu Lys Asp Gln Leu Ser Leu Gly Asn Ala Ala
         85                  90                  95 ctt cag atc aca gat gtg aaa ttg cag gat gca ggg gtg tac cgc tgc    394
Leu Gln Ile Thr Asp Val Lys Leu Gln Asp Ala Gly Val Tyr Arg Cys
100                 105                 110 atg atc agc tat ggt ggt gcc gac tac aag cga att act gtg aaa gtc    442
Met Ile Ser Tyr Gly Gly Ala Asp Tyr Lys Arg Ile Thr Val Lys Val
115                 120                 125                 130 aat gcc cca tac aac aaa atc aac caa aga att ttg gtt gtg gat cca    490
Asn Ala Pro Tyr Asn Lys Ile Asn Gln Arg Ile Leu Val Val Asp Pro
                135                 140                 145 gtc acc tct gaa cat gaa ctg aca tgt cag gct gag ggc tac ccc aag    538
Val Thr Ser Glu His Glu Leu Thr Cys Gln Ala Glu Gly Tyr Pro Lys
        150                 155                 160 gcc gaa gtc atc tgg aca agc agt gac cat caa gtc ctg agt ggt aag    586
Ala Glu Val Ile Trp Thr Ser Ser Asp His Gln Val Leu Ser Gly Lys
        165                 170                 175 acc acc acc acc aat tcc aag aga gag gag aag ctt ttc aat gtg acc    634
Thr Thr Thr Thr Asn Ser Lys Arg Glu Glu Lys Leu Phe Asn Val Thr
180                 185                 190 agc aca ctg aga atc aac aca aca act aat gag att ttc tac tgc act    682
Ser Thr Leu Arg Ile Asn Thr Thr Thr Asn Glu Ile Phe Tyr Cys Thr
195                 200                 205                 210 ttt agg aga tta gat cct gag gaa aac ccat aca gct gaa ttg gtc atc   730
Phe Arg Arg Leu Asp Pro Glu Glu Asn His Thr Ala Glu Leu Val Ile
                215                 220                 225 cca gaa cta cct ctg gca cat cct cca aat gaa agg act cac ttg gta    778
Pro Glu Leu Pro Leu Ala His Pro Pro Asn Glu Arg Thr His Leu Val
        230                 235                 240 att ctg gga gcc atc tta tta tgc ctt ggt gta gca ctg aca ttc atc    826
Ile Leu Gly Ala Ile Leu Leu Cys Leu Gly Val Ala Leu Thr Phe Ile
        245                 250                 255 ttc cgt tta aga aaa ggg aga atg atg gat gtg aaa aaa tgt ggc atc    874
Phe Arg Leu Arg Lys Gly Arg Met Met Asp Val Lys Lys Cys Gly Ile
        260                 265                 270 caa gat aca aac tca aag aag caa agt gat aca cat ttg gag gag acg    922
Gln Asp Thr Asn Ser Lys Lys Gln Ser Asp Thr His Leu Glu Glu Thr
275                 280                 285
```

(SEQ ID NO: 30)
```
taatccagca ttggaacttc tgatcttcaa gcagggattc tcaacctgtg gtttagggggt    982
tcatcggggc tgagcgcact aagaggaagg aatgggcccg tgggatgcag gcaatgtggg   1042
acttaaaagg cccaagcact gaaaatggaa cctggcgaaa gcagaggagg agaatgaaga   1102
aagatggagt caaacaggga gcctggaggg agaccttgat actttcaaat gcctgagggg   1162
ctcatcgacg cctgtgacag ggagaaagga tacttctgaa caaggagcct ccaagcaaat   1222
catccattgc tcatcctagg aagacgggtt gagaatccct aatttgaggg tcagttcctg   1282
cagaagtgcc ctttgcctcc actcaatgcc tcaatttgtt ttctgcatga ctgagagtct   1342
cagtgttgga acgggacagt atttatgtat gagtttttcc tatttatttt gagtctgtga   1402
ggtcttcttg tcatgtgagt gtggttgtga atgatttctt ttgaagatat attgtagtag   1462
atgttacaat tttgtcgcca aactaaactt gctgcttaat gatttgctca catctagtaa   1522
aacatggagt atttgtaaaa aaaaaaaaa a                                   1553
```

TABLE 2-continued

Representative PD-L1 Sequences of PD-L1S (Secreted) and PD-L1M (Membrane)

Human PD-L1M Amino Acid Sequence                              (SEQ ID NO: 31)

```
Met Arg Ile Phe Ala Val Phe Ile Phe Met Thr Tyr Trp His Leu Leu
  1               5                  10                 15

Asn Ala Phe Thr Val Thr Val Pro Lys Asp Leu Tyr Val Val Glu Tyr
                 20                  25                 30

Gly Ser Asn Met Thr Ile Glu Cys Lys Phe Pro Val Glu Lys Gln Leu
             35                  40                 45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                 80

Tyr Arg Gln Arg Ala Arg Leu Leu Lys Asp Gln Leu Ser Leu Gly Asn
                 85                  90                 95

Ala Ala Leu Gln Ile Thr Asp Val Lys Leu Gln Asp Ala Gly Val Tyr
                100                 105                110

Arg Cys Met Ile Ser Tyr Gly Gly Ala Asp Tyr Lys Arg Ile Thr Val
                115                 120                125

Lys Val Asn Ala Pro Tyr Asn Lys Ile Asn Gln Arg Ile Leu Val Val
                130                 135                140

Asp Pro Val Thr Ser Glu His Glu Leu Thr Cys Gln Ala Glu Gly Tyr
145                 150                 155                160

Pro Lys Ala Glu Val Ile Trp Thr Ser Ser Asp His Gln Val Leu Ser
                165                 170                175

Gly Lys Thr Thr Thr Thr Asn Ser Lys Arg Glu Glu Lys Leu Phe Asn
                180                 185                190

Val Thr Ser Thr Leu Arg Ile Asn Thr Thr Thr Asn Glu Ile Phe Tyr
                195                 200                205

Cys Thr Phe Arg Arg Leu Asp Pro Glu Glu Asn His Thr Ala Glu Leu
                210                 215                220

Val Ile Pro Glu Leu Pro Leu Ala His Pro Pro Asn Glu Arg Thr His
225                 230                 235                240

Leu Val Ile Leu Gly Ala Ile Leu Leu Cys Leu Gly Val Ala Leu Thr
                245                 250                255

Phe Ile Phe Arg Leu Arg Lys Gly Arg Met Met Asp Val Lys Lys Cys
                260                 265                270

Gly Ile Gln Asp Thr Asn Ser Lys Lys Gln Ser Asp Thr His Leu Glu
                275                 280                285

Glu Thr
290
```

The development of PD-L1 mAbs for immunohistochemistry (IHC) of FFPE tissues has been difficult with a mix of membranous and cytoplasmic staining. It was previously reported that 7G11 and clone 15 (Sino Biologicals) antibodies can detect PD-L1 in FFPE specimens (Chen et al. (2013) *Clin. Cancer Res.* 19:3462-3473) and show a staining pattern similar to that previously described with the 5H1 antibody: membranous and cytoplasmic expression (Brahmer et al. (2010) *J. Clin. Oncol.* 28:3167-3175). Multiple other PD-L1 mAbs work poorly or not at all in IHC with high background (Gadiot et al. (2011) *Cancer* 117:2192-2201). As all the tested mAbs recognize a determinant in the extracellular domain, it was reasoned that a mAb specific for the cytoplasmic domain might give more specific membranous staining and facilitate the measurement of tumor cell expression. In addition, many B7/CD28 family proteins have splice variants that lack the transmembrane domain (Nielsen et al. (2005) *Cell. Immunol.* 235:109-116; Ueda et al. (2003) *Nature* 423:506-511). PD-L1 splice variants that lack the transmembrane and/or have deletions in the IgV or IgC domains are present in the Genbank database. Whether these PD-L1 splice variants are secreted, accumulate intracellularly, or are unstable and degraded is currently not known.

Figure 4:
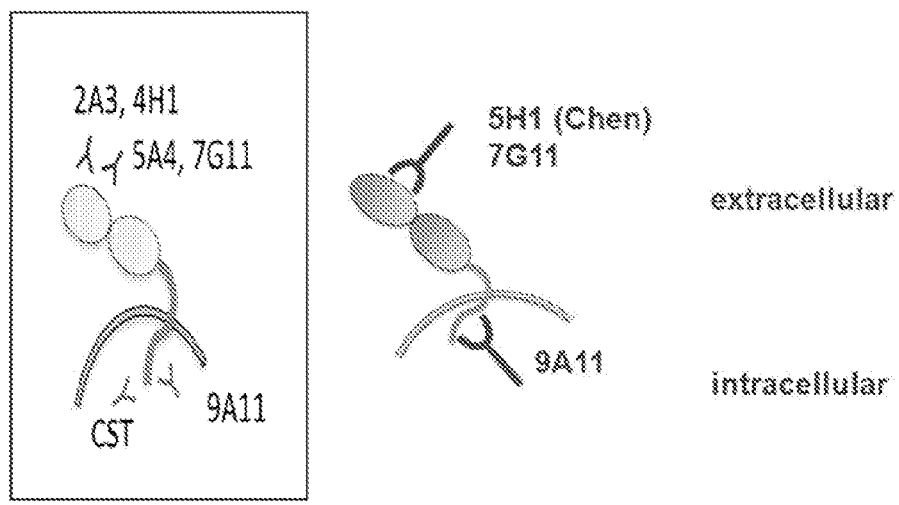
FIG. 4 shows a schematic diagram of the specificities of various anti-PD-L1 antibodies. mAbs 9A11 and E1L3 are directed against the cytoplasmic tail of PD-L1 while others are directed against the extracellular domain of PD-L1.

PD-L1 deficient mice were immunized with a PD-L1 cytoplasmic domain peptide and mAb, 405.9A11, specific for the human PD-L1 cytoplasmic domain, was generated. Initial screening of the antibody for specificity was performed by intracellular flow cytometry and Western blot analysis of human PD-L1 transfected and untransfected cells as described above. The 9A11 mAb was compared with previously generated mAbs against the extracellular domain (FIG. 4) to assess sensitivity and specificity for endogenous levels of native human PD-L1 in Western blots of human tumor cell lines. It was determined that 9A11 is both more sensitive and more specific than 7G11 and as sensitive as 5A4 in Western blot analysis of human cell lines (FIG. 5). mAb 9A11 Western blotted only a single 50 KD band that was also detected by the other PD-L1 mAbs. However, 7G11 also detected several lower MW bands, ranging from 35 to 45 KD. While unglycosylated PD-L1 is expected to be about 23 kDa, mature PD-L1 is expected to be 45-50 kDa when full glycosylated. While 5A4 is highly specific for mature human PD-L1 by Western blot and FACS, it does not work in IHC.

Figure 5:
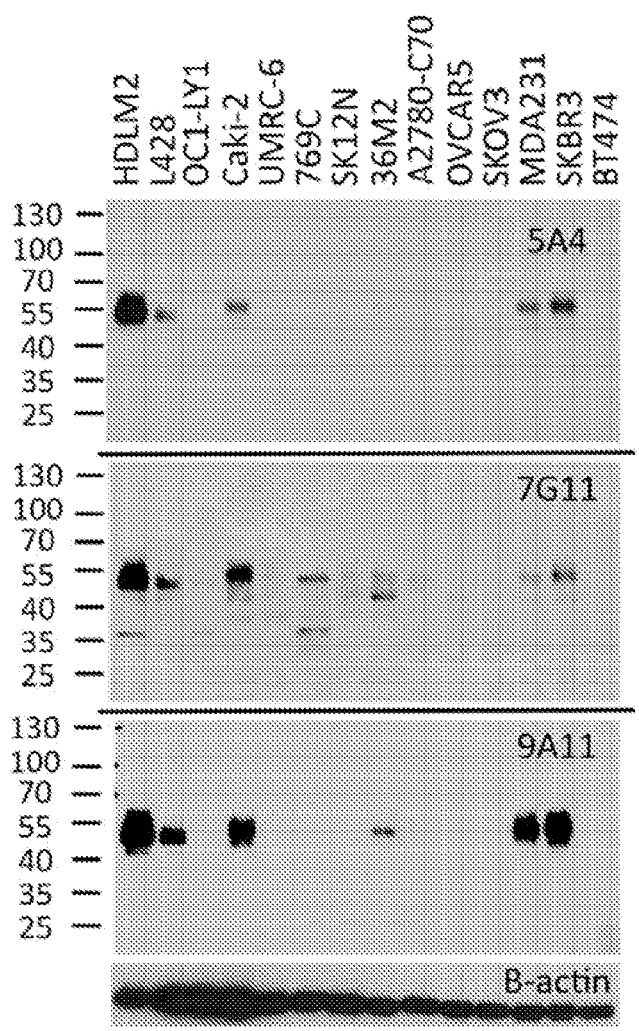
FIG. 5 shows the result of Western blot analyses of hematologic (HDLM2, L428, OC1-LY1), kidney (Caki-2, UMRC-6, 769C, SK12N), ovarian (36M2, A2780-C70, OVCAR3), and breast cancer cell lines (MDA231, SKBR3, BT474) with the anti-PD-L1 mAbs, 5A4 (10 ug/ml), 7G11 (20 ug/ml), and 9A11 (5 ug/ml), or an anti-β-actin antibody.
Figure 6:
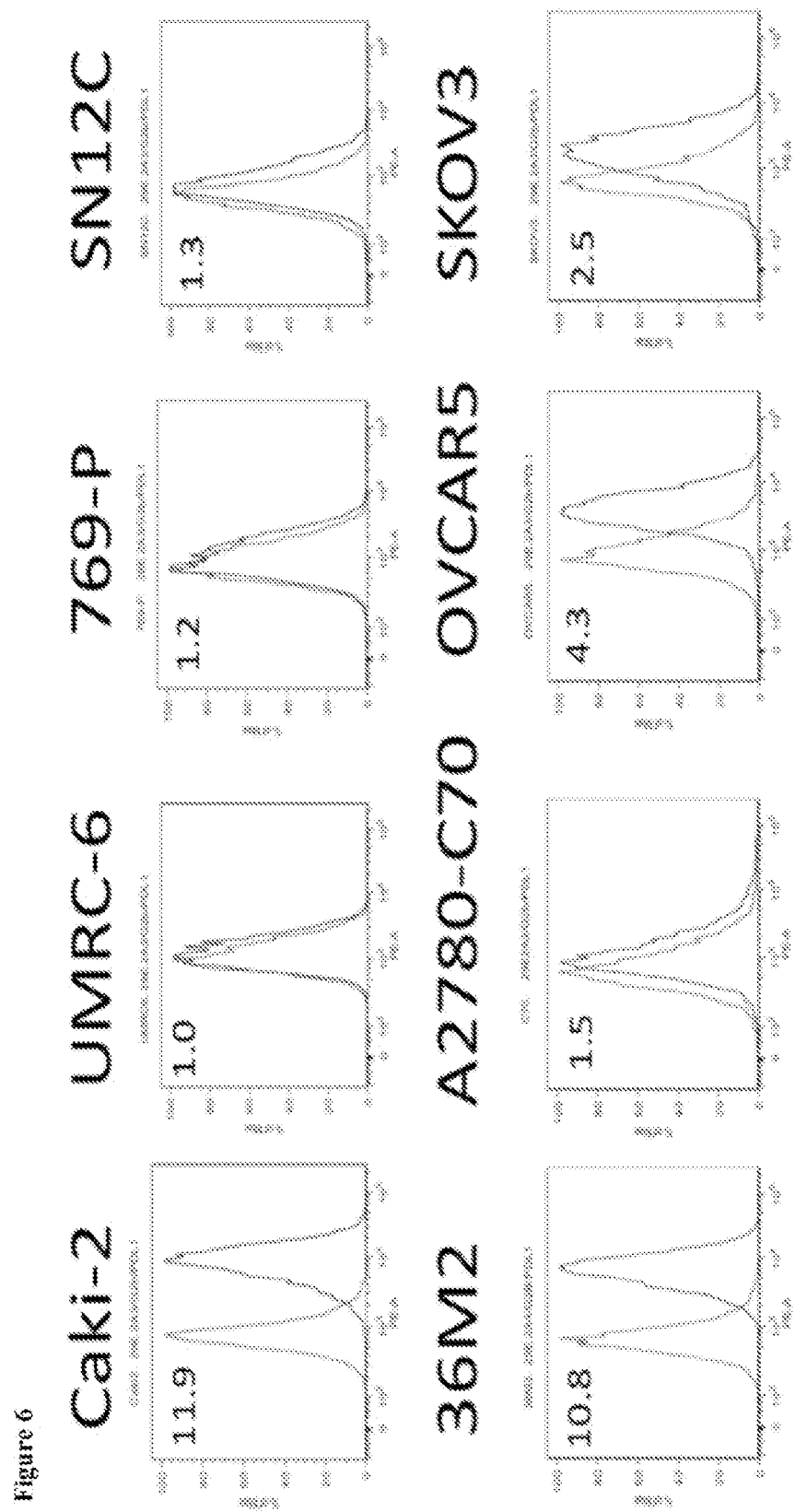
FIG. 6 shows the results of immunophenotyping of RCC and ovarian tumor cell lines with anti-PD-L1 (clone 2A3 results depicted).

Detection of PD-L1 by Western blot also correlates with its surface expression by flow cytometry. Antibodies that block the interaction of PD-1 with its ligand, PD-L1, have been essential for characterizing the co-inhibitory function of this pathway. The interaction between PD-1 and PD-L1 is between the IgV domain in the extracellular domain of each protein. The blocking antibodies useful for in vitro and in vivo functional assays are often excellent for immunophenotyping cells by flow cytometry. The 29E.2A3 antibody, which recognizes the IgV domain of PD-L1, has been used to show PD-L1 expression on Hodgkin lymphoma and a series of breast cancer cell lines (Latchman t al. (2001) *Nat. Immunol.* 2:261-268; Green et al. (2010) *Blood* 116:3268-3277; Chen et al. (2013) *Clin. Cancer Res.* 19:3462-3473). The Hodgkin lymphoma cell lines (HDLM2, L428) and breast cancer cell lines (MDA231, SKBR3) express PD-L1 on the surface, while the diffuse large B-cell lymphoma OC1-Ly1 and the BT474 breast cancer cells do not (Latchman et al. (2001) *Nat. Immunol.* 2:261-268; Green et al. (2010) *Blood* 116:3268-3277). The 29E.2.A3 mAb was used to immunophenotype the renal cell and ovarian carcinoma cell lines. It was found that one of four renal cell carcinoma cell lines and three of four ovarian cancer cell lines screened express PD-L1 on their surface by immunophenotyping (FIG. 6). This pattern of expression and the relative fold of surface expression was confirmed with another anti-PD-L1 mAb. It is described herein that lower expressers by immunophenotyping (under 5 fold over isotype) are under the threshold for detection by Western blot analysis. While flow cytometry proved to be more sensitive than Western blot analysis, the detection by 9A11 correlated with the surface expression of PD-L1, as seen with the 29E.2A3 antibody by flow cytometry of unpermeabilized cells (FIG. 6).

mAb 9A11 also detects surface expression of human PD-L1 in formalin-fixed paraffin embedded tissue by immunohistochemistry. Developing regents for immunohistochemistry (IHC) in FFPE tissues often can be difficult, but is necessary since this is the primary means of assaying patient specimens. It has been previously reported that the 7G11 antibody can detect PD-L1 in FFPE specimen (Chen et al. (2013) *Clin. Cancer Res.* 19:3462-3473) and has shown a staining pattern similar to that previously described with the 5H1 antibody: membranous and cytoplasmic expression (Brahmer et al. (2010) *J. Clin. Oncol.* 28:3167-3175). In FIG. 5, it is demonstrated that unlike 9A11 or 5A4, 7G11 detected multiple bands in Western blot analysis of whole cell lysates. It is unclear whether the multiple bands or the diffuse staining in some specimens by 7G11 is secondary to detecting splice variants of PD-L1, variable glycosylation of PD-L1 or merely a lack of specificity of the antibody. However, there are two anti-PD-L1 antibodies commercially available reported to detect PD-L1 in IHC. Sino Biologics has a rabbit IgG monoclonal antiPD-L1 antibody (clone 15), produced by immunization of the recombinant hPD-L1 (Met 1-Thr 239). Cell Signaling Technologies has recently commercially distributed a rabbit mAb, E1L3, developed against the C-terminal region of PD-L1. This antibody detects the fully glycosylated PD-L1 in Western blot analysis (PD-L1 (E1L3M) XP rabbit mAb (2014) *Cell Signaling Technology*, Product No. mAb 13684). It has been reported to detect PD-L1 by immunohistochemical and immunofluorescent analysis, as well as flow cytometry when cells are permeabilized.

Many hematologic and solid tumors, including melanoma, carcinoma, sarcoma, and lymphoma, can overexpress PD-L1 (Brown et al. (2003). *J. Immunol.* 170:1257-1266; Latchman et al. (2001) *Nat. Immunol.* 2:261-268). This may be a mechanism by which tumors can intrinsically tolerize T cells and evade an anti-tumor immune response. Exploratory analysis of PD-L1 (B7-H1) expression on solid tumors by immunohistochemical analysis (IHC) with the murine anti-human B7-H1, clone 5H1, as previously described in Thompson et al. (2006) *Cancer Res.* 66:3381-3385, was possible with tumor specimen from nine patients in the pilot Phase I study of the anti-PD-1 blocking antibody nivolumab (Brahmer et al. (2010) *J. Clin. Oncol.* 28:3167-3175). PD-L1 was expressed by tumor cells in 3 patterns: cytoplasmic, membranous, or none. In this analysis the membranous expression of PD-L1 on tumor cells was associated with response to anti-PD-1 treatment. Over the past 15 years numerous anti-PD-L1 antibodies have been developed and few have been compared directly. Many tumors had increased expression of PD-L1 with a cytoplasmic pattern by IHC in some of the early publications with older antibodies such as 29E.2A3. A strong membranous pattern of PD-L1 was typically only visualized in tissue with the highest expression (i.e., syncytiotrophoblasts of the placenta) (Brown et al. (2003) *J. Immunol.* 170:1257-1266). Thus, a major goal described herein is to develop better antibodies to answer clinically relevant question: antibodies that are both sensitive, specific, and recognize antigen in FFPE tissue. The pattern of IHC in 4 different tumor types (Hodgkin lymphoma. Diffuse large B cell lymphoma, renal cell carcinoma, and lung adenocarcinoma) using 4 different anti-PD-L1 antibodies: 7G11, Sinobiologies (Sino015), 9A11 and E1L3 is compared.

Classical Hodgkin lymphoma is an excellent example of a blunted immune response: expression of PD-L1 by malignant cells and immune evasion, despite a highly inflammatory microenvironment. There are many means of increasing PD-L1 tumor expression. Unlike many B-cell non-Hodgkin lymphoma, the classical Hodgkin lymphoma (cHL) Reed-Sternberg cells and mediastinal large B-cell lymphoma (MLBCL) can express high levels of PD-L1 and PD-L2 (Green et al. (2010) *Blood* 116:3268-3277). Genetic analysis has found a 9p chromosomal copy frequently described in cHL and MLBCL. Not only does the amplification of neighboring genes encoding PD-L1 and PD-L2 at the 9p24.1, result in high expression of these ligands, but upstream of PD-L1 by 322 kilobases Janus kinase 2 (JAK2) is encoded, amplified, and further upregulated PD-1 ligand expression through IFN-gamma (Green et al. (2010) *Blood* 116:3268-3277). Both Sinobiologic (Sino015) and 7G11 recognize the ectodomain of PD-L1. Both stain the Reed Sternberg cells, but both have marked cytoplasmic staining within the cytoplasm of the surrounding sea of lymphocytes (FIG. 7D, intermediate with Sino015, and 7B, high with 7G11) relative to the staining of the Reed Sternberg cells with both 9A11 and E1L3 (FIGS. 7A-7C, respectively). With less cytoplasmic staining in the infiltrating lymphocytes with 9A11 and E1L3, it is easier to distinguish the membranous staining of some of the PD-L1 positive immune infiltrate surrounding the HL, primarily on the monocytic infiltrate. In comparison to HL, a series of diffuse large B cell lymphoma did not express PD-L1 on its surface by flow cytometry (Green et al. (2010) Blood 116:3268-3277). It was determined herein that PD-L1 was not expressed in whole cell lysates of DLBCL cell line OCI-LY-1 (FIG. 5). Diffuse large B-cell lymphoma (DLBCL) also proved to be a negative control for 9A11 or E1L3 as the IHC analysis showed no membranous stain and little to no cytoplasmic staining (FIGS. 7M and 7O, respectively). However, significantly higher cytoplasmic staining was observed with Sino than 7G11 (FIGS. 7P and 7N, respectively). Renal cell carcinoma and lung adenocarcinoma show distinctly membrane staining with 9A11 (FIGS. 7E and 7I) and E1L3N antibodies (FIGS. 7G and 7K). Renal cell carcinoma and lung adenocarcinoma showed weak cytoplasmic staining and weak extracellular staining with the 7G11 (FIGS. 7F and 7J) and Sino015 (FIGS. 7H and 7L) antibodies and this was largely absent with the 9A11 and E1L3N antibodies.

PD-1 blockade has shown benefit in patients with non-viral mediated tumors (Seiwert et al. (2014) J. Clin. Oncol. 32:5s (supp): abstract 6011). PD-L1 may be induced in tumors by activated various oncogenic pathways, such as JAK2 or Akt pathways (Marzec et al. (2008) Proc. Natl. Acad. Sci. U.S.A. 105: 20852-20857; Parsa et al. (2007) Nat. Med. 13:84-88). In both non-small cell lung cancer and renal cell carcinoma, it has been demonstrated herein that the 9A11 and E1L3 stain tumors cells and immune cells with much lower stromal staining than Sinobiologics and 7G11 mAbs (FIGS. 7E-7L). Also, in sections of the renal cell carcinoma (RCC) tumor, the 9A11 mAb detects the membranous expression of PD-L1 but the 7G11 mAb recognizes both membranous and cytoplasmic PD-L1 (FIGS. 7Q-7R).

The role of PD-L1 as a predictive biomarker in the field of immune checkpoint inhibition has garnered much enthusiasm since the preliminary finding original suggested its role. However, comparing findings in later clinical correlative studies has proven to be a significant conundrum. PD-L1 tumor expression with the 28-8 clone and 22C3 clone of anti-PD-L1 antibody is associated with increased response to PD-1 blockade with nivolumab and pembrolizumab, respectively. With a third antibody, Genentech/Roche has found that PD-L1 expression on the immune infiltrate is associated with responsiveness to anti-PD-L1 antibody, MPDL3280A. However with all three assays, a fraction of PD-L1 "negative" tumors respond. Whether this negative-tumor response is due to heterogeneity of the tumor, technical limitation of automated assay, or differences in the affinity for PD-L1 expressed and modified by different cells has yet to be clarified. Establishing highly sensitive and specific reagents are essential for better understanding the biology of PD-L1 and its potential role in clinical medicine. It is demonstrated herein that antibodies directed against either the extracellular domain or the cytoplasmic regions of PD-L1 result in disparate patterns of expression by IHC. The membranous pattern of expression is best delineated in IHC with the antibodies directed against the cytoplasmic tail, 9A11 and E1L3. The 9A11 antibody is also highly sensitive and specific for PD-L1 in Western blot analysis and correlates with surface expression of PD-L1 in these cell lines by flow cytometry. mAbs 9A11 and E1L3 result in low background, most evident in the IHC of DLBCL. The cytoplasmic expression of PD-L1 may prove to be clinically relevant, as a potentially recruitable reserve of PD-L1, which may be induced with stress, treatment, transformation of tumor. However, it appears that both 7G11 and Sino lack the specificity necessary for stringent analysis of tumors.

Facilitating delineation of membranous versus cytoplasmic PD-L1 appear to also better distinguish tumor cells, stroma and macrophage. Distinguishing PD-L1 on the tumor and infiltrating macrophage is believed to be a means of delineating distinct groups of tumors, more likely to respond to PD-1 pathway blockade. Increased tumor-associated macrophage has been associated with inferior outcomes in cHL (Tan et al. (2012) Blood 120:3280-3287; Steidl et al. (2010) N. Engl. J. Med. 362:875-885). As discussed above, PD-L1 positive tumors, immune infiltrate or tumor surface expression, in some solid tumors has been associated with improved response to PD-L1 or PD-1 blockade, respectively (Gandhi et al. (2014) AACR Annual Meeting, p. CT105; Soria et al. (2013) European Cancer Congress, abstract 3408). Better regents will optimally allow development of better algorithms for assessing potential response to these therapies.

Example 2: PD-L1 Expression in Primary Clear Cell Renal Cell Carcinomas (ccRCCs) and their Metastases Clinical trials evaluating anti-PD-1 and anti-PD-L1 antibodies (Abs) in ccRCC have shown efficacy in a subset of patients. Tumor PD-L1 expression increases the likelihood of benefit with anti-PD-1 Ab, but fails to identify all responders. One explanation for these results is that predictive biomarkers are usually evaluated in the primary tumors, which may not accurately reflect expression in the metastases (mets) that are targeted by therapy. Accordingly, PD-L1 expression was compared in a series of ccRCCs and their mets.

Formalin-fixed paraffin-embedded tissue blocks from 33 primary ccRCCs and corresponding lymph node or distant mets were retrieved. Multiple areas of the primary tumors, including areas of predominant and highest Fuhrman nuclear grade (FNG), were selected for analysis. Slides were immunostained with a validated mouse monoclonal anti-PD-L1 Ab (405.9A11). Membranous expression in tumor cells was quantified using an H-score and a case was considered positive when any tumor cell positively was detected. For expression in intratumoral immune cells, a combined score based on the extent of inflammatory infiltrate and percentage of positive cells was used.

PD-L1 expression in tumor cells of primary tumors and corresponding mets is summarized in Table 3.

TABLE 3

|  |  | Metastases | | |
|---|---|---|---|---|
|  |  | PD-L1− | PD-L1+ | Total |
| Primary Tumors | PD-L1− | 21 | 2 | 23 |
|  | PD-L1+ | 3 | 7 | 10 |
| Total |  | 24 | 9 | 33 |

The pattern of PD-L1 staining was highly heterogeneous in the primary tumors and was restricted to areas of highest FNG. The staining was more homogeneous in the mets. In the 12 cases with positive primary tumors and/or mets, PD-L1 expression in tumor cells tended to be higher in the mets (median average H-score=4.5) compared to the primary tumors (median average H-score=1.3) (p=0.06). No statistically significant difference was found in PD-L1 expression in immune cells between primary tumors and their mets (p>0.5). Thus, discordant expression of PD-L1 between the primary tumor and their mets was detected in 5/33 (15%) of cases indicating that accurate assessment of predictive biomarkers for PD-1 blockade in ccRCC could require analysis of metastatic lesions.

Example 3: Association of PD-L1 Expression on Tumor Infiltrating Mononuclear Cells and Overall Survival in Patients with Urothelial Carcinoma In the United States, there were more than 72,000 new cases of urothelial carcinoma (UC) in 2013 with 30% of initial cases presenting with muscle-invasive disease (Stein et al. (2001) *J. Clin. Oncol.* 19:666-675). Close to 50% of those who are diagnosed with muscle invasive disease will develop metastatic disease. Metastatic UC remains largely incurable and the mortality rates have not changed substantially over the past two decades (Kaufmann et al. (2009) *Lancet.* 374:239-249). Although cisplatin-based cytotoxic chemotherapy has led to improved clinical outcomes, the median OS is 14-15 months and no effective salvage treatment options are available. Many targeted therapies have been also studied in advanced UC (Pons et al. (2014) *Exp. Opin. Invest. Drugs* 23:115-124), besides the limited population with specific genomiet alterations that are druggable (Iyer et al. (2013) *J. Clin. Oncol.* 31:3133-3140), these agents have produced limited clinical activity and when responses occur, they are usually transient. Therefore, novel therapeutics are urgently needed.

In the non-metastatic and metastatic setting, there are many different clinical and pathological features that serve as prognostic factors. To date, there have not been any validated and consistently established immunologic markers that can help survival. In patients with localized muscle-invasive UC, pathologic stage and nodal status are the most important prognostic factors for progression and overall survival (OS) (Sternberg et al. (2007) *Urology* 69:62-79). In the metastatic setting, clinical factors, such as performance status, visceral metastases, hemoglobin level, or liver metastases have been used to prognosticate the outcome in both first and second line (Bellmunt et al. (2010) *J. Clin. Oncol.* 28:1850-1855). Although The Cancer Genome Atlas (TCGA) has provided insights on the genomic profile of urothelial tumors, potentially opening new avenues for prognosis and therapy (Cancer Genome Atlas Research N. *Nature* (2014) 507:315-322), its clinical application is still in its infancy.

Non-muscle invasive UC has been recognized as an immunogenic tumor for a long time (Gueguen et al. (1998) *J. Immunol.* 160:6188-6194). Tumor infiltrating mononuclear cells (TIMC) appear to be involved in the local anti-tumor responses (Bohle et al. (2003) *J. Urol.* 170:964-969). Based on this rational, immunotherapy with *Bacillus* Calmette-Guerin (BCG) has been widely used to stimulate the immune system in preventing local recurrences and tumor progression in high grade/CIS non-invasive disease (Sylvester et al. (2005) *J. Urol.* 174:86-92).

Recently, blocking immune checkpoint molecules with monoclonal antibodies has emerged as a promising strategy in advanced urothelial cancer treatment (Mellman et al. (2011) *Nature* 480(7378):480-489). The interaction of programmed cell death-1 (PD-1) on T cells with its ligand PD-L1 (B7-H1) on tumor cells and immune cells limits T cell-mediated immune responses (Keir et al. (2008) *Annu. Rev. Immunol.* 26:677-704). Therefore, it is believed that the PD-1/PD-L1 signaling pathway plays an important role in immune system escape by the tumor (Drake et al. (2014) *Nat. Rev. Clin. Oncol.* 11:24-37). PD-L1 has been shown to be expressed in several malignancies including UC (Table 4; Brown et al. (2003) *J. Immunol.* 170:1257-12566; Konishi et al. (2004) *Clin. Cancer Res.* 10:5094-5100; Ghebeh et al. (2006) *Neoplasia.* 8(3): 190-198; Hamanishi et al. (2007) *Proc. Natl. Acad. Sci. U.S.A.* 104:3360-3365; Inman et al. (2007) Cancer 109:1499-1505). In addition, it has been suggested that higher PD-L1 expression in tumor cell membrane or tumor infiltrating immune cells is associated with different clinico-pathologic features and clinical outcome in multiple different tumor types (McDermott et al (2013) *Cancer Med.* 2:662-673). However, the prognostic impact of this biomarker has not been established across different tumor types. Recently, blocking PD-L1 signaling in metastatic UC has shown encouraging efficacy, with improved responses in those patients testing PD-L1 positive in TIMC. This has led to the suggestion that PD-L1 expression can serve as a potential predictive biomarker for responsiveness to anti-PD-L1 therapy.

It has been determined herein that PD-L1 expression is correlated with clinico-pathological features, as well as OS, in a large series of patients with UC as well as overall survival including patients who developed metastatic disease and were subsequently treated with platinum based chemotherapy (M1).

Materials and Methods a. Patients and Samples

A total of 160 patients with UC from two institutions, Dana-Farber Cancer Institute, Boston, US, and Hospital del Mar, Barcelona, Spain were identified. Formalin fixed paraffin-embedded (FFPE) blocks were retrieved from the Departments of Pathology. FFPE specimens were taken from radical cystectomy or transurethral resection of bladder tumor (TURB). Baseline clinico-pathological characteristics including smoking history, prior BCG treatment, TNM stage at diagnosis, copy number variation (CNV) at chromosome 9, prognostic factors in patients with metastatic disease, and clinical follow up data were retrospectively collected from the DFCI database. Institutional Review Board approval was obtained at both institutions before data acquisition and tumor staining.

b. Immunohistochemistry

Figure 8:
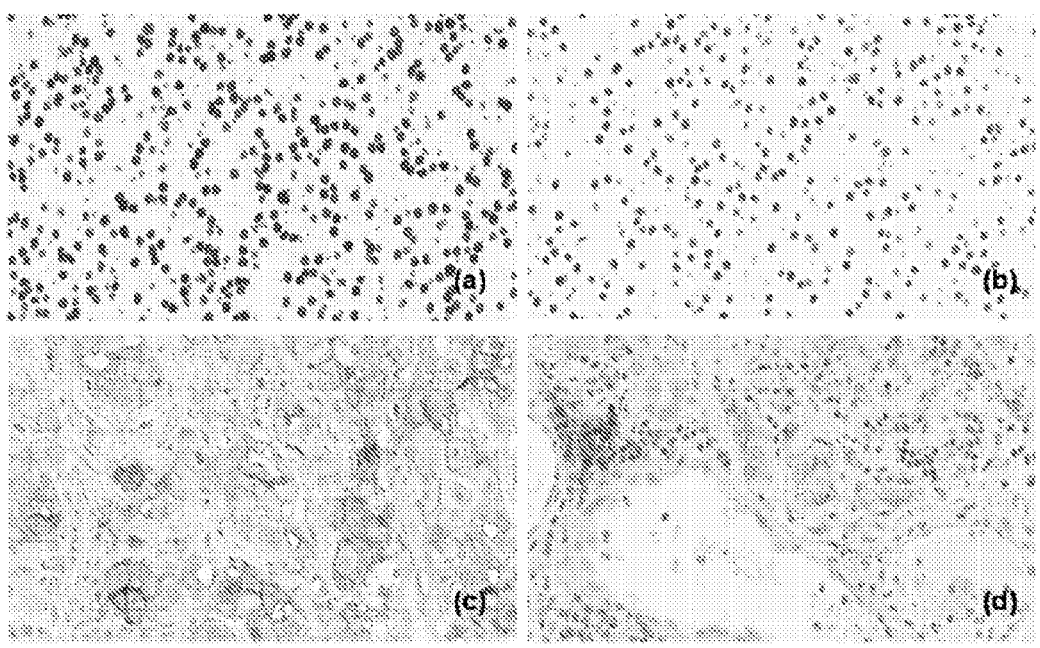
FIGS. 8A-8D show the results of FFPE samples (FIG. 8A: positive control—PD-L1 positive.

PD-L1 expression was evaluated by IHC using a mouse monoclonal anti-PD-L1 antibody (405.9A11) developed in Dr. Gordon Freeman's laboratory (Dana-Farber Cancer Institute, Boston, Mass.) (FIG. 8). This antibody attaches to the PD-L1 ligand in the cytoplasmic domain, providing a clearer stain on the membrane of cells. The immunohistochemical assay was validated using FFPE cell line controls known to be positive or negative for PD-L1 expression by flow cytometry (Green et al. (2010) *Blood* 116:3268-3277). A tissue microarray (TMA) was constructed with all UC samples. Each tumor sample in the TMA had three cores punched per tumor sample to represent tumor heterogeneity. The TMA also included normal urothelium tissue cores. The TMA was stained with the anti-PD-L1 antibody (final concentration of 3.25 ug/ml) on a Benchmark XT autostainer (Ventana Medical System, Tucson. Ariz.) using standard antigen retrieval (CC1 buffer, pH8.0, #950-124, Ventana). UltraView Universal DAB Detection kit (#760-500, Ventana) was used according to the manufacturer's instruction. Counterstaining was performed as part of the automated staining protocol using hematoxylin (#760-2021. Ventana). After staining, slides were washed in soapy water and distilled water, dehydrated in graded alcohol and xylene, mounted and cover slipped.

c. Scoring of PD-L1 Expression

For each sample, the percentage of TIMCs infiltrate, and tumor cells or TIMCs with membranous expression was determined by two independent pathologists (SS and MC) blinded to clinical data. PD-L1 tumor positively was defined as ≥5% of tumor cell membrane staining. The extent of TIMCs was assessed in hematoxylin and eosin-stained slides and recorded as absent (0), focal (1), mild (2), moderate (3) and severe (4) with score 0 or 1 considered negative. The extent of PD-L1-positive TIMCs was also assessed using the same scoring scale (0-4) and samples with a score of 2-4 were considered PD-L1-positive. Seventeen samples were non-evaluable for TIMC extent or PD-L1 staining in TIMC.

d. Recurrent Copy Number Alterations

Array comparative genomic hybridization was performed on 71 samples as described in Riester et al. (2014) *Clin. Cancer Res.* 20:1873-1883. Normalized copy number data were segmented using GLAD with default parameters available in GenePattern version 3.3.3. Genomic Identification of Significant Targets in Cancer (GISTIC) software (Mermel et al. (2011) *Genome Biol.* 12:R41) (v2.0.12) was then used to identify regions of the genome that were significantly gained or deleted across a set of samples. The software estimated false discovery rates (q-values), as well as potential targets (drivers) of the aberrations. Copy numbers of significantly gained or deleted regions (q-value <0.25) were dichotomized based on the standard GISTIC cutoffs for amplifications or deletion (log base 2 ratio >0.9 or <−1.3, respectively). For this analysis, only GISTIC regions on chromosome 9 were analyzed.

e. Statistical Analysis

The primary objective of this study was to correlate the levels of PD-L1 expression with overall survival (OS) in patients with metastatic disease and who received chemotherapy in the metastatic setting. The secondary endpoints were to correlate PD-L1 expression with clinico-pathological features. Patient clinical and pathological characteristics were summarized as numbers and percentage. OS was defined as the time period between the date of the first chemotherapy application and the date of death, or censored on the date of last follow up. The time point for current smokers was at the time of cystectomy. Current and former smokers were combined into the smokers' category for analysis. Fisher's exact tests were used to assess the associations of smoking status, use of BCG with PD-L1 positively in tumor cells and TIMCs. Cox regression model was used to assess the association of PD-L1 positively and TIMC with OS in both univariate and multivariable analysis adjusting for ECOG status and whether patients had visceral disease or not. Hazard ratio and 95% CI were also listed. All statistical computations were performed using SAS v.9.2 (SAS Institute Inc., Cary, N.C., USA) and a p value (two-sided) <0.05 was considered statistically significant.

Results

Figure 9:
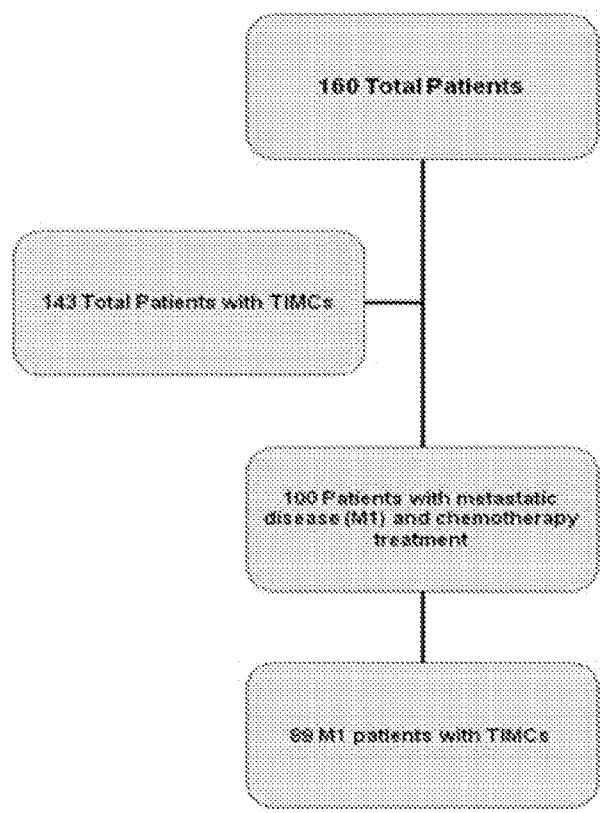
FIG. 9 shows a patient flowchart schematic.
Figure 10:
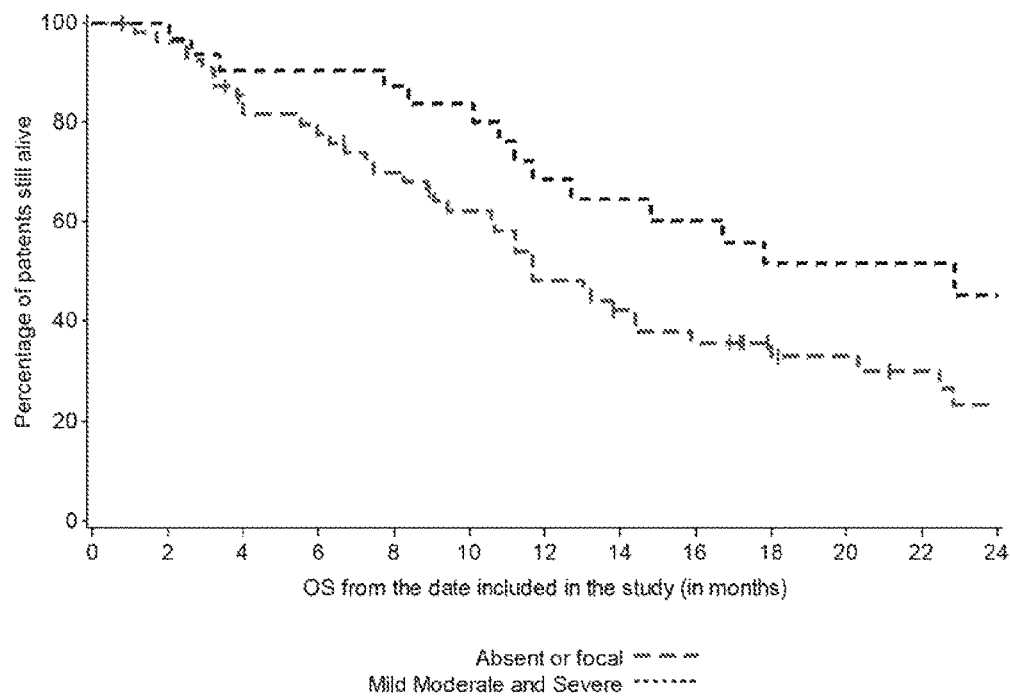
FIG. 10 shows the results of PD-L1 expression relative to TIMC and OS.
Figure 11:
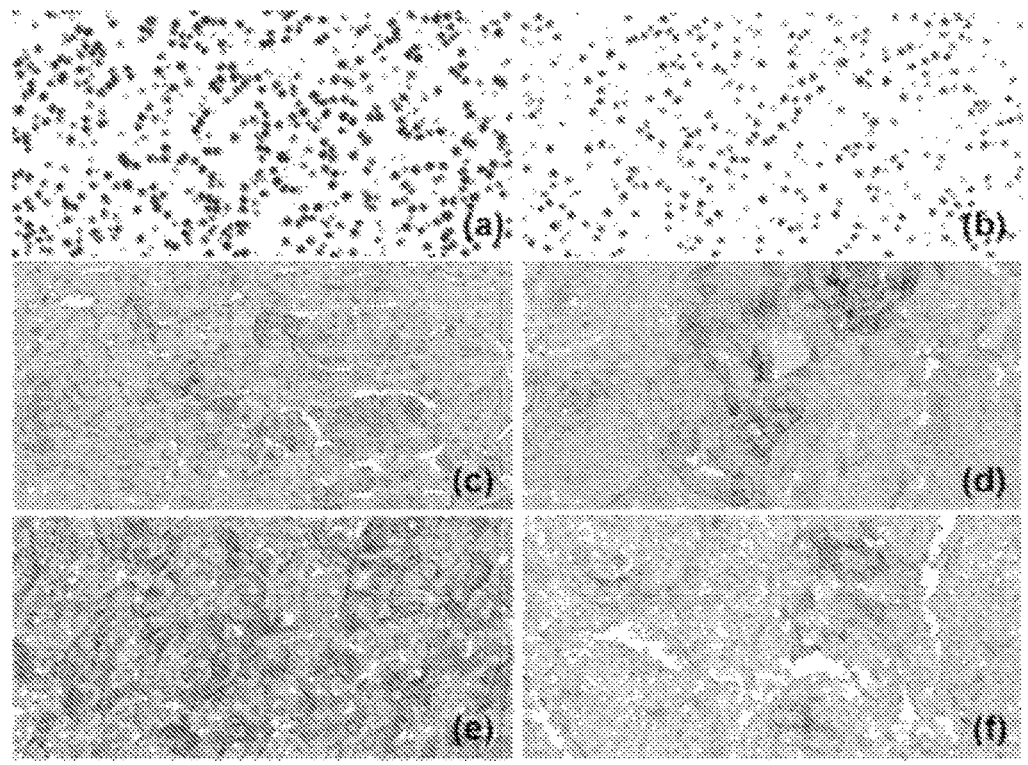
FIGS. 11A-11F show PD-L1 expression in FFPE samples (FIG. 11A: positive cell line control.

Patient and tumor characteristics are described in Table 4. One hundred and sixty patients had tumor samples and adequate clinical data to be evaluated for PD-L1 expression in tumor cells. Among the 160 total patients, 143 had TIMCs in tumor samples and were evaluable for PD-L1 expression in TIMCs. Out of the 160 patients, 100 patients developed metastatic disease and were treated with platinum based therapy (M1). Out of the 10 M1 patients, 89 had TIMCs in their tumor sample and were evaluable for PD-L1 expression in TIMCs (M1$^{+TIMC}$). Patient groups are summarized in FIG. 9.

TABLE 4

Patient characteristics

| Clinico-pathological features | | All Cohort (N = 160) N (%) | Patients with Metastatic Disease (N = 100) N (%) |
|---|---|---|---|
| Staging | Non-invasive Tumors | 23 (14.4) | |
| | T2 | 60 (37.5) | |
| | T3 | 57 (35.7) | |
| | T4 | 16 (10) | |
| | Not Available | 4 (2.5) | |
| Visceral Disease | Yes | | 47 (47%) |
| | No | | 53 (53%) |
| ECOG PS | 0 | | 35 (35%) |
| | 1 | | 58 (58%) |
| | 2 or 3 | | 7 (7%) |
| Chromosome 9 loss | Yes | | 5 (5%) |
| | No | | 66 (66%) |
| | Unknown | | 29 (29%) |
| PD-L1 Expression on Tumor Cell Membrane | Negative (<5%) | 128 (80) | 86 (86%) |
| | Positive (≥5%) | 32 (20) | 14 (14%) |
| Extent of TIMC | Absent | 3 (1.9) | 2 (2%) |
| | Focal | 43 (26.9) | 32 (32%) |
| | Mild | 50 (31.2) | 28 (28%) |
| | Moderate | 34 (21.2) | 21 (21%) |
| | Severe | 13 8.1) | 6 (6%) |
| | Not Available | 17 (10.6) | 11 (11%) |
| PD-L1 Expression in TIMC* | Absent | 34 (1.9) | 26 (26%) |
| | Focal | 51 (26.9) | 30 (30%) |
| | Mild | 42 (31.2) | 23 (23%) |
| | Moderate | 13 (21.2) | 8 (8%) |
| | Severe | 3 (10.6) | 2 (2%) |
| | Not Available | 14 (8.9) | 11 (11%) |

*Patients with Absent TIMC were not stained for PD-L1 in TIMC a. PD-L1 Expression on Tumor Cell Membrane or Tumor Infiltrating Mononuclear Cells (TIMCs)

In total, 160 patients were analyzed for PD-L1 expression on tumor cells membranes. PD-L1 expression was negative in 128 patients (80%) and positive in 32 patients (20%). In the M1 subset, (n=100) PD-L1 expression was negative in 86 (86%) and positive in 14 patients (14%) (Table 4).

Seventeen patients (10.6%) were not evaluable for TIMCs and were not included in the PD-L1 expression analysis. Out of the 143 patients with TIMCs present, PD-L1 expression in TIMCs was scored as absent (0) in 34 patients (21.3%), focal (1) in 51 patients (31.9%), mild (2) in 42 patients (26.3%), moderate (3) in 13 patients (8.1%), and severe (4) in 3 patients (1.9%). PD-L1 expression in TIMCs was considered negative (0 or 1) in 85 out of 157 patients (63%) and positive (2-4) in 58 patients (37%).

Among the M1$^{+TIMC}$ subset (n=89), PD-L1 expression in TIMC were scored as absent (0) in 25 patients (28.1%), focal (1) in 30 patients (33.7%), mild (2) in 23 patients (25.8%), moderate (3) in 8 patients (9.0%) and severe (4) in 2 patients (2.2%). PD-L1 in TIMCs expression was considered negative (0-1) in 56 out of 89 patients (63%) and positive (2-4) in 33 out of 89 patients (37.1%) (Table 4).

b. Association of PD-L1 Expression and Overall Survival in Patients with Metastatic Disease In the M1$^{+TIMC}$ subset, the presence (score of 2-4) versus the absence (score of 0-1) of TIMC infiltrate was found to be significant in terms of longer overall survival (11 months vs. 18 months p=0.02). Positive PD-L1 expression (score of 2-4) in TIMC was significantly associated with longer OS (12 vs. 23 months) in both univariate (p=0.04) and multivariable analysis (p=0.0007) (adjusting for ECOG status and visceral disease) (Table 8 and FIG. 9). PD-L1 expression in tumor cell membrane was not associated with OS (p=0.45) (Table 8). Median follow up was 25 months for M patients.

c. Association of PD-L1 Expression and Staging

Overall, 23 patients had non-muscle invasive bladder cancer (T0 and T1) and 133 patients had high grade muscle invasive bladder cancer (≥T2). Staging was not available in 4 patients. For muscle-invasive UC, TNM stages 11, II and IV at diagnosis were found in 60, 57, and 16 patients respectively. There were no statistically significant differences in PD-L1 expression on TIMC or on tumor cells between non-invasive or invasive bladder cancer (41.8% versus 30%; p=0.53; 8.7% vs. 21.8% p=0.25) (Table 7).

d. Association of PD-L1 Expression and BCG Treatment

Information regarding the prior use of BCG was available in a subset of 69 out of the total 160 patients (43.1%). Out of the 69 patients with information available on prior BCG use, 17 patients (23%) were treated with at least one BCG instillation and 52 (70%) did not receive any BCG therapy (Table 5). All patients who underwent BCG treatment had their last treatment within one year of cystectomy. There was no correlation with prior adjuvant BCG exposure and PD-L1 expression in tumor cell membrane or TIMCs (p=0.12 and p=0.99, respectively) (Table 6).

e. Association of PD-L1 Expression and Smoking Status

In a subset of 73 patients, information on smoking history was available. Out of the 73 patients with smoking history available, 9 (12%) were active smokers, 46 (62%) were former smokers, and 18 (24%) had never smoked. Smoking history was not associated with PD-L1 expression in tumor cell membrane or TIMCs (p=0.86 and p=0.99, respectively) (Table 6).

f. Association of PD-L1 Expression and Copy Number Variation at Chromosome 9

Copy number variation (CNV) data were available for 71 of the 100 M1 patients. CNV at the PD-L1 locus (9p24) was not significant in terms of standard GISTIC parameters (Table 9). The correlation with loss of all of chromosome 9 was also analyzed. Loss of chromosome 9 was defined as having a loss in all four loci (9p11.2, 9p21.3, 9q34.3 and 9p23) that were shown to be significant based on GISTIC cut-offs. Chromosome 9 loss was identified in 5 patients. In this analysis, loss of chromosome 9 did not correlate with PD-L1 expression in tumor cell membrane nor TIMC (p>0.99).

TABLE 5

Smoking history and use of BCG

| Clinico-pathological feature | | Total 74 UC N (%) |
|---|---|---|
| Prior BCG use | Yes | 17 (23) |
| | No | 52 (70) |
| | Unknown | 5 (7) |
| Smoking History | Active smokers | 9 (12) |
| | Former Smokers | 46 (62) |
| | Never Smoked | 18 (24) |
| | Unknown | 1 (1) |

TABLE 6

Association of PD-L1 expression with BCG use or smoking history

| Clinical Features | | PD-L1 expression in tumor cell | | P-value | PD-L1 expression in TIMC | | P-value |
|---|---|---|---|---|---|---|---|
| | | <5% | ≥5% | | Positive | Negative | |
| Prior BCG | No | 35 | 17 | 0.12 | 21 | 27 | 0.99 |
| | Yes | 15 | 2 | | 7 | 8 | |
| Smoking history | Active Smokers | 7 | 2 | 0.86 | 4 | 5 | 0.99 |
| | Former Smokers | 32 | 14 | | 19 | 23 | |
| | Never smoked | 14 | 4 | | 7 | 9 | |

TABLE 7

Association of PD-L1 expression with staging at time of radical cystectomy

| Staging | PD-L1 Expression in Tumor Cell Membrane | | P-value | PD-L1 Expression TIMC | | P-value |
|---|---|---|---|---|---|---|
| | Negative | Positive | | Negative | Positive | |
| Non-Invasive tumors | 21 | 2 | 0.25 | 7 | 3 | 0.53 |
| Muscle-Invasive tumors | 104 | 29 | | 75 | 54 | |

TABLE 8

Association of PD-L1 expression and OS in patients who develop metastatic disease

| | | N | Deaths | Median OS | HR and 95% CI (univariate) | P-value | HR and 95% CI (multivariable) | P-value |
|---|---|---|---|---|---|---|---|---|
| PD-L1 Expression in | Absent, focal | 56 | 37 | 12 | 1.87 (1.02, 3.47) | 0.04 | 3.19 (1.64, 6.22) | 0.0007 |

TABLE 8-continued

Association of PD-L1 expression and OS in patients who develop metastatic disease

|  |  | N | Deaths | Median OS | HR and 95% CI (univariate) | P-value | HR and 95% CI (multivariable) | P-value |
|---|---|---|---|---|---|---|---|---|
| TIMC | Mild, moderate, severe | 33 | 14 | 23 | 1 (reference) |  | 1 (reference) |  |
| PD-L1 expression in Tumor Cell Membrane | <5% | 86 | 52 | 14 | 1.42 (0.57, 3.55) | 0.45 | 1.72 (0.67, 4.40) | 0.26 |
|  | ≥5% | 14 | 5 | Not reached | 1 (reference) |  | 1 (reference) |  |

TABLE 9

Association of PD-L1 expression with stage and Chromosome 9 loss

|  | PD-L1 % tumor | | | PD-L1 MNC cell | | |
|---|---|---|---|---|---|---|
|  | <5% | ≥5% | P-Value | Neg(0-1) | Pos(2-4) | P-value |
| Chromosome 9 Loss |  |  | >0.99 |  |  | 0.53 |
| Without Loss | 58 | 5 |  | 37 | 2 |  |
| Loss | 8 | 0 |  | 23 | 0 |  |
| Stage |  |  |  |  |  | 0.56 |
| 0, 1 |  |  |  | 7 | 3 |  |
| 2, 3, 4 |  |  |  | 75 | 54 |  |

Higher PD-L1 expression in tumor cells has been correlated with both favorable and unfavorable outcome in several malignancies (Zhang et al. (2010) Cell. Mol. Immunol. 7:389-395; Shi et al. (2011) Intl. J. Cancer 128:887-896; Hino et al. (2010) Cancer 116:1757-1766; Schalper et al. (2014) Clin. Cancer Res. 20:2773-2782; Velcheti et al. (2014) Lab. Invest. 94:107-116). In UC, PD-L1 expression on tumor cells has been associated with high grade, stage, and worse outcome in some reports. However, the overall impact of PD-L1 expression on prognosis remains controversial in UC (Gadiot et al. (2011) Cancer 117:2192-2201). No reports have addressed the role of PD-L1 in TIMC. The results described herein are demonstrate that PD-L1 expression in TIMC is correlated with improved OS in patients with UC who developed metastatic disease and were homogeneously treated with platinum based chemotherapy. PD-L1 expression can occur on the tumor cell or on TIMCs. When T cells recognize antigen and become activated, they express cytokines such as interferon-γ which in turn can induce PD-L1 expression on surrounding immune and tumor cells. The expression of PD-L1 on TIMCs is consistent with the idea that these intratumoral lymphocytes are tumor antigen-specific and responding to the tumor.

The correlation between PD-L1 expression in tumors cells and clinical outcome in patients with UC was firstly reported by Nakanishi and colleagues. PD-L1 expression in tumor cell membrane were evaluated in 65 patients with UC and positive PD-L1 expression was significantly associated with worse clinical outcome (higher risk of recurrence and shorter overall survival) (Nakanishi et al. (2007) Cancer Immunol. Immunotherap. 56:1173-1182). In addition, levels of PD-L1 expression were found to be high in inflammatory cells in 13 randomly selected patients.

Recently, Boorjian and colleagues reported that higher PD-L1 expression in tumor cells was associated with the presence of advanced disease in patients with UC. In this study, PD-L1 expression was also correlated with short overall survival in patients with organ-confined UC after radical cystectomy (Boorjian et al. (2008) Clin. Cancer Res. 14:4800-4808). In another series, which evaluated 302 UC patients, PD-L1 expression in tumor cell membrane was not correlated with recurrence, cancer-specific or overall survival. However, in patients with organ-confined UC, higher PD-L1 expression was associated with an increased risk of death (p=0.02) (Xylinas et al. (2014) Eur. J. Surg. Oncol. 40:121-127).

In bladder cancer, based on the potential predictive role recently described for PD-L1 expression on immune cells in patients receiving check point inhibitors, attention has now switched towards the analysis of PD-L1 expression in immune cells instead of tumors cells (Powles et al. (2014) J. Clin. Oncol. 32:5s (supp; abstract 5011). In the study described herein, no association between tumor cell PD-L1 expression and clinical outcome was found. However, in addition to seeing a correlation with higher TIMCs infiltrate and survival, higher PD-L1 expression in TIMCs was statistically correlated with longer OS in the multivariate analysis in patients who developed metastatic disease and subsequently received chemotherapy.

Recently, Topalian and colleagues reported the results from a phase I trial of an anti-PD-1 monoclonal antibody (nivolumab) in solid tumors. Encouraging responses were observed in patients with melanoma, non-small cell lung cancer and RCC. Additionally, the duration of responses appeared to be greater than that observed with systemic chemotherapies or other targeted therapies. A biomarker analysis was conducted in 42 randomly selected patients who were treated with this agent. Among these 42 patients, 25 were considered PD-L1 positive in tumor cell membrane. Objective responses were seen in 36% of PD-L1 positive patients vs. 0% in PD-L1 negative patients (p=0.006) (Topalian et al. (2012) New Engl. J. Med. 366:2443-2454).

Most recently, preliminary results from a phase I study to evaluate the efficacy of MPDL3280A, an anti-PD-L1 mAb, in patients with advanced UC were presented. This study enrolled 67 patients with aggressive features. The overall response rate was 52% with most of the responses ongoing at the cut-off time of analysis. The RR in those patients who express PD-L1 in immune cells was 43% vs. 11% in those who were considered PD-L1 negative (Powles et al. (2014) J. Clin. Oncol. 32:5s (supp; abstract 5011). These results support the rationale of PD-L1 expression in immune cells as a potential predictive biomarker for immunotherapies in UC. However, 27% of patients who stained PD-L1 negative still had a response to MPDL3280A. This highlights the need for better biomarkers for response to anti-PD-L1 therapy. Phase 3 studies across the United States and Europe are currently ongoing and the results regarding efficacy and potential predictors of response are eagerly awaited to confirm these findings.

Treatment with BCG, in patients with high-risk non-invasive tumors has resulted in lower risk of recurrence (Castellano et al. (2012) Cancer Treatment Rev. 38:431-441). The success of BCG in high-risk non-invasive tumors has highlighted UC as an immune sensitive disease. However, the role of immune checkpoints like PD-1/PD-L1 in patients who received this therapeutic strategy remains unclear (Prescott et al. (2000) Clin. Infect. Dis. 31:S91-S93). Inman and colleagues evaluated PD-L1 expression in tumor cells in 280 UC of the bladder. In that study PD-L1 expression was associated with high-grade tumors and tumor infiltration by mononuclear cells (p=0.009 and p=0.004 respectively). Higher PD-L1 expression was seen in 11 out of 12 patients who had BCG-induced pathological inflammatory changes and failed BCG treatment suggesting that tumor cells might be protected from attack by immune cells through immune checkpoints, like PD-L1 (Inman et al. (2007) Cancer 109:1499-1505). Notably, in the analysis described herein, PD-L1 expression was not correlated with prior use of BCG.

The PD-L1 gene is located on chromosome 9p24. Green and colleagues demonstrated that PD-L1 amplification was associated with significantly higher PD-L1 expression on tumor cell membrane of Hodgkin Lymphomas (Green et al. (2010) Blood 116:3268-3277). UC is associated with multiple somatic CNVs, including frequent chromosome 9 loss (Fadl-Elmula et al. (2000) Genes Chromosom. Cancer 29:256-265). Therefore, it was believed that CNV on chromosome 9 may correlate with PD-L1 expression in UC. No correlation was found between copy number changes and PD-L1 expression.

Thus, PD-L1 is widely expressed in tumor cell membrane and TIMC in UC. No significant correlation was found with prior BCG treatment, smoking history, staging, or chromosome 9 copy number changes. However, PD-L1 positively in TIMC and not in tumor cells was significantly associated with better overall survival in those patients who subsequently developed metastatic disease and received treatment with platinum based chemotherapy.

Example 4: PD-L1 Expression in Non-Clear Renal Cell Carcinoma

Renal cell carcinoma (RCC) has been widely recognized as an heterogeneous disease encompassing different histological subtypes (Cohen and McGovern (2005) N. Engl. J. Med. 353:2477-2490). Clear cell RCC (ccRCC) is the most common subtype and accounts for more than 80% of the tumors that arise from the renal epithelium (Choueiri (2011) Hematol. Oncol. Clin. North. Am. 25:xiii-xiv). The remaining renal epithelial malignancies, collectively named as non-clear cell RCC (nonccRCC), include several subtypes such as papillary RCC (10-15%), chromophobe RCC (5%), and the more rare forms, which include as Xp11.2 translocation RCC, unclassified RCC, and collecting duct carcinoma, among others (World Health Organization (WHO), Kidney Cancer—Pathological Classification. 2004).

In RCC, surgery can be curative for localized disease (Janzen et al. (2003) Urol. Clin. North Am. 30:843-852). However, about 30% of patients treated with nephrectomy will still develop systemic metastases. The risk of recurrence has been associated with clinical and pathological factors such as tumor-node-metastasis (TNM) staging and Fuhrman nuclear grading (Zisman et al. (2001) J. Clin. Oncol. 19:1649-1657). Several reports suggested that localized non-ccRCC is more likely to have a favorable prognosis than ccRCC (Heng and Choueiri (2009) J. Natl. Compr. Canc. Netw. 7:659-665). Paradoxically, some series showed that when metastatic, some types of non-ccRCC such as papillary and Xp11.2 translocation RCC (Motzer et al. (2002) J. Clin. Oncol. 20:2376-2381; Bellmunt et al. (2010) J. Clin. Oncol. 28:1850-1855), may have an aggressive clinical course and a shorter overall survival (OS).

Immunotherapy strategies have been used for decades in patients with advanced RCC, with prolonged survival being seen in a very small proportion of patients treated with interferon alpha or high dose IL-2 therapy (Figlin (1999) J. Urol. 161:381-387). Based on the important role of angiogenesis in ccRCC, single-agent therapies blocking the vascular endothelial growth factor (VEGF) or its receptors, as well as the mammalian target of rapamycin (mTOR) produced significant clinical benefit in the majority of metastatic ccRCC, resulting in a median OS of 20-30 months, compared to ~13 months reported with traditional immunotherapy (Motzer et al. (2013) N. Engl. J. Med. 369:722-731; Sonpavde and Choueiri (2013) Urol. Oncol. 32:5-15). Because of their relatively low prevalence and their distinct biology, patients with non-ccRCC have typically been excluded from the pivotal clinical trials of anti-angiogenic and tumor targeted agents (Chowdhury et al. (2011) Hematol. Oncol. Clin. North. Am. 25:853-869). Although some series have suggested that these drugs may also have activity in patients with non-ccRCC, more effective therapies for this patient population are needed (Heng and Choueiri (2009) J. Natl. Compr. Canc. Netw. 7:659-665; Harshman and Choueiri (2013) Cancer J. 19:316-323; Bellmunt and Dutcher (2013) Ann. Oncol. 24:1730-1740; Dutcher et al. (2009) Med. Oncol. 26:202-209).

The levels and clinical significance of PD-L1 expression in non-ccRCC subtypes is still unknown. In the study described herein, PD-L1 expression was determined to be associated with clinical outcome in a large series of patients with non-ccRCC.

Materials and Methods a. Patients and Samples

One hundred and one patients with non-ccRCC (chromophobe RCC, papillary RCC, collecting duct carcinoma and Xp.11.2 translocation RCC) treated surgically at 2 institutions (Brigham and Women's Hospital (BWH) and Mayo Clinic), were identified. For comparative purposes, 20 patients with oncocytoma or angiomyolipoma treated in the same institutions were also evaluated. Formalin fixed paraffin-embedded (FFPE) blocks were retrieved and corresponding slides from all cases were re-reviewed by an expert genitourinary pathologist (SS) at BWH. Baseline clinico-pathological characteristics such as age, gender, tumor size, Fuhrman grade, pathological TNM stage at time of surgery and follow up data were retrospectively collected for patients with non-ccRCC. Uniform data collection templates were used to ensure consistent data. Institutional Review Board approval was obtained before data acquisition and tumor staining.

b. Immunohistochemistry

PD-L1 expression was evaluated by immunohistochemistry using a mouse monoclonal anti-PD-L1 antibody (405.9A11) developed in Dr. Gordon Freeman's laboratory (Dana-Farber Cancer Institute, Boston, Mass.) (FIG. 1). The immunohistochemical assay was extensively validated using FFPE cell line controls known to be positive or negative for PD-L1 expression by flow cytometry (Green et al. (2010)

Blood 116:3268-3277). Four micron-thick tumor sections were stained with an anti-PD-L1 antibody concentration of 3.25 ug/ml, on a Benchmark XT autostainer (Ventana Medical System. Tucson, Ariz.) with standard antigen retrieval (CC1 buffer, pH8.0, #950-124, Ventana). UltraView Universal DAB Detection kit (#760-500, Ventana) was used according to the manufacturer's instruction. Counterstaining was performed as part of the automated staining protocol using hematoxylin (#760-2021, Ventana). After staining, slides were then washed in soap water and distilled water, dehydrated in graded alcohol and xylene, mounted and cover slipped.

c. Quantification of PD-L1 Expression on Tumor Cell Membrane

Membranous expression in tumor cells was quantified semi-quantitatively by two independent pathologists (SS and MC) blinded to clinical outcome. PD-L1 tumor positively was defined as ≥5% tumor cell membrane staining.

d. Quantification of PD-L1 Expression in Tumor Infiltrating Mononuclear Cells (TIMC)

The extent of TIMCs (i.e., lymphocytes and macrophages) was assessed in hematoxylin and eosin-stained slides and recorded as absent (0), focal (1), mild (2), moderate (3) and marked (4). The percentage of PD-L1-positive TIMC was evaluated independently by two pathologists (SS and MC), according to three categories (0%=0, <5%=1, ≥5%=2). An adjusted score representing PD-L1 expression was calculated multiplying the percentage of TIMC that stained positive for PD-L1 and the extent of mononuclear cell infiltration.

c. Statistical Analysis

The primary objective of this study was to characterize the PD-L1 expression in patients with non-ccRCC and to correlate the levels of expression with clinico-pathological features as well as disease outcomes. Two endpoints were analyzed: 1) TTR, defined as time from diagnosis to the date of development of metastatic disease and 2) OS, defined as time from diagnosis to death. In the absence of an event, the endpoints were censored at last follow-up time. Patient and tumor characteristics were summarized descriptively. PD-L1 tumor positively was defined as ≥5% tumor cell membrane staining. For PD-L1 expression in TIMCs, any score greater than zero was considered positive. Comparisons between PD-L1 expression and clinicopathological features were evaluated using Chi-square or fisher's exact test (when sample size was small) for categorical variables and Wilcoxon rank-sum test for continuous variables. Kaplan-Meier method estimated the distribution of TTR and OS by the PD-L1 positively. Cox proportional regression assessed the associations with hazard ratio and 95% conference interval (CI). PD-L1 expression in patients with benign tumors was reported descriptively and correlations with clinico-pathological features as well as outcome variables were not performed.

All statistical computations were performed using SAS v.9.2 (SAS Institute Inc., Cary, N.C., USA) and a p value (two-sided) <0.05 was considered statistically significant.

Results a. Patients and Tumor Characteristics

Characteristics of patients with non-ccRCC are outlined in Table 10. The study cohort included a total of 101 patients with non-ccRCC. The histological subtypes included chromophobe RCC (n=36), papillary RCC (n=50) and Xp11.2 translocation RCC (n=10) and collecting duct carcinoma (n=5). The median follow-up time was 5 year (inter-quartile-range (IQR): 3.5-6.2), and the median age was 59 years (range 24-81). For non-ccRCC, TNM clinical stages I, II, III and IV at diagnosis were identified in 54, 19, 18 and 9 patients, respectively. Additionally, 47 patients had high Fuhrman grade (III or IV) and 53 had low Fuhrman grade (I or II). In one tumor sample the definition of tumor grade was not precisely possible and it was not reported. The median tumors' size was 4.7 cm (range 2.8-7.7). For comparative purposes, 20 patients with benign kidney tumors were also evaluated for PD-L1 expression. The histological subtypes included oncocytoma (n=13) and angiomyolipoma (n=7). The median tumor's size was 3.2 cm (range 1.9-5.6).

TABLE 10

Non-ccRCC Patient Characteristics

| Characteristic | | Total (n = 101) | |
|---|---|---|---|
| | | No. of Patients | % |
| Gender | Male | 55 | 54 |
| | Female | 46 | 46 |
| Stage | 1 | 54 | 53 |
| | 2 | 19 | 19 |
| | 3 | 18 | 18 |
| | 4 | 9 | 9 |
| | Unknown | 1 | 1 |
| Fuhrman Grade | I/II | 53 | 52.4 |
| | III | 38 | 37.6 |
| | IV | 9 | 9 |
| | Unknown | 1 | 1 |
| Histology | Chromophobe | 36 | 36 |
| | Papillary | 50 | 49 |
| | Translocation | 10 | 10 |
| | Collecting Duct Carcinomas | 5 | 5 |
| Metastatic disease | No | 78 | 77.2 |
| | Yes | 23 | 22.8 |
| PD-L1 Expression in Tumor Cells Membrane | <5% (negative) | 90 | 89.1 |
| | ≥5% (positive) | 11 | 10.9 |
| PD-L1 Expression in Tumor Infiltrating Mononuclear Cells (TIMC) | Score = 0 (negative) | 44 | 43.6 |
| | Score > 0 (positive) | 57 | 56.4 |

| | Median | Min, Max |
|---|---|---|
| Age at Dx (years) | 59 | 24-81 |
| Tumor size (cm) | 4.7 | 0.6-30 | b. PD-L1 Expression in Tumor Cells and Clinic-Pathological Features

Among 101 patients with non-ccRCC, PD-L1 expression in tumor cell membrane was negative in 90 patients (89.1%) and positive in 11 patients (10.9%). Specifically. PD-L1 positively in tumor cell membrane was detected in 2 of 36 (5%) chromophobe RCCs, 5 of 50 (10%) papillary RCCs, 3 of 10 (30%) Xp11.2 translocation RCC, and 1 of 5 (20%) collecting duct carcinomas. PD-L1 positively in tumor cell membrane was significantly associated with higher TNM stage (p=0.01) and Fuhrman grade III/IV (p=0.03) (Table 11). On the other hand, PD-L1 positively was not correlated with gender, age at diagnosis, or tumor size).

TABLE 11

| | | % Positive Tumor Cell Membrane | | | | Tumor Infiltrating Mononuclear Cells | | | |
|---|---|---|---|---|---|---|---|---|---|
| Characteristic | | <5% (negative) (n = 90, 89.1%) n (%) | 5% or more (positive) (n = 11, 10.9%) n (%) | Total (n = 101) n (%) | p-value | Score = 0 (negative) (n = 44, 43.6%) n (%) | Score >0 (positive) (n = 57, 56.4%) n (%) | Total (n = 101) n (%) | p-value |
| Stage | 1 | 52 (58) | 2 (20) | 54 (53) | 0.01 | 24 (55) | 30 (54) | 54 (53) | 0.38 |
| | 2 | 18 (20) | 1 (10) | 19 (19) | | 11 (25) | 8 (14) | 19 (19) | |
| | 3 | 14 (16) | 4 (40) | 18 (18) | | 7 (16) | 11 (20) | 18 (18) | |
| | 4 | 6 (7) | 3 (30) | 9 (9) | | 2 (5) | 7 (12) | 9 (9) | |
| | Unknown | 0 | 1 (1) | 1 (1) | | 0 | 1 (1) | 1 (1) | |
| Fuhrman Grade | I/II | 51 (57) | 2 (18) | 53 (52.4) | 0.03 | 23 (53) | 30 (53) | 53 (52.4) | 0.17 |
| | III | 31 (35) | 7 (64) | 38 (37.6) | | 19 (44) | 19 (33) | 38 (37.6) | |
| | IV | 7 (8) | 2 (18) | 9 (9) | | 1 (1) | 8 (14) | 9 (9) | |
| | Unknown | 1 (1) | 0 | 1 (1) | | 1 (1) | 0 | 1 (1) | |
| Histology | Chromophobe | 34 (94.4) | 2 (5.6) | 36 (36) | 0.1 | 23 (63.9) | 13 (36.1) | 36 (36) | 0.001 |
| | Collecting Duct | 4 (80) | 1 (20) | 5 (5) | | 0 (0) | 5 (100) | 5 (5) | |
| | Papillary | 45 (90) | 5 (10) | 50 (49) | | 20 (40) | 30 (60) | 50 (49) | |
| | Translocation | 7 (70) | 3 (30) | 10 (10) | | 1 (10) | 9 (90) | 10 (10) | | c. PD-L1 Expression in TIMCs and Clinic-Pathological Features

Overall, the extent of TIMCs infiltration was: (absent in 11 patients, focal in 27 patents, mile in 31 patients, moderated in 20 patients and marked in 12 patients. PD-L1 expression in TIMCs was negative (score 0) in 44 patients (43.6%). Fifty-seven patients (56.4%) were considered PD-L1+ in the TIMCs. Among the cases with PD-L1+ TIMCs, 37 patients had expression in less than 5% of immune cells and 20 patients presented expression in more than 5% of immune cells. There was a significant association of histology subtype and PD-L1 expression levels in TIMCs (p=0.001). Specifically, among patients with PD-L1+, 13 of 36 (36%) had chromophobe RCC, 30 of 50 (60%) had papillary RCC, 9 of 10 (90%) Xp11.2 had translocation RCC and 5 of 5 (100%) had collecting duct carcinoma. PD-L1 positively in TIMCs was not significantly associated with TNM stage (p=0.35) or tumor grade p=0.11) (Table 11). In addition, PD-L1 positively in TIMCs did not correlate with gender, age at diagnosis or tumor size.

d. PD-L1 Expression and Clinical Outcome in Non-ccRCC

Figure 12:
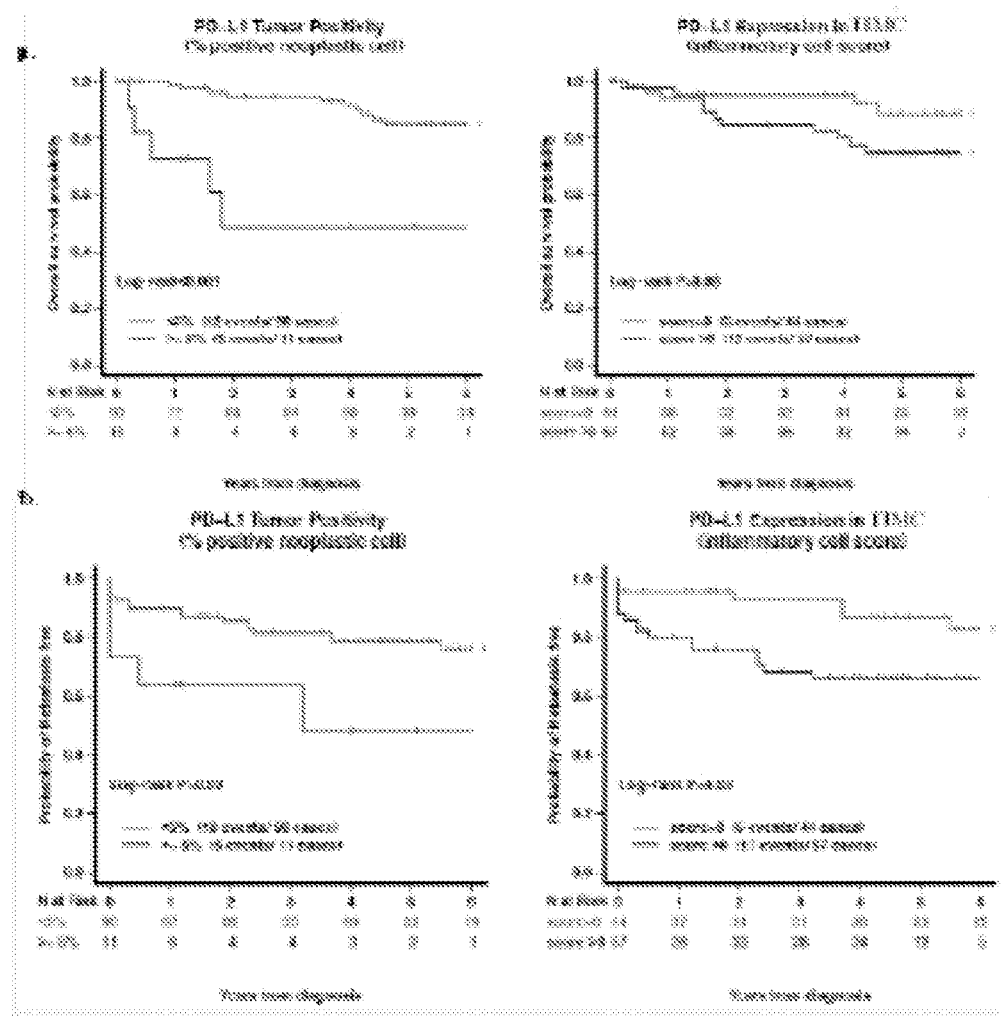
FIGS. 12A-12B show correlation of PD-L1 expression and OS (univariate analysis) in non-ccRCC (FIG. 12A) and correlation of PD-L1 expression and TTR (univariate analysis) in non-ccRCC (FIG. 12B).
Figure 13:
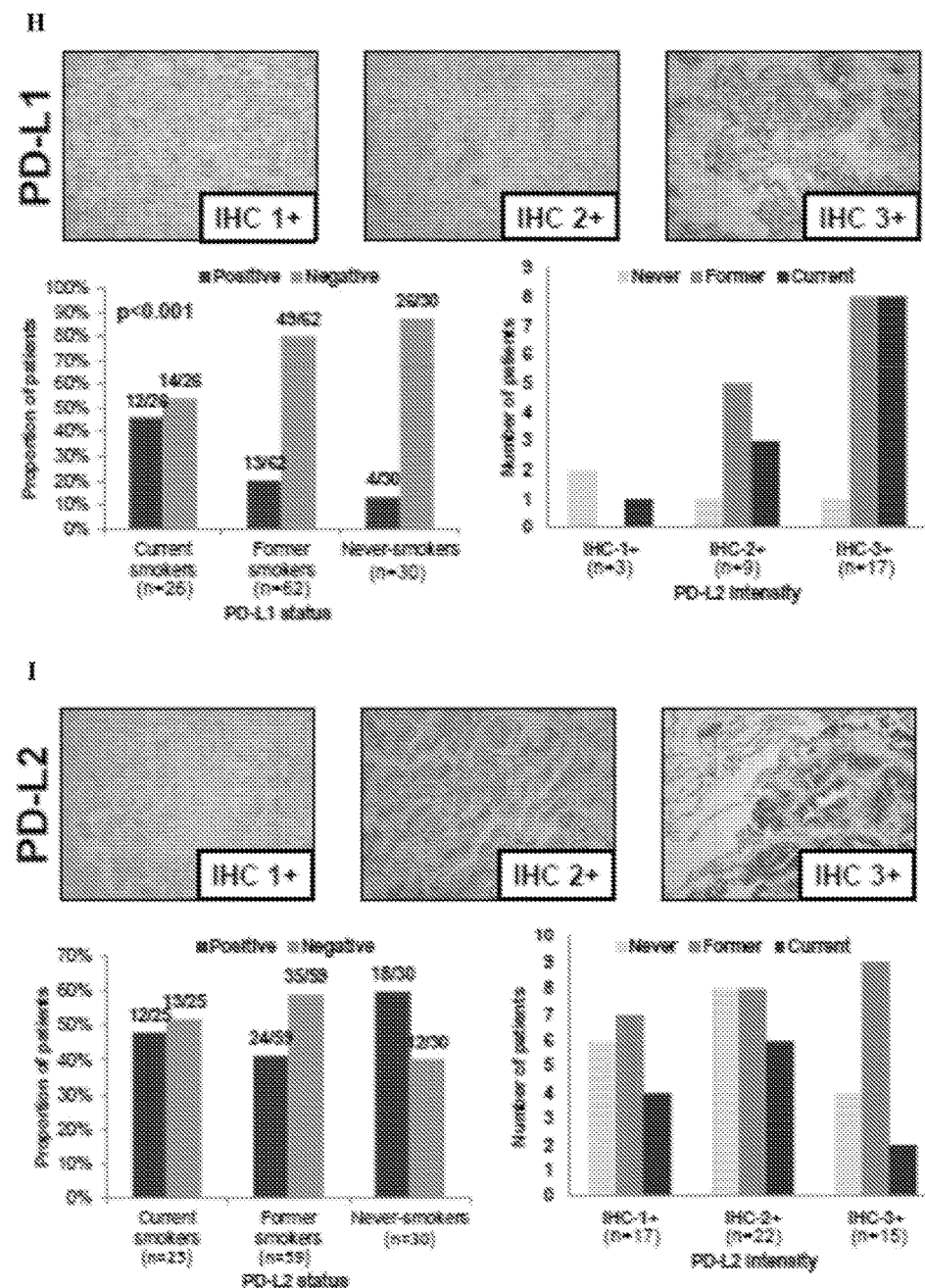
FIGS. 13A-13J show the results of differential expression of LKB1, PD-L1, and PD-L2 in KRAS-mutant non-small cell lung cancer in never-smokers.
Figure 13:
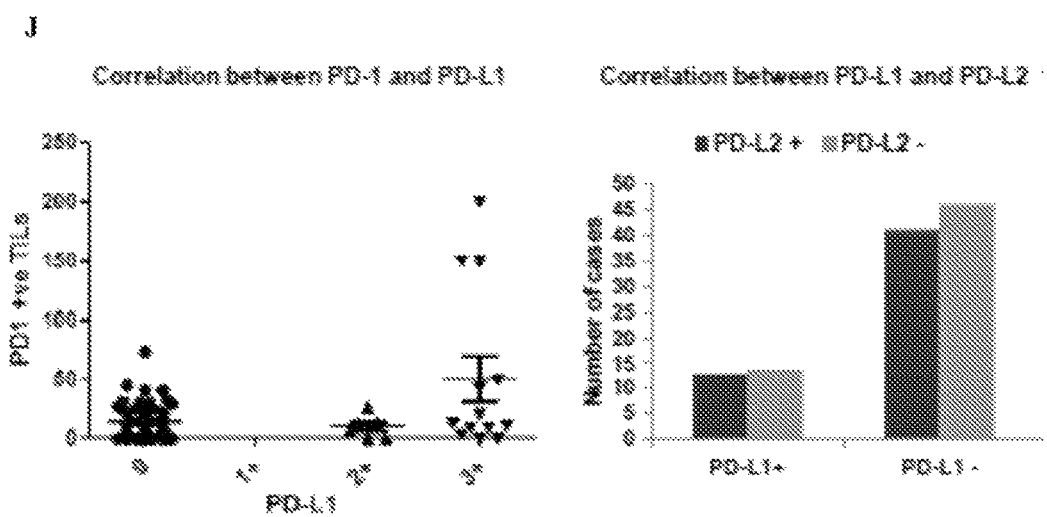

The overall median follow up of the cohort was 5 years, 17 patients died and 24 patients developed distant metastases. Patients with PD-L1+ in tumor cells were significantly associated with increased risk of death (HR=6.41, 95% CI 2.17-18.88; p<0.001) compared to patients with PD-L1 negative in tumor cells. A similar trend was observed when comparing PD-L1 expression in TIMCs, but the result was not statistically significant (HR=2.49, 95% CI 0.86-7.2; p=0.08) (FIG. 12A). In addition, PD-L1+ on tumor cell membrane and TIMCs both were associated with lower TTR (p=0.02 and p=0.03, respectively) (FIG. 12B).

c. PD-L1 Expression in Benign Kidney Tumors

PD-L1 expression in tumor cell membrane was positive in 4 of 13 (30.8%) oncocytomas and 0 of 7 (0%) angiomyolipomas. In addition, 7 of 13 (53.8%) of oncocytoma and 7 of 7 (100%) angiomyolipoma expressed PD-L1 in TIMC (score>0). Correlations with clinicopathological features as well as outcome variables were not performed.

Thompson and colleagues were among the first to describe the PD-L1 expression in ccRCC. In one study of 196 patients, PD-L1 expression was associated with aggressive features, such as higher TNM stage, tumor size or Fuhrman grade and increased risk of cancer-specific mortality (Thompson et al. (2004) Proc. Natl. Acad. Sci. U.S.A. 101:17174-17179). In another study of 306 patients PD-L1+ was seen in 23% of cases. Similarly, PDL1+ tumors were more likely to present adverse pathologic features, including TNM stage III or IV, higher tumor size and Fuhrman grade III or IV (p<0.001 for all), and higher risk of cancer-specific mortality (RR=2.0 95% CI: 1.27-3.15, p<0.003) adjusting for TNM stage and grade (Thompson et al. (2006) Cancer Rev. 66:3381-3385). Interestingly, the correlation between PD-L1 expression and adverse prognostic factors, as well as OS, was identified with PD-L1 expression in both tumor cell membrane and tumor infiltrating lymphocytes (TILs). Based on these studies. PD-L1 expression may be considered as an independent predictor of poor prognosis in ccRCC (Thompson et al. (2007) Clin. Cancer Res. 13:709s-715s).

Overcoming this adaptive mechanism of tolerance with therapies blocking the PD-1 or PD-L1 could restore the effectiveness of T cell responses against tumor cells (Korman et al. (2006) Adv. Immunol. 90:297-339). A phase I study evaluating the safety and efficacy of the anti-PD-1 monoclonal antibody (nivolumab) in patients with advanced cancer produced encouraging tumor responses in patients with RCC and other malignancies.

Moreover, specimens from 42 patients, including 5 patients with RCC were analyzed for PD-L1 expression in tumor cells. Overall, 25 of 42 were considered PD-L1+. Among these 25 patients, 9 (36%) had objective response. On the other hand, none of the patients with PD-L1- expression achieved objective response (p=0.006). These results supported the hypothesis that PD-L1 may be a promising predictive biomarker of response to agents that target the PD1/PD-L1 axis (Topalian et al. (2012) N. Engl. J. Med. 366:2443-2454). Since that landmark study, 2 other studies in RCC specifically showed that patients with PD-L1+ tumors have numerically higher response to agents that target the PD-L1/PD-1 axis than PD-L1 negative tumors, although it is important to note that responses were seen in PD-L1-negative tumors (Cho et al. (2013) Clinical activity, safety, and biomarkers of MPDL3280A, an engineered PD-L1 antibody in patients with metastatic renal cell carcinoma (mRCC). 2013 ASCO Annual Meeting; Choueiri et al. (2014) J. Clin. Oncol. 32:5s (supp.; abstract 5012)).

The study described herein reports PD-L1 expression in non-ccRCC and its correlation with clinical outcome. Consistent with previously published ccRCC studies, PD-L1 expression in tumor cell membrane was correlated with higher Fuhrman grade or TNM stage in patients with nonccRCC. In addition, on univariate analysis, patients with PD-L1 positively in tumor cells were significantly more likely to have a shorter OS. Furthermore, a trend for shorter OS was also observed in patients with PD-L1+TIMCs and both PD-L1 positively on tumor cell membrane and TIMCs were associated with lower TTR. Multivariate analyses indicate that tumor stage, Fuhrman grade and histology are significant effect modifiers for the association of PD-L1 positively on clinical outcome. It has also been confirmed herein that that PD-L1 expression can exist in benign kidney tumors, as previously reported in Boorjian et al. (2009) *Urology* 74:1359-1364.

Infiltrating mononuclear cells in RCC release cytokines to either promote tumor growth or impair anti-tumor immune responses. In addition, high levels of TILs have been associated with an increased risk for cancer progression and death (Webster et al. (2006) *Cancer* 107:46-53). Similarly, higher expression of PD-L1 in TILs was also associated with aggressive features such as tumor grade and TNM stage in ccRCC (Thompson et al. (2007) *Clin. Cancer Res.* 13:1757-1761). Among non-ccRCCs, no statistically significant association between PD-L1 expression in TIMCs and clinicopathological features or OS was observed. Nonetheless, the percentage of patients who were considered PD-L1+ by this method was overall much higher than with the tumor membrane staining.

In the analysis described herein, PD-L1 expression in non-ccRCC was shown to be heterogeneous and dependent on histology. In 2004, the World Health Organization (WHO) classification of renal tumors recognized a new subtype of kidney cancer characterized by translocations involving the transcription factor E3 (TFE3) located on Xp11.2 gene (Malouf et al. (2011) *J. Urol.* 185:24-29). These tumors share some morphological features with ccRCC and the real incidence of this subtype may be underestimated (Bellmunt et al. (2010) *J. Clin. Oncol.* 28:1850-1855). Aggressive clinical course in a younger adult population with a female predominance has been reported. Despite anti-VEGF drugs having some activity in these patients, there is no established treatment for patients with metastatic disease (Malouf et al. (2010) *Ann. Oncol.* 21:1834-1838). In the described herein, 3 out of 10 patients who had Xp11.2 translocation RCC (30%) exhibited PD-L1+ in tumor cells and 9 of 10 (90%) harbored PD-L1+ TIMC. Collecting duct carcinomas are also a very aggressive disease and up to 40% of patients present with metastatic disease at diagnosis (Bellmunt and Dutcher (2013) *Ann. Oncol.* 24:1730-1740). In our study, 1 out of 5 patients expressed PD-L1 on tumor cells and all of them were considered positive in TIMC. Thus, it is believed that PD-L1 plays a key role in the biology of Xp11.2 translocation RCC and collecting duct carcinoma and could represent an important therapeutic target for these RCC subtypes for which few therapeutic options are currently available.

In summary, PD-L1 expression in tumor and TIMC occurs in patients with non-ccRCC depending on histology subtype and tumor membrane vs. immune cell scoring. In addition, PD-L1 positively on tumors cell membrane was associated with aggressive clinico-pathological features.

Example 5: Differential Expression of LKB1, PD-L1, and PD-L2 in KRAS-Mutant Non-Small Cell Lung Cancer (NSCLC) in Never-*Smokers*

KRAS mutation is the most common oncogeniet alteration in lung adenocarcinoma and is detected in 30% of smokers and up to 15% in never-smokers. The tumor suppressor LKB1 is commonly mutated in NSCLC and LKB1 mutations occur concurrently in 30% of KRAS mutant NSCLC. In murine models, Kras mutant tumors with concurrent Lkb1 loss demonstrated more aggressive phenotype, and more frequent metastasis, and did not respond to docetaxel/selumetinib treatment. Immune checkpoint blockade by anti-PD-1/PD-L1 monoclonal antibodies (mAb) is being clinically evaluated. Clinical responses to these agents seems to correlate with PD-L1 expression and smoking status (Riely et al. (2008) *CCR* 14:5731-5734; Ihle et al. (2012) *JNCI* 104:228-239; Imileinski et al. (2012) *Cell* 150:1107-1120; Chen et al. (2012) *Nature* 483:613-617; Butaney et al. (2012) *JCO* 30:supp. (abstract 7588); Topalian et al. (2012) *NEJM* 366:2443-2454). The expression of LKB1, PD-L1 and PD-L2 in KRAS mutant NSCLC from smokers was determined and compared to never-smokers.

Using an institutional database, five hundred and fourteen KRAS mutant NSCLC patients were identified and 1,818 were tested (incidence 28%) of which 42 were never-smokers (8% of KRAS mutations). FFPE archival specimens were retrieved from 31 never-smoker patients and 123 smokers patients. The specimens were analyzed for clinical and molecular characteristics and examined for LKB1, PD-L1, PD-L2 tumor expression, and PD-1 tumor-infiltrating lymphocytes (TILs) by immunohistochemistry (IHC) using murine mAbs as follows: LKB1 (clone Ley37D/G6): An IHC assay for LKB1 detection in KRAS NSCLC was optimized and validated. A panel of cell lines that were FFPE, and clinical samples with known LKB1 status were used. A dilution 1:15,000 was selected for subsequent studies. LKB1 staining was scored as intact or lost, with any degree of expression qualifying as intact. PD-L1 (clone 9A1): Expression was considered positive if >5% of cancer cells had cell membrane staining. PD-L2 (clone 9E5): Expression was considered positive if >10% of cancer cells had cytoplasm staining. Both PD-L1 and PD-L2 were scored for intensity (0: negative; 1: weak; 2: moderate; 3: intense) and percentage of positive cancer cells. PD-1 (clone EH33): Positive cells were counted under 20× middle power field. For each slide, 5 representative areas were chosen to count, and the average number was recorded. TILs were evaluated by CD3 standard staining.

In addition to smoking status, LKB1 was found loss more frequently with KRAS transversion mutations (p=0.029) with a borderline trend in stage IV disease (p=0.07). No differences by KRAS mutation or other demographics were found. KRAS mutant patients with stage IV disease and LKB1 loss had higher number of metastatic sites at the time of diagnosis (median 2.5 vs. 2.0, p=0.01) and developed brain metastasis more frequently (48% vs. 25%, p=0.02).

OS and PFS in KRAS mutant patients who received 1st line cytotoxic chemotherapy for stage IV disease at DFCI in LKB1 intact vs. loss patients were compared. Patients with <1 year prior adjuvant therapy or chemoradiation or untreated brain metastases were excluded. PD-L1 was positive in 29/118 pts (25%; 95% CI, 18-33%) and it was related to smoking status. Smokers, especially current smokers, had increased incidence of PD-L1 expression and also trend towards higher scores. Median percentage of expression did not show differences between smokers vs. never-smokers (61% vs. 51%, respectively).

PD-L2 was positive in 54/114 pts (47%; 95% CI 38%-56%) and it was not related to smoking status. Neither intensity or median percentage of PD-L2 tumor expression varied between smokers and never-smokers (43% vs. 49%). Neither PD-L1 or PD-L2 expression was associated with the type of KRAS mutation.

PD-1 positive TILs were found in up to 93% of PD-L1 and PD-L2 positive samples (median 24 and 13 counts, respectively) but only in the group of PD-L1+ and IHC-3+ were there were more PD-1+ cells. There was no clear association between PD-L1 and PD-L2 expression.

Thus. KRAS mutant NSCLC appears to be a heterogeneous disease. KRAS mutations also occur in never-smokers with an incidence of 10% in the Caucasian population. No clinical differences versus smokers were observed, but a different mutational profile was observed. LKB1 mutations were related to smoking and loss occurs frequently in smokers versus never-smokers. LKB1 loss confers poor prognosis to stage IV patients (e.g., shorter OS and increased sites of metastasis, including brain metastasis). PD-L1 expression in KRAS mutant NSCLC was low and related to smoking status. PD-L2 was nearly double expressed than PD-L1 in KRA mutant NSCLC but was not related to smoking status.

Example 6: Expression of the Immunosuppressive Molecule PD-L1 in HPV+ and HPV− Vulvar Squamous Cell Carcinoma Select tumors express programmed death ligand 1 (PD-L1) to engage PD-1 on T cells and inhibit anti-tumor immunity. Blockade of PD-1 signaling with therapeutic anti-PD-L1 or anti-PD-1 antibodies has resulted in durable clinical responses in a subset of patients with lung adenocarcinoma, renal cell carcinoma, and melanoma. PD-L1 is upregulated in many EBV+ and HHV8+ lymphomas consistent with the notion that viral-driven tumors can co-opt the PD-1 signaling axis for immune evasion. In this study, whether PD-L1 expression is characteristic of HPV+ and HPV− vulvar squamous cell carcinoma (SCC) was analyzed in order to determine whether patients with these tumors are rational candidates for immunotherapy.

Whole tissue sections from 50 vulvar SCC (14 HPV+; 36 HPV−) were evaluated for PD-L1 expression using immunohistochemistry (clone 9A11). Semi-quantitative scoring was performed for intensity (0=negative, 1=weak, 2=moderate, 3=strong) and percentage of tumors cell positive (0<10%, 1=10-50%, and 2=>50%). For statistical analysis, all positive cases were defined as >10% positively, and those with >50% positively were considered "strong positive" cases.

Twelve SCC (24%; 5 HPV+, 7 HPV−) showed <10% positively, 24 SCC (48%; 9 HPV+, 15 HPV−) showed 10-50% positively, and 14 (28%; 0 HPV+, 14 HPV−) showed >50% positively for PD-L1. Strong positive cases (>50% tumor cells expressing PD-L1) were significantly associated with HPV negative status (p=0.005).

Thus, vulvar SCC frequently express PD-L1 and the majority of patients with this tumor-type are rational candidates for anti-PD-L1 or anti-PD-1 immunotherapy. Surprisingly, PD-L1L expression in vulvar SCC was inversely correlated with HPV status, indicating that HPV+ tumors utilize alternate mechanisms for immune evasion.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments of the present invention described herein. Such equivalents are intended to be encompassed by the following claims.

SEQUENCE LISTING

```
<160> NUMBER OF SEQ ID NOS: 31

<210> SEQ ID NO 1
<211> LENGTH: 19
<212> TYPE: PRT
<213> ORGANISM: Artificial Sequence
<220> FEATURE:
<223> OTHER INFORMATION: /note="Description of Artificial Sequence: Homo
      sapiens PD-L1m C-terminal peptide"

<400> SEQUENCE: 1

Cys Gly Ile Gln Asp Thr Asn Ser Lys Lys Gln Ser Asp Thr His Leu
1               5                   10                  15

Glu Glu Thr

<210> SEQ ID NO 2
<211> LENGTH: 132
<212> TYPE: PRT
<213> ORGANISM: Artificial Sequence
<220> FEATURE:
<223> OTHER INFORMATION: /note="Description of Artificial Sequence: 9A11
      vK amino acid sequence"

<400> SEQUENCE: 2
```

```
Met Arg Cys Leu Val Gln Phe Leu Gly Leu Leu Val Leu Trp Ile Pro
1               5                   10                  15

Gly Ser Thr Ala Asp Ile Val Met Thr Gln Ala Ala Phe Ser Asn Pro
            20                  25                  30

Val Thr Leu Gly Thr Ser Ala Ser Ile Ser Cys Arg Ser Ser Lys Ser
        35                  40                  45

Leu Leu His Ser Asn Gly Ile Thr Tyr Leu Tyr Trp Tyr Leu Gln Lys
    50                  55                  60

Pro Gly Gln Ser Pro Gln Leu Leu Ile Tyr Gln Met Ser Asn Leu Ala
65              70                  75                  80

Ser Gly Val Pro Asp Arg Phe Ser Gly Ser Gly Ser Gly Thr Asp Phe
            85                  90                  95

Thr Leu Arg Ile Ser Arg Val Glu Ala Glu Asp Val Gly Val Tyr Tyr
        100                 105                 110

Cys Ala Gln Asn Leu Glu Pro Pro Leu Thr Phe Gly Ala Gly Thr Lys
            115                 120                 125

Leu Glu Leu Lys
    130
```

<210> SEQ ID NO 3
<211> LENGTH: 396
<212> TYPE: DNA
<213> ORGANISM: Artificial Sequence
<220> FEATURE:
<223> OTHER INFORMATION: /note="Description of Artificial Sequence: 9A11 vK cDNA sequence"

<400> SEQUENCE: 3

```
atgaggtgcc ttgttcagtt tctggggctg cttgtgctct ggatccctgg atccactgca      60
gatattgtga tgacgcaggc tgcattctcc aatccagtca ctcttggaac atcagcttcc     120
atctcctgca ggtccagtaa gagtctccta catagtaatg gcatcactta tttgtattgg     180
tatctgcaga agccaggcca gtctcctcag ctcctgattt atcagatgtc caaccttgcc     240
tcaggagtcc cagacaggtt cagtggcagt gggtcaggaa ctgatttcac actgagaatc     300
agcagagtgg aggctgagga tgtgggtgtt tattactgtg ctcaaaatct agaacctccg     360
ctcacgttcg gtgctgggac caagctggag ctgaaa                               396
```

<210> SEQ ID NO 4
<211> LENGTH: 60
<212> TYPE: DNA
<213> ORGANISM: Artificial Sequence
<220> FEATURE:
<223> OTHER INFORMATION: /note="Description of Artificial Sequence: 9A11 vK signal peptide cDNA sequence"

<400> SEQUENCE: 4

```
atgaggtgcc ttgttcagtt tctggggctg cttgtgctct ggatccctgg atccactgca      60
```

<210> SEQ ID NO 5
<211> LENGTH: 69
<212> TYPE: DNA
<213> ORGANISM: Artificial Sequence
<220> FEATURE:
<223> OTHER INFORMATION: /note="Description of Artificial Sequence: 9A11 vK framework 1 cDNA sequence"

<400> SEQUENCE: 5

```
gatattgtga tgacgcaggc tgcattctcc aatccagtca ctcttggaac atcagcttcc      60
``` atctcctgc					69

<210> SEQ ID NO 6
<211> LENGTH: 48
<212> TYPE: DNA
<213> ORGANISM: Artificial Sequence
<220> FEATURE:
<223> OTHER INFORMATION: /note="Description of Artificial Sequence: 9A11
      vK CDR-L1 cDNA sequence"

<400> SEQUENCE: 6
aggtccagta agagtctcct acatagtaat ggcatcactt atttgtat					48

<210> SEQ ID NO 7
<211> LENGTH: 16
<212> TYPE: PRT
<213> ORGANISM: Artificial Sequence
<220> FEATURE:
<223> OTHER INFORMATION: /note="Description of Artificial Sequence: 9A11
      vK CDR-L1 amino acid sequence"

<400> SEQUENCE: 7

Arg Ser Ser Lys Ser Leu Leu His Ser Asn Gly Ile Thr Tyr Leu Tyr
1               5                   10                  15

<210> SEQ ID NO 8
<211> LENGTH: 45
<212> TYPE: DNA
<213> ORGANISM: Artificial Sequence
<220> FEATURE:
<223> OTHER INFORMATION: /note="Description of Artificial Sequence: 9A11
      vK framework 2 cDNA sequence"

<400> SEQUENCE: 8
tggtatctgc agaagccagg ccagtctcct cagctcctga tttat					45

<210> SEQ ID NO 9
<211> LENGTH: 21
<212> TYPE: DNA
<213> ORGANISM: Artificial Sequence
<220> FEATURE:
<223> OTHER INFORMATION: /note="Description of Artificial Sequence: 9A11
      vK CDR-L2 cDNA sequence"

<400> SEQUENCE: 9
cagatgtcca accttgcctc a					21

<210> SEQ ID NO 10
<211> LENGTH: 7
<212> TYPE: PRT
<213> ORGANISM: Artificial Sequence
<220> FEATURE:
<223> OTHER INFORMATION: /note="Description of Artificial Sequence: 9A11
      vK CDR-L2 amino acid sequence"

<400> SEQUENCE: 10

Gln Met Ser Asn Leu Ala Ser
1               5

<210> SEQ ID NO 11
<211> LENGTH: 96
<212> TYPE: DNA
<213> ORGANISM: Artificial Sequence
<220> FEATURE:
<223> OTHER INFORMATION: /note="Description of Artificial Sequence: 9A11
      vK framework 3 cDNA sequence"

<400> SEQUENCE: 11

```
ggagtcccag acaggttcag tggcagtggg tcaggaactg atttcacact gagaatcagc    60
agagtggagg ctgaggatgt gggtgtttat tactgt                              96
```

<210> SEQ ID NO 12
<211> LENGTH: 27
<212> TYPE: DNA
<213> ORGANISM: Artificial Sequence
<220> FEATURE:
<223> OTHER INFORMATION: /note="Description of Artificial Sequence: 9A11 vK CDR-L3 cDNA sequence"

<400> SEQUENCE: 12

```
gctcaaaatc tagaacctcc gctcacg                                        27
```

<210> SEQ ID NO 13
<211> LENGTH: 9
<212> TYPE: PRT
<213> ORGANISM: Artificial Sequence
<220> FEATURE:
<223> OTHER INFORMATION: /note="Description of Artificial Sequence: 9A11 vK CDR-L3 amino acid sequence"

<400> SEQUENCE: 13

Ala Gln Asn Leu Glu Pro Pro Leu Thr
 1               5

<210> SEQ ID NO 14
<211> LENGTH: 30
<212> TYPE: DNA
<213> ORGANISM: Artificial Sequence
<220> FEATURE:
<223> OTHER INFORMATION: /note="Description of Artificial Sequence: 9A11 vK J segment cDNA sequence"

<400> SEQUENCE: 14

```
ttcggtgctg ggaccaagct ggagctgaaa                                     30
```

<210> SEQ ID NO 15
<211> LENGTH: 138
<212> TYPE: PRT
<213> ORGANISM: Artificial Sequence
<220> FEATURE:
<223> OTHER INFORMATION: /note="Description of Artificial Sequence: 9A11 vH amino acid sequence"

<400> SEQUENCE: 15

Met Lys Cys Ser Trp Val Ile Val Phe Leu Met Ala Val Val Ile Gly
 1               5                   10                  15

Ile Asn Ser Glu Val Gln Leu Gln Gln Ser Gly Ala Glu Leu Val Arg
                20                  25                  30

Ser Gly Ala Ser Val Lys Leu Ser Cys Thr Ala Phe Gly Leu Asn Ile
            35                  40                  45

Lys Asp Tyr Tyr Ile His Trp Val Lys Gln Arg Pro Glu Gln Gly Leu
        50                  55                  60

Glu Trp Ile Gly Trp Ile Asp Pro Glu Asn Gly Lys Thr Ala Tyr Ala
 65                 70                  75                  80

Pro Lys Phe Gln Gly Lys Ala Thr Leu Thr Ala Tyr Thr Ser Ser Asp
                85                  90                  95

Thr Ala Tyr Leu His Leu Ser Ser Leu Thr Ser Glu Asp Thr Ala Val
            100                 105                 110

Tyr Tyr Cys Lys Thr Gly Gly Tyr Asp Val Tyr Phe Leu Asp Tyr Trp
        115                 120                 125

Gly Gln Gly Thr Ser Val Thr Val Ser Ser
    130                 135

```
<210> SEQ ID NO 16
<211> LENGTH: 414
<212> TYPE: DNA
<213> ORGANISM: Artificial Sequence
<220> FEATURE:
<223> OTHER INFORMATION: /note="Description of Artificial Sequence: 9A11
      vH cDNA sequence"

<400> SEQUENCE: 16
atgaaatgca gctgggtcat cgtcttcctg atggcagtgg ttataggaat caattcagag      60
gttcagctgc agcagtctgg ggcagagctt gtgaggtcag gggcctcagt caagttgtcc     120
tgcacagctt ttggcctcaa cattaaagac tactatatac actgggtaaa acagaggcct     180
gaacagggcc tggagtggat tggatggatt gatcctgaga atggtaaaac tgcatatgcc     240
ccgaagttcc agggcaaggc cactctgact gcatacacgt cctccgacac agcctacctg     300
cacctcagca gcctgacatc tgaggacact gccgtctatt actgtaagac tggtggttac     360
gacgtctatt ttctggacta ctggggtcaa ggaacctcag tcaccgtctc ctca           414

<210> SEQ ID NO 17
<211> LENGTH: 57
<212> TYPE: DNA
<213> ORGANISM: Artificial Sequence
<220> FEATURE:
<223> OTHER INFORMATION: /note="Description of Artificial Sequence: 9A11
      vH signal peptide cDNA sequence"

<400> SEQUENCE: 17
atgaaatgca gctgggtcat cgtcttcctg atggcagtgg ttataggaat caattca        57

<210> SEQ ID NO 18
<211> LENGTH: 90
<212> TYPE: DNA
<213> ORGANISM: Artificial Sequence
<220> FEATURE:
<223> OTHER INFORMATION: /note="Description of Artificial Sequence: 9A11
      vH framework 1 cDNA sequence"

<400> SEQUENCE: 18
gaggttcagc tgcagcagtc tggggcagag cttgtgaggt caggggcctc agtcaagttg      60
tcctgcacag cttttggcct caacattaaa                                      90

<210> SEQ ID NO 19
<211> LENGTH: 15
<212> TYPE: DNA
<213> ORGANISM: Artificial Sequence
<220> FEATURE:
<223> OTHER INFORMATION: /note="Description of Artificial Sequence: 9A11
      vH CDR-H1 cDNA sequence"

<400> SEQUENCE: 19
gactactata tacac                                                      15

<210> SEQ ID NO 20
<211> LENGTH: 5
<212> TYPE: PRT
<213> ORGANISM: Artificial Sequence
<220> FEATURE:
<223> OTHER INFORMATION: /note="Description of Artificial Sequence: 9A11
      vH CDR-H1 amino acid sequence"
```

```
<400> SEQUENCE: 20

Asp Tyr Tyr Ile His
1               5

<210> SEQ ID NO 21
<211> LENGTH: 42
<212> TYPE: DNA
<213> ORGANISM: Artificial Sequence
<220> FEATURE:
<223> OTHER INFORMATION: /note="Description of Artificial Sequence: 9A11
      vH framework 2 cDNA sequence"

<400> SEQUENCE: 21
tgggtaaaac agaggcctga acagggcctg gagtggattg ga                    42

<210> SEQ ID NO 22
<211> LENGTH: 51
<212> TYPE: DNA
<213> ORGANISM: Artificial Sequence
<220> FEATURE:
<223> OTHER INFORMATION: /note="Description of Artificial Sequence: 9A11
      vH CDR-H2 cDNA sequence"

<400> SEQUENCE: 22
tggattgatc ctgagaatgg taaaactgca tatgccccga agttccaggg c           51

<210> SEQ ID NO 23
<211> LENGTH: 17
<212> TYPE: PRT
<213> ORGANISM: Artificial Sequence
<220> FEATURE:
<223> OTHER INFORMATION: /note="Description of Artificial Sequence: 9A11
      vH CDR-H2 amino acid sequence"

<400> SEQUENCE: 23

Trp Ile Asp Pro Glu Asn Gly Lys Thr Ala Tyr Ala Pro Lys Phe Gln
1               5                   10                  15

Gly

<210> SEQ ID NO 24
<211> LENGTH: 96
<212> TYPE: DNA
<213> ORGANISM: Artificial Sequence
<220> FEATURE:
<223> OTHER INFORMATION: /note="Description of Artificial Sequence: 9A11
      vH framework 3 cDNA sequence"

<400> SEQUENCE: 24
aaggccactc tgactgcata cacgtcctcc gacacagcct acctgcacct cagcagcctg   60
acatctgagg acactgccgt ctattactgt aagact                             96

<210> SEQ ID NO 25
<211> LENGTH: 30
<212> TYPE: DNA
<213> ORGANISM: Artificial Sequence
<220> FEATURE:
<223> OTHER INFORMATION: /note="Description of Artificial Sequence: 9A11
      vH CDR-H3 cDNA sequence"

<400> SEQUENCE: 25
ggtggttacg acgtctattt tctggactac                                  30

<210> SEQ ID NO 26
<211> LENGTH: 10
<212> TYPE: PRT
```

```
<213> ORGANISM: Artificial Sequence
<220> FEATURE:
<223> OTHER INFORMATION: /note="Description of Artificial Sequence: 9A11
      vH CDR-H3 amino acid sequence"

<400> SEQUENCE: 26

Gly Gly Tyr Asp Val Tyr Phe Leu Asp Tyr
1               5                   10

<210> SEQ ID NO 27
<211> LENGTH: 33
<212> TYPE: DNA
<213> ORGANISM: Artificial Sequence
<220> FEATURE:
<223> OTHER INFORMATION: /note="Description of Artificial Sequence: 9A11
      vH J segment cDNA sequence"

<400> SEQUENCE: 27
tggggtcaag gaacctcagt caccgtctcc tca                              33

<210> SEQ ID NO 28
<211> LENGTH: 968
<212> TYPE: DNA
<213> ORGANISM: Homo sapiens
<220> FEATURE:
<221> NAME/KEY: exon
<222> LOCATION: (59)..(793)

<400> SEQUENCE: 28
gcttcccgag gctccgcacc agccgcgctt ctgtccgcct gcagggcatt ccagaaag       58 atg agg ata ttt gct gtc ttt ata ttc atg acc tac tgg cat ttg ctg     106
Met Arg Ile Phe Ala Val Phe Ile Phe Met Thr Tyr Trp His Leu Leu
1               5                   10                  15 aac gca ttt act gtc acg gtt ccc aag gac cta tat gtg gta gag tat     154
Asn Ala Phe Thr Val Thr Val Pro Lys Asp Leu Tyr Val Val Glu Tyr
                20                  25                  30 ggt agc aat atg aca att gaa tgc aaa ttc cca gta gaa aaa caa tta     202
Gly Ser Asn Met Thr Ile Glu Cys Lys Phe Pro Val Glu Lys Gln Leu
            35                  40                  45 gac ctg gct gca cta att gtc tat tgg gaa atg gag gat aag aac att     250
Asp Leu Ala Ala Leu Ile Val Tyr Trp Glu Met Glu Asp Lys Asn Ile
        50                  55                  60 att caa ttt gtg cat gga gag gaa gac ctg aag gtt cag cat agt agc     298
Ile Gln Phe Val His Gly Glu Glu Asp Leu Lys Val Gln His Ser Ser
65                  70                  75                  80 tac aga cag agg gcc cgg ctg ttg aag gac cag ctc tcc ctg gga aat     346
Tyr Arg Gln Arg Ala Arg Leu Leu Lys Asp Gln Leu Ser Leu Gly Asn
                85                  90                  95 gct gca ctt cag atc aca gat gtg aaa ttg cag gat gca ggg gtg tac     394
Ala Ala Leu Gln Ile Thr Asp Val Lys Leu Gln Asp Ala Gly Val Tyr
            100                 105                 110 cgc tgc atg atc agc tat ggt ggt gcc gac tac aag cga att act gtg     442
Arg Cys Met Ile Ser Tyr Gly Gly Ala Asp Tyr Lys Arg Ile Thr Val
        115                 120                 125 aaa gtc aat gcc cca tac aac aaa atc aac caa aga att ttg gtt gtg     490
Lys Val Asn Ala Pro Tyr Asn Lys Ile Asn Gln Arg Ile Leu Val Val
130                 135                 140 gat cca gtc acc tct gaa cat gaa ctg aca tgt cag gct gag ggc tac     538
Asp Pro Val Thr Ser Glu His Glu Leu Thr Cys Gln Ala Glu Gly Tyr
145                 150                 155                 160 ccc aag gcc gaa gtc atc tgg aca agc agt gac cat caa gtc ctg agt     586
Pro Lys Ala Glu Val Ile Trp Thr Ser Ser Asp His Gln Val Leu Ser
                165                 170                 175
```

```
ggt aag acc acc acc acc aat tcc aag aga gag gag aag ctt ttc aat    634
Gly Lys Thr Thr Thr Thr Asn Ser Lys Arg Glu Glu Lys Leu Phe Asn
            180                 185                 190 gtg acc agc aca ctg aga atc aac aca aca act aat gag att ttc tac    682
Val Thr Ser Thr Leu Arg Ile Asn Thr Thr Thr Asn Glu Ile Phe Tyr
        195                 200                 205 tgc act ttt agg aga tta gat cct gag gaa aac cat aca gct gaa ttg    730
Cys Thr Phe Arg Arg Leu Asp Pro Glu Glu Asn His Thr Ala Glu Leu
    210                 215                 220 gtc atc cca ggt aat att ctg aat gtg tcc att aaa ata tgt cta aca    778
Val Ile Pro Gly Asn Ile Leu Asn Val Ser Ile Lys Ile Cys Leu Thr
225                 230                 235                 240 ctg tcc cct agc acc tagcatgatg tctgcctatc atagtcattc agtgattgtt   833
Leu Ser Pro Ser Thr
                245 gaataaatga atgaatgaat aacactatgt ttacaaaata tatcctaatt cctcacctcc   893 attcatccaa accatattgt tacttaataa acattcagca gatatttatg gaataaaaaa   953 aaaaaaaaaa aaaaa                                                    968

<210> SEQ ID NO 29
<211> LENGTH: 245
<212> TYPE: PRT
<213> ORGANISM: Homo sapiens

<400> SEQUENCE: 29

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240
```

```
Leu Ser Pro Ser Thr
            245

<210> SEQ ID NO 30
<211> LENGTH: 1553
<212> TYPE: DNA
<213> ORGANISM: Homo sapiens
<220> FEATURE:
<221> NAME/KEY: exon
<222> LOCATION: (53)..(922)

<400> SEQUENCE: 30
cgaggctccg caccagccgc gcttctgtcc gcctgcaggg cattccagaa ag atg agg      58
                                                         Met Arg
                                                          1 ata ttt gct gtc ttt ata ttc atg acc tac tgg cat ttg ctg aac gca      106
Ile Phe Ala Val Phe Ile Phe Met Thr Tyr Trp His Leu Leu Asn Ala
         5                  10                  15 ttt act gtc acg gtt ccc aag gac cta tat gtg gta gag tat ggt agc      154
Phe Thr Val Thr Val Pro Lys Asp Leu Tyr Val Val Glu Tyr Gly Ser
 20                  25                  30 aat atg aca att gaa tgc aaa ttc cca gta gaa aaa caa tta gac ctg      202
Asn Met Thr Ile Glu Cys Lys Phe Pro Val Glu Lys Gln Leu Asp Leu
 35                  40                  45                  50 gct gca cta att gtc tat tgg gaa atg gag gat aag aac att att caa      250
Ala Ala Leu Ile Val Tyr Trp Glu Met Glu Asp Lys Asn Ile Ile Gln
                 55                  60                  65 ttt gtg cat gga gag gaa gac ctg aag gtt cag cat agt agc tac aga      298
Phe Val His Gly Glu Glu Asp Leu Lys Val Gln His Ser Ser Tyr Arg
             70                  75                  80 cag agg gcc cgg ctg ttg aag gac cag ctc tcc ctg gga aat gct gca      346
Gln Arg Ala Arg Leu Leu Lys Asp Gln Leu Ser Leu Gly Asn Ala Ala
         85                  90                  95 ctt cag atc aca gat gtg aaa ttg cag gat gca ggg gtg tac cgc tgc      394
Leu Gln Ile Thr Asp Val Lys Leu Gln Asp Ala Gly Val Tyr Arg Cys
100                 105                 110 atg atc agc tat ggt ggt gcc gac tac aag cga att act gtg aaa gtc      442
Met Ile Ser Tyr Gly Gly Ala Asp Tyr Lys Arg Ile Thr Val Lys Val
115                 120                 125                 130 aat gcc cca tac aac aaa atc aac caa aga att ttg gtt gtg gat cca      490
Asn Ala Pro Tyr Asn Lys Ile Asn Gln Arg Ile Leu Val Val Asp Pro
                135                 140                 145 gtc acc tct gaa cat gaa ctg aca tgt cag gct gag ggc tac ccc aag      538
Val Thr Ser Glu His Glu Leu Thr Cys Gln Ala Glu Gly Tyr Pro Lys
            150                 155                 160 gcc gaa gtc atc tgg aca agc agt gac cat caa gtc ctg agt ggt aag      586
Ala Glu Val Ile Trp Thr Ser Ser Asp His Gln Val Leu Ser Gly Lys
        165                 170                 175 acc acc acc acc aat tcc aag aga gag gag aag ctt ttc aat gtg acc      634
Thr Thr Thr Thr Asn Ser Lys Arg Glu Glu Lys Leu Phe Asn Val Thr
    180                 185                 190 agc aca ctg aga atc aac aca aca act aat gag att ttc tac tgc act      682
Ser Thr Leu Arg Ile Asn Thr Thr Thr Asn Glu Ile Phe Tyr Cys Thr
195                 200                 205                 210 ttt agg aga tta gat cct gag gaa aac cat aca gct gaa ttg gtc atc      730
Phe Arg Arg Leu Asp Pro Glu Glu Asn His Thr Ala Glu Leu Val Ile
                215                 220                 225 cca gaa cta cct ctg gca cat cct cca aat gaa agg act cac ttg gta      778
Pro Glu Leu Pro Leu Ala His Pro Pro Asn Glu Arg Thr His Leu Val
            230                 235                 240
```

```
att ctg gga gcc atc tta tta tgc ctt ggt gta gca ctg aca ttc atc      826
Ile Leu Gly Ala Ile Leu Leu Cys Leu Gly Val Ala Leu Thr Phe Ile
            245                 250                 255 ttc cgt tta aga aaa ggg aga atg atg gat gtg aaa aaa tgt ggc atc      874
Phe Arg Leu Arg Lys Gly Arg Met Met Asp Val Lys Lys Cys Gly Ile
260                 265                 270 caa gat aca aac tca aag aag caa agt gat aca cat ttg gag gag acg      922
Gln Asp Thr Asn Ser Lys Lys Gln Ser Asp Thr His Leu Glu Glu Thr
275                 280                 285                 290 taatccagca ttggaacttc tgatcttcaa gcagggattc tcaacctgtg gtttaggggt    982 tcatcgggc tgagcgtgac aagaggaagg aatgggcccg tgggatgcag caatgtggg     1042 acttaaaagg cccaagcact gaaaatggaa cctggcgaaa gcagaggagg agaatgaaga   1102
aagatggagt caaacaggga gcctggaggg agaccttgat actttcaaat gcctgagggg   1162
ctcatcgacg cctgtgacag ggagaaagga tacttctgaa caaggagcct ccaagcaaat   1222
catccattgc tcatcctagg aagacgggtt gagaatccct aatttgaggg tcagttcctg   1282
cagaagtgcc ctttgcctcc actcaatgcc tcaatttgtt ttctgcatga ctgagagtct   1342
cagtgttgga acgggacagt atttatgtat gagttttttcc tatttatttt gagtctgtga  1402
ggtcttcttg tcatgtgagt gtggttgtga atgatttctt ttgaagatat attgtagtag   1462
atgttacaat tttgtcgcca aactaaactt gctgcttaat gatttgctca catctagtaa   1522
aacatggagt atttgtaaaa aaaaaaaaa a                                    1553
```

<210> SEQ ID NO 31
<211> LENGTH: 290
<212> TYPE: PRT
<213> ORGANISM: Homo sapiens

<400> SEQUENCE: 31

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
```

-continued

```
            195                 200                 205
Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290
```

What is claimed is:

1. A monoclonal antibody, or antigen-binding fragment thereof, that specifically binds human PD-L1 and comprises:
   (a) a light chain variable region (VL) comprising a complementarity determining region ("CDR")-L1 as set forth in SEQ ID NO: 7, a CDR-L2 as set forth in SEQ ID NO: 10, and a CDR-L3 as set forth in SEQ ID NO: 13; and
   (b) a heavy chain variable region (VH) comprising a CDR-H1 as set forth in SEQ ID NO: 20, a CDR-H2 as set forth in SEQ ID NO: 23, and a CDR-H3 as set forth in SEQ ID NO: 26.

2. The monoclonal antibody, or antigen-binding fragment thereof, of claim 1 that is murine, chimeric, or humanized.

3. The antigen-binding fragment of claim 1, wherein the antigen-binding fragment is a Fv, F(ab')2, Fab', sdFv, scFv, sc(Fv)2, or a diabody.

4. The monoclonal antibody of claim 1, wherein the monoclonal antibody comprises an Fc domain.

5. The monoclonal antibody, or antigen-binding fragment thereof, of claim 1, wherein the VL comprises the amino acid sequence set forth in SEQ ID NO: 2.

6. The monoclonal antibody, or antigen-binding fragment thereof, of claim 1, wherein the VH comprises the amino acid sequence set forth in SEQ ID NO: 15.

7. The monoclonal antibody, or antigen-binding fragment thereof, of claim 6, that also comprises the VL set forth in SEQ ID NO: 2.

8. A composition comprising the monoclonal antibody, or antigen-binding fragment thereof, of claim 7 and a physiologically acceptable carrier, excipient, or stabilizer.

9. A composition comprising the monoclonal antibody, or antigen-binding fragment thereof, of claim 1 and a physiologically acceptable carrier, excipient, or stabilizer.

10. A device or kit for detecting membrane-bound PD-L1, the device or kit comprising at least one monoclonal antibody, or antigen-binding fragment thereof, according to claim 1 and a label to detect the at least one monoclonal antibody, or antigen-binding fragment thereof.

11. An immunoconjugate comprising:
   (a) a monoclonal antibody, or antigen-binding fragment thereof, that specifically binds the cytoplasmic region of PD-L1 and that comprises:
      (i) a light chain variable region (VL) comprising a comple mentarity determining region ("CDR")-L1 as set forth in SEQ ID NO: 7, a CDR-L2 as set forth in SEQ ID NO: 10, and a CDR-L3 as set forth in SEQ ID NO: 13; and
      (ii) a heavy chain variable region (VH) comprising a CDR-H1 as set forth in SEQ ID NO: 20, a CDR-H2 as set forth in SEQ ID NO: 23, and a CDR-H3 as set forth in SEQ ID NO: 26; and
   (b) a cytotoxin, a drug, a radioisotope, an enzyme, a prosthetic group, fluorescent material, luminescent material, or bioluminescent material.

12. A method of detecting the presence or level of PD-L1 polypeptide in a sample, the method comprising obtaining a sample and detecting the polypeptide in the sample by contacting the sample with the monoclonal antibody, or antigen-binding fragment thereof, of claim 1 or with the immunoconjugate of claim 11.

13. The method of claim 12, wherein the method is an enzyme-linked immunosorbent assay (ELISA), radioimmune assay (RIA), a flow assay, or an immunohistochemistry (IHC) assay.

14. The method of claim 12, wherein the method is an immunohistochemistry (IHC) assay and the sample is formalin-fixed, paraffin-embedded tumor tissue.

15. An isolated nucleic acid encoding:
   (a) a light chain variable region (VL) comprising a complementarity determining region ("CDR")-L1 as set forth in SEQ ID NO: 7, a CDR-L2 as set forth in SEQ ID NO: 10, and a CDR-L3 as set forth in SEQ ID NO: 13; and
   (b) a heavy chain variable region (VH) comprising a CDR-H1 as set forth in SEQ ID NO: 20, a CDR-H2 as set forth in SEQ ID NO: 23, and a CDR-H3 as set forth in SEQ ID NO: 26; wherein the VH and VL, when expressed together, form an antibody Fv that binds human PD-L1.

16. The isolated nucleic acid of claim 15, comprising (a) the nucleotide sequence set forth in SEQ ID NO: 3, (b) the nucleotide sequence set forth in SEQ ID NO: 16, or (c) both the nucleotide sequence set forth in SEQ ID NO: 3 and the nucleotide sequence set forth in SEQ ID NO: 16.

17. A vector comprising an isolated nucleic acid of claim 15 or an isolated nucleic acid of claim 16.

18. An isolated host cell comprising the vector of claim 17.

19. A method of producing an antibody, or antigen-binding fragment thereof, comprising culturing the host cell of 45 under conditions to allow expression of said antibody or antigen-binding fragment thereof, and recovering the expressed antibody or antigen-binding fragment thereof.

* * * * *